United States Patent
Hinck et al.

(10) Patent No.: US 12,139,531 B2
(45) Date of Patent: Nov. 12, 2024

(54) COMPOSITIONS AND METHODS USEFUL IN PROMOTING MILK PRODUCTION

(71) Applicant: The Regents of the University of California, Oakland, CA (US)

(72) Inventors: Lindsay Hinck, Santa Cruz, CA (US); Sharmila Chatterjee, Santa Cruz, CA (US); Oscar Cazares, Santa Cruz, CA (US); Min Chen, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 1073 days.

(21) Appl. No.: 16/855,883

(22) Filed: Apr. 22, 2020

(65) Prior Publication Data

US 2020/0339676 A1 Oct. 29, 2020

Related U.S. Application Data

(60) Provisional application No. 62/837,590, filed on Apr. 23, 2019.

(51) Int. Cl.
| | | |
|---|---|---|
| *C07K 16/28* | (2006.01) | |
| *A61K 39/00* | (2006.01) | |
| *C07K 14/705* | (2006.01) | |
| *C12N 15/113* | (2010.01) | |

(52) U.S. Cl.
CPC ........ *C07K 16/28* (2013.01); *C07K 14/70503* (2013.01); *C12N 15/1138* (2013.01); *A61K 2039/505* (2013.01); *C07K 2317/22* (2013.01); *C07K 2317/24* (2013.01); *C07K 2319/21* (2013.01); *C07K 2319/30* (2013.01); *C07K 2319/41* (2013.01); *C07K 2319/42* (2013.01); *C07K 2319/60* (2013.01); *C12N 2310/14* (2013.01)

(58) Field of Classification Search
CPC .............. C07K 16/28; C07K 14/70503; C07K 2319/21; C07K 2319/41; C12N 2310/14; C12N 15/1138; A61K 2039/505
See application file for complete search history.

(56) References Cited

U.S. PATENT DOCUMENTS

| | | |
|---|---|---|
| 5,780,009 A | 7/1998 | Karatzas et al. |
| 2008/0132445 A1 | 6/2008 | Ormandy et al. |
| 2009/0312271 A1 | 12/2009 | Menzaghi et al. |
| 2012/0192298 A1 | 7/2012 | Weinstein et al. |
| 2012/0322857 A1 | 12/2012 | Hendrix et al. |
| 2013/0039912 A1 | 2/2013 | Blanche et al. |
| 2015/0291694 A1 | 10/2015 | Aburatani et al. |
| 2017/0096493 A1 | 4/2017 | Sakamoto et al. |
| 2017/0114412 A1 | 4/2017 | Lu et al. |
| 2017/0290844 A1 | 10/2017 | Beinke et al. |

FOREIGN PATENT DOCUMENTS

| | | |
|---|---|---|
| WO | WO2018227063 | 12/2018 |

OTHER PUBLICATIONS

Cazares et al., Alveolar progenitor differentiation and lactation depends on paracrine inhibition of Notch via ROBO1/CTNNB1/JAG1. Development 148 (21): dev199940, 2021.*
Aleksandrova, N. et al. "Robo1 Forms a Compact Dimer-of-Dimers Assembly" Structure, 26:320-328 e324, doi:10.1016/j.str.2017.12.003 (2018).
Ballard, M. S. et al. "Mammary Stem Cell Self-Renewal Is Regulated by Slit2/Robo1 Signaling through SNAI1 and mINSC" Cell reports, 13:290-301, doi:10.1016/j.celrep.2015.09.006 (2015).
Bi, P. et al. "Notch signaling regulates adipose browning and energy metabolism" Nat Med, 20(8):911-918, doi:10.1038/nm.3615 (2014).
Biteau, B. & Jasper, H. "Slit/Robo signaling regulates cell fate decisions in the intestinal stem cell lineage of *Drosophila*" Cell reports, 7:1867-1875, doi:10.1016/j.celrep.2014.05.024 (2014).
Borrell, V. et al. "Slit/Robo signaling modulates the proliferation of central nervous system progenitors" Neuron, 76:338-352, doi:10.1016/j.neuron.2012.08.003 (2012).
Bouras, T. et al. "Notch signaling regulates mammary stem cell function and luminal cell-fate commitment" Cell stem cell, 3:429-441, doi:10.1016/j.stem.2008.08.001 (2008).

(Continued)

*Primary Examiner* — Ruixiang Li
(74) *Attorney, Agent, or Firm* — Bozicevic, Field & Francis LLP; Shweta Chandra

(57) ABSTRACT

Methods, agents, and compositions for promoting milk production in a mammal are provided. Agents useful for promoting milk production may include an agent that inhibits NOTCH4 activity. The agent may inhibit NOTCH4 activity by binding to ROBO2 and/or by binding to NOTCH4. The agent may inhibit NOTCH4 by competing with ROBO1 for binding to ROBO2, thereby making ROBO1 available to inhibit NOTCH4 activity. The agent may be a soluble ROBO1 extracellular domain or an anti-NOTCH4 antibody that inhibits NOTCH4 activity. The agent may be an RNAi construct that inhibits expression of NOTCH4 or an RNAi construct that inhibits expression of ROBO2. Also provided herein are transgenic mammals genetically modified for expression of a soluble ROBO1 extracellular domain; inhibition of expression of ROBO2; and/or inhibition of expression of NOTCH4. Methods for promoting milk production in such transgenic mammals by administering one or more of the agents disclosed herein are also provided.

16 Claims, 13 Drawing Sheets

Specification includes a Sequence Listing.

(56) References Cited

OTHER PUBLICATIONS

Brose, K. et al. "Slit proteins bind Robo receptors and have an evolutionarily conserved role in repulsive axon guidance" Cell, 96:795-806 (1999).
Chakrabarti, R. et al. "Elf5 regulates mammary gland stem/progenitor cell fate by influencing notch signaling" Stem Cells, 30:1496-1508, doi:10.1002/stem.1112 (2012).
Chen, Y. et al. "Inhibition of Notch signaling by a gamma-secretase inhibitor attenuates hepatic fibrosis in rats" PloS one, 7(10):e46512, doi:10.1371/journal.pone.0046512 (2012).
Chillakuri, C. R., et al. "Notch receptor-ligand binding and activation: insights from molecular studies" Semin Cell Dev Biol, 23:421-428, doi:10.1016/j.semcdb.2012.01.009 (2012).
Dickinson, R. E. & Duncan, W. C. "The SLIT-ROBO pathway: a regulator of cell function with implications for the reproductive system" Reproduction, 139:697-704, doi:10.1530/REP-10-0017 (2010).
Dontu, G. et al. "Role of Notch signaling in cell-fate determination of human mammary stem/progenitor cells" Breast Cancer Res, 6:R605-615, doi:10.1186/bcr920 (2004).
Evans, T. A., et al. "Robo2 acts in trans to inhibit Slit-Robo1 repulsion in pre-crossing commissural axons" Elife, 4: e08407, doi:10.7554/eLife.08407 (2015).
Evans, T. A. & Bashaw, G. J. "Functional diversity of Robo receptor immunoglobulin domains promotes distinct axon guidance decisions" Curr Biol, 20:567-572, doi:10.1016/j.cub.2010.02.021 (2010).
Fukuhara, N., et al. "Structural and functional analysis of slit and heparin binding to immunoglobulin-like domains 1 and 2 of Drosophila Robo" J Biol Chem, 283:16226-16234, doi:10.1074/jbc.M800688200 (2008).
Gallahan, D. et al. "Expression of a truncated Int3 gene in developing secretory mammary epithelium specifically retards lobular differentiation resulting in tumorigenesis" Cancer Res, 56:1775-1785 (1996).
Harburg, G. et al. "SLIT/ROBO2 signaling promotes mammary stem cell senescence by inhibiting Wnt signaling" Stem cell reports, 3:385-393, doi:10.1016/j.stemcr.2014.07.007 (2014).
Hivert, B., et al. "Robo1 and Robo2 are homophilic binding molecules that promote axonal growth" Mol Cell Neurosci, 21:534-545 (2002).
Howitt, J. A., et al. "Binding site for Robo receptors revealed by dissection of the leucine-rich repeat region of Slit" EMBO J, 23:4406-4412, doi:10.1038/sj.emboj.7600446 (2004).
Huang, R., et al. "Notch2/Hes-1 pathway plays an important role in renal ischemia and reperfusion injury-associated inflammation and apoptosis and the gamma-secretase inhibitor DAPT has a nephroprotective effect" Ren. Fail. 33:207-216, doi:10.3109/0886022X.2011.553979 (2011).

Jarde, T. et al. "Wnt and Neuregulin1/ErbB signalling extends 3D culture of hormone responsive mammary organoids" Nat Commun, 7:13207, doi:10.1038/ncomms13207 (2016).
Jhappan, C. et al. "Expression of an activated Notch-related int-3 transgene interferes with cell differentiation and induces neoplastic transformation in mammary and salivary glands" Genes Dev, 6:345-355 (1992).
Liu, Z. et al. "Extracellular Ig domains 1 and 2 of Robo are important for ligand (Slit) binding" Mol Cell Neurosci, 26:232-240, doi:10.1016/j.mcn.2004.01.002 (2004).
Lupu, C. et al. "Cellular effects of heparin on the production and release of tissue factor pathway inhibitor in human endothelial cells in culture" Arterioscler Thromb Vasc Biol, 19:2251-2262 (1999).
Macias, H. et al. "SLIT/ROBO1 signaling suppresses mammary branching morphogenesis by limiting basal cell number" Dev Cell, 20:827-840, doi:10.1016/j.devcel.2011.05.012 (2011).
Marlow, R. et al. "SLITs suppress tumor growth in vivo by silencing Sdf1/Cxcr4 within breast epithelium" Cancer Res, 68:7819-7827, doi:10.1158/0008-5472.CAN-08-1357 (2008).
Morlot, C. et al. "Structural insights into the Slit-Robo complex" Proc Natl Acad Sci U S A, 104:14923-14928, doi:10.1073/pnas.0705310104 (2007).
Peschon, J. J. et al. "An essential role for ectodomain shedding in mammalian development" Science, 282:1281-1284 (1998).
Raafat, A. et al. "Expression of Notch receptors, ligands, and target genes during development of the mouse mammary gland" J Cell Physiol, 226:1940-1952, doi:10.1002/jcp.22526 (2011).
Raouf, A. et al. "Transcriptome analysis of the normal human mammary cell commitment and differentiation process" Cell stem cell, 3:109-118, doi:10.1016/j.stem.2008.05.018 (2008).
Regan, J. L. et al. "Aurora A kinase regulates mammary epithelial cell fate by determining mitotic spindle orientation in a Notch-dependent manner" Cell reports, 4:110-123, doi:10.1016/j.celrep.2013.05.044 (2013).
Richter, W. F. & Jacobsen, B. "Subcutaneous absorption of biotherapeutics: knowns and unknowns" Drug Metab. Dispos. 42:1881-1889, doi:10.1124/dmd.114.059238 (2014).
Shore, A. N. et al. "Pregnancy-induced noncoding RNA (PINC) associates with polycomb repressive complex 2 and regulates mammary epithelial differentiation" PLoS Genet, 8:e1002840, doi:10.1371/journal.pgen.1002840 (2012).
Smith, G. H. et al. "Constitutive expression of a truncated INT3 gene in mouse mammary epithelium impairs differentiation and functional development" Cell Growth Differ, 6:563-577 (1995).
Strickland, P. et al. "Slit2 and netrin 1 act synergistically as adhesive cues to generate tubular bi-layers during ductal morphogenesis" Development, 133:823-832 (2006).
James et al. (2014) "Notch4 reveals a novel mechanism regulating Notch signal transduction." Biochimica et Biophysica Acta , vol. 1843, No. 7, pp. 1272-1284.
Rangel et al., (2016) "Developmental signaling pathways regulating mammary stem cells and contributing to the etiology of triple-negative breast cancer." Breast Cancer Res Treat, vol. 156, pp. 211-226.

* cited by examiner

SEQUENCE LISTING

<160> NUMBER OF SEQ ID NOS: 55

<210> SEQ ID NO 1
<211> LENGTH: 832
<212> TYPE: PRT
<213> ORGANISM: Bos taurus

<400> SEQUENCE: 1

```
Met Ile Ala Glu Pro Ala His Phe Tyr Leu Phe Gly Leu Ile Cys Leu
1               5                   10                  15

Cys Ser Gly Ser Arg Leu Arg Gln Glu Asp Phe Pro Pro Arg Ile Val
                20                  25                  30

Glu His Pro Ser Asp Leu Ile Val Ser Lys Gly Glu Pro Ala Thr Leu
            35                  40                  45

Asn Cys Lys Ala Glu Gly Arg Pro Thr Pro Thr Ile Glu Trp Tyr Lys
        50                  55                  60

Gly Gly Glu Arg Val Glu Thr Asp Lys Asp Asp Pro Arg Ser His Arg
65                  70                  75                  80

Met Leu Leu Pro Ser Gly Ser Leu Phe Phe Leu Arg Ile Val His Gly
                85                  90                  95

Arg Lys Ser Arg Pro Asp Glu Gly Val Tyr Val Cys Val Ala Arg Asn
                100                 105                 110

Tyr Leu Gly Glu Ala Val Ser His Asn Ala Ser Leu Glu Val Ala Ile
            115                 120                 125

Leu Arg Asp Asp Phe Arg Gln Asn Pro Ser Asp Val Met Val Ala Val
        130                 135                 140

Gly Glu Pro Ala Val Met Glu Cys Gln Pro Pro Arg Gly His Pro Glu
145                 150                 155                 160

Pro Thr Ile Ser Trp Lys Lys Asp Gly Ser Pro Leu Asp Asp Lys Asp
                165                 170                 175

Glu Arg Ile Thr Ile Arg Gly Gly Lys Leu Met Ile Thr Tyr Thr Arg
            180                 185                 190

Lys Ser Asp Ala Gly Lys Tyr Val Cys Val Gly Thr Asn Met Val Gly
        195                 200                 205
```

```
Glu Arg Glu Ser Glu Val Ala Glu Leu Thr Val Leu Glu Arg Pro Ser
    210             215                 220

Phe Val Lys Arg Pro Ser Asn Leu Ala Val Thr Val Asp Asp Ser Ala
225             230                 235                 240

Glu Phe Lys Cys Glu Ala Arg Gly Asp Pro Val Pro Thr Val Arg Trp
                245                 250                 255

Arg Lys Asp Asp Gly Glu Leu Pro Lys Ser Arg Tyr Glu Ile Arg Asp
            260                 265                 270

Asp His Thr Leu Lys Ile Arg Lys Val Thr Ala Gly Asp Met Gly Ser
            275                 280                 285

Tyr Thr Cys Val Ala Glu Asn Met Val Gly Lys Ala Glu Ala Ser Ala
    290                 295                 300

Thr Leu Thr Val Gln Val Gly Ser Glu Pro Pro His Phe Val Val Lys
305             310                 315                 320

Pro Arg Asp Gln Val Val Ala Leu Gly Arg Thr Val Thr Phe Gln Cys
                325                 330                 335

Glu Ala Thr Gly Asn Pro Gln Pro Ala Ile Phe Trp Arg Arg Glu Gly
            340                 345                 350

Ser Gln Asn Leu Leu Phe Ser Tyr Gln Pro Pro Gln Ser Ser Ser Arg
    355                 360                 365

Phe Ser Val Ser Gln Thr Gly Asp Leu Thr Ile Thr Asn Val Gln Arg
370             375                 380

Ser Asp Val Gly Tyr Tyr Ile Cys Gln Thr Leu Asn Val Ala Gly Ser
385             390                 395                 400

Ile Ile Thr Lys Ala Tyr Leu Glu Val Thr Asp Val Ile Ala Asp Arg
                405                 410                 415

Pro Pro Pro Val Ile Arg Gln Gly Pro Val Asn Gln Thr Val Ala Val
            420                 425                 430

Asp Gly Thr Leu Val Leu Ser Cys Val Ala Thr Gly Ser Pro Val Pro
            435                 440                 445

Thr Ile Leu Trp Arg Lys Asp Gly Val Leu Val Ser Thr Gln Asp Ser
450             455                 460

Arg Ile Lys Gln Leu Glu Thr Gly Val Leu Gln Ile Arg Tyr Ala Lys
465             470                 475                 480

Leu Gly Asp Thr Gly Arg Tyr Thr Cys Ile Ala Ser Thr Pro Ser Gly
            485                 490                 495

Glu Ala Thr Trp Ser Ala Tyr Ile Glu Val Gln Glu Phe Gly Val Pro
                500                 505                 510

Val Gln Pro Pro Arg Pro Thr Asp Pro Asn Leu Ile Pro Ser Ala Pro
    515                 520                 525

Ser Lys Pro Glu Val Thr Asp Val Ser Arg Asn Thr Val Thr Leu Ser
    530                 535                 540

Trp Gln Pro Asn Leu Asn Ser Gly Ala Thr Pro Thr Ser Tyr Ile Ile
545             550                 555                 560

Glu Ala Phe Ser His Ala Ser Gly Ser Ser Trp Gln Thr Val Ala Glu
                565                 570                 575

Asn Val Lys Thr Glu Thr Phe Ala Ile Lys Gly Leu Lys Pro Asn Ala
            580                 585                 590

Ile Tyr Leu Phe Leu Val Arg Ala Ala Asn Ala Tyr Gly Ile Ser Asp
            595                 600                 605

Pro Ser Gln Ile Ser Asp Pro Val Lys Thr Gln Asp Val Pro Pro Thr
    610                 615                 620

Ser Gln Gly Val Asp His Lys Gln Val Gln Arg Glu Leu Gly Asn Val
```

```
                625                 630                 635                 640
Val Leu His Leu His Asn Pro Thr Ile Leu Ser Ser Ser Ile Glu
                        645                 650                 655

Val His Trp Thr Val Asp Gln Gln Ser Gln Tyr Ile Gln Gly Tyr Lys
                360                 665                 670

Val Leu Tyr Arg Pro Ser Gly Ala Asn His Gly Glu Ser Glu Trp Leu
                675                 680                 685

Val Phe Glu Val Arg Thr Pro Thr Lys Asn Ser Val Val Ile Pro Asp
        690                 695                 700

Leu Lys Lys Gly Val Asn Tyr Glu Ile Lys Ala Arg Pro Phe Phe Asn
705                 710                 715                 720

Glu Phe Gln Gly Ala Asp Ser Glu Ile Lys Phe Ala Lys Thr Leu Glu
                        725                 730                 735

Glu Ala Pro Ser Ala Pro Pro Gln Ser Val Thr Val Ser Lys Asn Asp
                740                 745                 750

Gly Asn Gly Thr Ala Ile Leu Val Ser Trp Gln Pro Pro Glu Asp
                755                 760                 765

Thr Gln Asn Gly Met Val Gln Glu Tyr Lys Val Trp Cys Leu Gly Asn
        770                 775                 780

Glu Thr Arg Tyr His Ile Asn Lys Thr Val Asp Gly Ser Thr Phe Ser
785                 790                 795                 800

Val Val Ile Pro Ser Leu Val Pro Gly Ile Arg Tyr Ser Val Glu Val
                        805                 810                 815

Ala Ala Ser Thr Gly Ala Gly Ser Gly Val Lys Ser Glu Pro Gln Phe
                820                 825                 830

<210> SEQ ID NO 2
<211> LENGTH: 509
<212> TYPE: PRT
<213> ORGANISM: Bos taurus

<400> SEQUENCE: 2

Met Ile Ala Glu Pro Ala His Phe Tyr Leu Phe Gly Leu Ile Cys Leu
1               5                   10                  15

Cys Ser Gly Ser Arg Leu Arg Gln Glu Asp Phe Pro Pro Arg Ile Val
                20                  25                  30

Glu His Pro Ser Asp Leu Ile Val Ser Lys Gly Glu Pro Ala Thr Leu
            35                  40                  45

Asn Cys Lys Ala Glu Gly Arg Pro Thr Pro Thr Ile Glu Trp Tyr Lys
        50                  55                  60

Gly Gly Glu Arg Val Glu Thr Asp Lys Asp Asp Pro Arg Ser His Arg
65                  70                  75                  80

Met Leu Leu Pro Ser Gly Ser Leu Phe Phe Leu Arg Ile Val His Gly
                85                  90                  95

Arg Lys Ser Arg Pro Asp Glu Gly Val Tyr Val Cys Val Ala Arg Asn
                100                 105                 110

Tyr Leu Gly Glu Ala Val Ser His Asn Ala Ser Leu Glu Val Ala Ile
            115                 120                 125

Leu Arg Asp Asp Phe Arg Gln Asn Pro Ser Asp Val Met Val Ala Val
        130                 135                 140

Gly Glu Pro Ala Val Met Glu Cys Gln Pro Pro Arg Gly His Pro Glu
145                 150                 155                 160

Pro Thr Ile Ser Trp Lys Lys Asp Gly Ser Pro Leu Asp Asp Lys Asp
                165                 170                 175
```

```
Glu Arg Ile Thr Ile Arg Gly Gly Lys Leu Met Ile Thr Tyr Thr Arg
            180                 185                 190

Lys Ser Asp Ala Gly Lys Tyr Val Cys Val Gly Thr Asn Met Val Gly
            195                 200                 205

Glu Arg Glu Ser Glu Val Ala Glu Leu Thr Val Leu Glu Arg Pro Ser
            210                 215                 220

Phe Val Lys Arg Pro Ser Asn Leu Ala Val Thr Val Asp Asp Ser Ala
225                 230                 235                 240

Glu Phe Lys Cys Glu Ala Arg Gly Asp Pro Val Pro Thr Val Arg Trp
            245                 250                 255

Arg Lys Asp Asp Gly Glu Leu Pro Lys Ser Arg Tyr Glu Ile Arg Asp
            260                 265                 270

Asp His Thr Leu Lys Ile Arg Lys Val Thr Ala Gly Asp Met Gly Ser
            275                 280                 285

Tyr Thr Cys Val Ala Glu Asn Met Val Gly Lys Ala Glu Ser Ala
            290                 295                 300

Thr Leu Thr Val Gln Val Gly Ser Glu Pro His Phe Val Val Lys
305                 310                 315                 320

Pro Arg Asp Gln Val Val Ala Leu Gly Arg Thr Val Thr Phe Gln Cys
            325                 330                 335

Glu Ala Thr Gly Asn Pro Gln Pro Ala Ile Phe Trp Arg Arg Glu Gly
            340                 345                 350

Ser Gln Asn Leu Leu Phe Ser Tyr Gln Pro Pro Gln Ser Ser Ser Arg
            355                 360                 365

Phe Ser Val Ser Gln Thr Gly Asp Leu Thr Ile Thr Asn Val Gln Arg
            370                 375                 380

Ser Asp Val Gly Tyr Tyr Ile Cys Gln Thr Leu Asn Val Ala Gly Ser
385                 390                 395                 400

Ile Ile Thr Lys Ala Tyr Leu Glu Val Thr Asp Val Ile Ala Asp Arg
            405                 410                 415

Pro Pro Pro Val Ile Arg Gln Gly Pro Val Asn Gln Thr Val Ala Val
            420                 425                 430

Asp Gly Thr Leu Val Leu Ser Cys Val Ala Thr Gly Ser Pro Val Pro
            435                 440                 445

Thr Ile Leu Trp Arg Lys Asp Gly Val Leu Val Ser Thr Gln Asp Ser
450                 455                 460

Arg Ile Lys Gln Leu Glu Thr Gly Val Leu Gln Ile Arg Tyr Ala Lys
465                 470                 475                 480

Leu Gly Asp Thr Gly Arg Tyr Thr Cys Ile Ala Ser Thr Pro Ser Gly
            485                 490                 495

Glu Ala Thr Trp Ser Ala Tyr Ile Glu Val Gln Glu Phe
            500                 505
```

<210> SEQ ID NO 3
<211> LENGTH: 225
<212> TYPE: PRT
<213> ORGANISM: Bos taurus

<400> SEQUENCE: 3

```
Met Ile Ala Glu Pro Ala His Phe Tyr Leu Phe Gly Leu Ile Cys Leu
1               5                   10                  15

Cys Ser Gly Ser Arg Leu Arg Gln Glu Asp Phe Pro Pro Arg Ile Val
            20                  25                  30

Glu His Pro Ser Asp Leu Ile Val Ser Lys Gly Glu Pro Ala Thr Leu
            35                  40                  45
```

```
Asn Cys Lys Ala Glu Gly Arg Pro Thr Pro Thr Ile Glu Trp Tyr Lys
    50                  55                  60

Gly Gly Glu Arg Val Glu Thr Asp Lys Asp Asp Pro Arg Ser His Arg
65                  70                  75                  80

Met Leu Leu Pro Ser Gly Ser Leu Phe Phe Leu Arg Ile Val His Gly
                85                  90                  95

Arg Lys Ser Arg Pro Asp Glu Gly Val Tyr Val Cys Val Ala Arg Asn
                100                 105                 110

Tyr Leu Gly Glu Ala Val Ser His Asn Ala Ser Leu Glu Val Ala Ile
                115                 120                 125

Leu Arg Asp Asp Phe Arg Gln Asn Pro Ser Asp Val Met Val Ala Val
    130                 135                 140

Gly Glu Pro Ala Val Met Glu Cys Gln Pro Pro Arg Gly His Pro Glu
145                 150                 155                 160

Pro Thr Ile Ser Trp Lys Lys Asp Gly Ser Pro Leu Asp Asp Lys Asp
                165                 170                 175

Glu Arg Ile Thr Ile Arg Gly Gly Lys Leu Met Ile Thr Tyr Thr Arg
                180                 185                 190

Lys Ser Asp Ala Gly Lys Tyr Val Cys Val Gly Thr Asn Met Val Gly
                195                 200                 205

Glu Arg Glu Ser Glu Val Ala Glu Leu Thr Val Leu Glu Arg Pro Ser
    210                 215                 220

Phe
225

<210> SEQ ID NO 4
<211> LENGTH: 832
<212> TYPE: PRT
<213> ORGANISM: Homo sapiens

<400> SEQUENCE: 4

Met Ile Ala Glu Pro Ala His Phe Tyr Leu Phe Gly Leu Ile Cys Leu
1               5                   10                  15

Cys Ser Gly Ser Arg Leu Arg Gln Glu Asp Phe Pro Pro Arg Ile Val
                20                  25                  30

Glu His Pro Ser Asp Leu Ile Val Ser Lys Gly Glu Pro Ala Thr Leu
                35                  40                  45

Asn Cys Lys Ala Glu Gly Arg Pro Thr Pro Thr Ile Glu Trp Tyr Lys
    50                  55                  60

Gly Gly Glu Arg Val Glu Thr Asp Lys Asp Asp Pro Arg Ser His Arg
65                  70                  75                  80

Met Leu Leu Pro Ser Gly Ser Leu Phe Phe Leu Arg Ile Val His Gly
                85                  90                  95

Arg Lys Ser Arg Pro Asp Glu Gly Val Tyr Val Cys Val Ala Arg Asn
                100                 105                 110

Tyr Leu Gly Glu Ala Val Ser His Asn Ala Ser Leu Glu Val Ala Ile
                115                 120                 125

Leu Arg Asp Asp Phe Arg Gln Asn Pro Ser Asp Val Met Val Ala Val
    130                 135                 140

Gly Glu Pro Ala Val Met Glu Cys Gln Pro Pro Arg Gly His Pro Glu
145                 150                 155                 160

Pro Thr Ile Ser Trp Lys Lys Asp Gly Ser Pro Leu Asp Asp Lys Asp
                165                 170                 175

Glu Arg Ile Thr Ile Arg Gly Gly Lys Leu Met Ile Thr Tyr Thr Arg
```

```
            180                 185                 190
Lys Ser Asp Ala Gly Lys Tyr Val Cys Val Gly Thr Asn Met Val Gly
            195                 200                 205
Glu Arg Glu Ser Glu Val Ala Glu Leu Thr Val Leu Glu Arg Pro Ser
            210                 215                 220
Phe Val Lys Arg Pro Ser Asn Leu Ala Val Thr Val Asp Asp Ser Ala
225                 230                 235                 240
Glu Phe Lys Cys Glu Ala Arg Gly Asp Pro Val Pro Thr Val Arg Trp
                245                 250                 255
Arg Lys Asp Asp Gly Glu Leu Pro Lys Ser Arg Tyr Glu Ile Arg Asp
                260                 265                 270
Asp His Thr Leu Lys Ile Arg Lys Val Thr Ala Gly Asp Met Gly Ser
            275                 280                 285
Tyr Thr Cys Val Ala Glu Asn Met Val Gly Lys Ala Glu Ala Ser Ala
            290                 295                 300
Thr Leu Thr Val Gln Val Gly Ser Glu Pro Pro His Phe Val Val Lys
305                 310                 315                 320
Pro Arg Asp Gln Val Val Ala Leu Gly Arg Thr Val Thr Phe Gln Cys
                325                 330                 335
Glu Ala Thr Gly Asn Pro Gln Pro Ala Ile Phe Trp Arg Arg Glu Gly
                340                 345                 350
Ser Gln Asn Leu Leu Phe Ser Tyr Gln Pro Pro Gln Ser Ser Ser Arg
            355                 360                 365
Phe Ser Val Ser Gln Thr Gly Asp Leu Thr Ile Thr Asn Val Gln Arg
            370                 375                 380
Ser Asp Val Gly Tyr Tyr Ile Cys Gln Thr Leu Asn Val Ala Gly Ser
385                 390                 395                 400
Ile Ile Thr Lys Ala Tyr Leu Glu Val Thr Asp Val Ile Ala Asp Arg
                405                 410                 415
Pro Pro Pro Val Ile Arg Gln Gly Pro Val Asn Gln Thr Val Ala Val
                420                 425                 430
Asp Gly Thr Phe Val Leu Ser Cys Val Ala Thr Gly Ser Pro Val Pro
            435                 440                 445
Thr Ile Leu Trp Arg Lys Asp Gly Val Leu Val Ser Thr Gln Asp Ser
450                 455                 460
Arg Ile Lys Gln Leu Glu Asn Gly Val Leu Gln Ile Arg Tyr Ala Lys
465                 470                 475                 480
Leu Gly Asp Thr Gly Arg Tyr Thr Cys Ile Ala Ser Thr Pro Ser Gly
                485                 490                 495
Glu Ala Thr Trp Ser Ala Tyr Ile Glu Val Gln Glu Phe Gly Val Pro
                500                 505                 510
Val Gln Pro Pro Arg Pro Thr Asp Pro Asn Leu Ile Pro Ser Ala Pro
            515                 520                 525
Ser Lys Pro Glu Val Thr Asp Val Ser Arg Asn Thr Val Thr Leu Ser
            530                 535                 540
Trp Gln Pro Asn Leu Asn Ser Gly Ala Thr Pro Thr Ser Tyr Ile Ile
545                 550                 555                 560
Glu Ala Phe Ser His Ala Ser Gly Ser Ser Trp Gln Thr Val Ala Glu
                565                 570                 575
Asn Val Lys Thr Glu Thr Ser Ala Ile Lys Gly Leu Lys Pro Asn Ala
            580                 585                 590
Ile Tyr Leu Phe Leu Val Arg Ala Ala Asn Ala Tyr Gly Ile Ser Asp
            595                 600                 605
```

```
Pro Ser Gln Ile Ser Asp Pro Val Lys Thr Gln Asp Val Leu Pro Thr
            610                 615                 620
Ser Gln Gly Val Asp His Lys Gln Val Gln Arg Glu Leu Gly Asn Ala
625                 630                 635                 640
Val Leu His Leu His Asn Pro Thr Val Leu Ser Ser Ser Ser Ile Glu
                645                 650                 655
Val His Trp Thr Val Asp Gln Gln Ser Gln Tyr Ile Gln Gly Tyr Lys
                660                 665                 670
Ile Leu Tyr Arg Pro Ser Gly Ala Asn His Gly Glu Ser Asp Trp Leu
            675                 680                 685
Val Phe Glu Val Arg Thr Pro Ala Lys Asn Ser Val Ile Pro Asp
690                 695                 700
Leu Arg Lys Gly Val Asn Tyr Glu Ile Lys Ala Arg Pro Phe Phe Asn
705                 710                 715                 720
Glu Phe Gln Gly Ala Asp Ser Glu Ile Lys Phe Ala Lys Thr Leu Glu
                725                 730                 735
Glu Ala Pro Ser Ala Pro Pro Gln Gly Val Thr Val Ser Lys Asn Asp
                740                 745                 750
Gly Asn Gly Thr Ala Ile Leu Val Ser Trp Gln Pro Pro Glu Asp
            755                 760                 765
Thr Gln Asn Gly Met Val Gln Glu Tyr Lys Val Trp Cys Leu Gly Asn
770                 775                 780
Glu Thr Arg Tyr His Ile Asn Lys Thr Val Asp Gly Ser Thr Phe Ser
785                 790                 795                 800
Val Val Ile Pro Phe Leu Val Pro Gly Ile Arg Tyr Ser Val Glu Val
                805                 810                 815
Ala Ala Ser Thr Gly Ala Gly Ser Gly Val Lys Ser Glu Pro Gln Phe
                820                 825                 830

<210> SEQ ID NO 5
<211> LENGTH: 509
<212> TYPE: PRT
<213> ORGANISM: Homo sapiens

<400> SEQUENCE: 5

Met Ile Ala Glu Pro Ala His Phe Tyr Leu Phe Gly Leu Ile Cys Leu
1               5                   10                  15
Cys Ser Gly Ser Arg Leu Arg Gln Glu Asp Phe Pro Arg Ile Val
                20                  25                  30
Glu His Pro Ser Asp Leu Ile Val Ser Lys Gly Glu Pro Ala Thr Leu
            35                  40                  45
Asn Cys Lys Ala Glu Gly Arg Pro Thr Pro Thr Ile Glu Trp Tyr Lys
50                  55                  60
Gly Gly Glu Arg Val Glu Thr Asp Lys Asp Asp Pro Arg Ser His Arg
65                  70                  75                  80
Met Leu Leu Pro Ser Gly Ser Leu Phe Phe Leu Arg Ile Val His Gly
                85                  90                  95
Arg Lys Ser Arg Pro Asp Glu Gly Val Tyr Val Cys Val Ala Arg Asn
                100                 105                 110
Tyr Leu Gly Glu Ala Val Ser His Asn Ala Ser Leu Glu Val Ala Ile
            115                 120                 125
Leu Arg Asp Asp Phe Arg Gln Asn Pro Ser Asp Val Met Val Ala Val
            130                 135                 140
Gly Glu Pro Ala Val Met Glu Cys Gln Pro Pro Arg Gly His Pro Glu
```

-continued

```
            145                 150                 155                 160
        Pro Thr Ile Ser Trp Lys Lys Asp Gly Ser Pro Leu Asp Asp Lys Asp
                        165                 170                 175
        Glu Arg Ile Thr Ile Arg Gly Gly Lys Leu Met Ile Thr Tyr Thr Arg
                        180                 185                 190
        Lys Ser Asp Ala Gly Lys Tyr Val Cys Val Gly Thr Asn Met Val Gly
                        195                 200                 205
        Glu Arg Glu Ser Glu Val Ala Glu Leu Thr Val Leu Glu Arg Pro Ser
                        210                 215                 220
        Phe Val Lys Arg Pro Ser Asn Leu Ala Val Thr Val Asp Asp Ser Ala
        225                 230                 235                 240
        Glu Phe Lys Cys Glu Ala Arg Gly Asp Pro Val Pro Thr Val Arg Trp
                        245                 250                 255
        Arg Lys Asp Asp Gly Glu Leu Pro Lys Ser Arg Tyr Glu Ile Arg Asp
                        260                 265                 270
        Asp His Thr Leu Lys Ile Arg Lys Val Thr Ala Gly Asp Met Gly Ser
                        275                 280                 285
        Tyr Thr Cys Val Ala Glu Asn Met Val Gly Lys Ala Glu Ser Ala
                        290                 295                 300
        Thr Leu Thr Val Gln Val Gly Ser Glu Pro Pro His Phe Val Val Lys
        305                 310                 315                 320
        Pro Arg Asp Gln Val Val Ala Leu Gly Arg Thr Val Thr Phe Gln Cys
                        325                 330                 335
        Glu Ala Thr Gly Asn Pro Gln Pro Ala Ile Phe Trp Arg Arg Glu Gly
                        340                 345                 350
        Ser Gln Asn Leu Leu Phe Ser Tyr Gln Pro Pro Gln Ser Ser Ser Arg
                        355                 360                 365
        Phe Ser Val Ser Gln Thr Gly Asp Leu Thr Ile Thr Asn Val Gln Arg
                        370                 375                 380
        Ser Asp Val Gly Tyr Tyr Ile Cys Gln Thr Leu Asn Val Ala Gly Ser
        385                 390                 395                 400
        Ile Ile Thr Lys Ala Tyr Leu Glu Val Thr Asp Val Ile Ala Asp Arg
                        405                 410                 415
        Pro Pro Pro Val Ile Arg Gln Gly Pro Val Asn Gln Thr Val Ala Val
                        420                 425                 430
        Asp Gly Thr Phe Val Leu Ser Cys Val Ala Thr Gly Ser Pro Val Pro
                        435                 440                 445
        Thr Ile Leu Trp Arg Lys Asp Gly Val Leu Val Ser Thr Gln Asp Ser
                        450                 455                 460
        Arg Ile Lys Gln Leu Glu Asn Gly Val Leu Gln Ile Arg Tyr Ala Lys
        465                 470                 475                 480
        Leu Gly Asp Thr Gly Arg Tyr Thr Cys Ile Ala Ser Thr Pro Ser Gly
                        485                 490                 495
        Glu Ala Thr Trp Ser Ala Tyr Ile Glu Val Gln Glu Phe
                        500                 505

<210> SEQ ID NO 6
<211> LENGTH: 225
<212> TYPE: PRT
<213> ORGANISM: Homo sapiens

<400> SEQUENCE: 6

Met Ile Ala Glu Pro Ala His Phe Tyr Leu Phe Gly Leu Ile Cys Leu
1               5                   10                  15
```

```
Cys Ser Gly Ser Arg Leu Arg Gln Glu Asp Phe Pro Arg Ile Val
            20                  25                  30

Glu His Pro Ser Asp Leu Ile Val Ser Lys Gly Glu Pro Ala Thr Leu
        35                  40                  45

Asn Cys Lys Ala Glu Gly Arg Pro Thr Pro Thr Ile Glu Trp Tyr Lys
 50                  55                  60

Gly Gly Glu Arg Val Glu Thr Asp Lys Asp Pro Arg Ser His Arg
 65                  70                  75                  80

Met Leu Leu Pro Ser Gly Ser Leu Phe Phe Leu Arg Ile Val His Gly
                85                  90                  95

Arg Lys Ser Arg Pro Asp Glu Gly Val Tyr Val Cys Val Ala Arg Asn
                100                 105                 110

Tyr Leu Gly Glu Ala Val Ser His Asn Ala Ser Leu Glu Val Ala Ile
            115                 120                 125

Leu Arg Asp Asp Phe Arg Gln Asn Pro Ser Asp Val Met Val Ala Val
        130                 135                 140

Gly Glu Pro Ala Val Met Glu Cys Gln Pro Pro Arg Gly His Pro Glu
145                 150                 155                 160

Pro Thr Ile Ser Trp Lys Lys Asp Gly Ser Pro Leu Asp Asp Lys Asp
                165                 170                 175

Glu Arg Ile Thr Ile Arg Gly Gly Lys Leu Met Ile Thr Tyr Thr Arg
                180                 185                 190

Lys Ser Asp Ala Gly Lys Tyr Val Cys Val Gly Thr Asn Met Val Gly
            195                 200                 205

Glu Arg Glu Ser Glu Val Ala Glu Leu Thr Val Leu Glu Arg Pro Ser
210                 215                 220

Phe
225

<210> SEQ ID NO 7
<211> LENGTH: 829
<212> TYPE: PRT
<213> ORGANISM: Bison bison

<400> SEQUENCE: 7

Met Ile Ala Glu Pro Ala Arg Phe Tyr Leu Phe Gly Leu Ile Cys Leu
1               5                   10                  15

Cys Ser Gly Ser Arg Leu Arg Gln Glu Asp Phe Pro Arg Ile Val
            20                  25                  30

Glu His Pro Ser Asp Leu Ile Val Ser Lys Gly Glu Pro Ala Thr Leu
        35                  40                  45

Asn Cys Lys Ala Glu Gly Arg Pro Thr Pro Thr Ile Glu Trp Tyr Lys
 50                  55                  60

Gly Gly Glu Arg Val Glu Thr Asp Lys Asp Pro Arg Ser His Arg
 65                  70                  75                  80

Met Leu Leu Pro Ser Gly Ser Leu Phe Phe Leu Arg Ile Val His Gly
                85                  90                  95

Arg Lys Ser Arg Pro Asp Glu Gly Val Tyr Ile Cys Val Ala Arg Asn
                100                 105                 110

Tyr Leu Gly Glu Ala Val Ser His Asn Ala Ser Leu Glu Val Ala Ile
            115                 120                 125

Leu Arg Asp Asp Phe Arg Gln Asn Pro Ser Asp Val Met Val Ala Val
        130                 135                 140

Gly Glu Pro Ala Val Met Glu Cys Gln Pro Pro Arg Gly His Pro Glu
145                 150                 155                 160
```

```
Pro Thr Ile Ser Trp Lys Lys Asp Gly Ser Pro Leu Asp Lys Asp
                165                 170                 175

Glu Arg Ile Thr Ile Arg Gly Gly Lys Leu Met Ile Thr Tyr Thr Arg
            180                 185                 190

Lys Ser Asp Ala Gly Lys Tyr Val Cys Val Gly Thr Asn Met Val Gly
        195                 200                 205

Glu Arg Glu Ser Glu Val Ala Glu Leu Thr Val Leu Glu Arg Pro Ser
    210                 215                 220

Phe Val Lys Arg Pro Ser Asn Leu Ala Val Thr Val Asp Asp Ser Ala
225                 230                 235                 240

Glu Phe Lys Cys Glu Ala Arg Gly Asp Pro Val Pro Thr Val Arg Trp
            245                 250                 255

Arg Lys Asp Asp Gly Glu Leu Pro Lys Ser Arg Tyr Glu Ile Arg Asp
        260                 265                 270

Asp His Thr Leu Lys Ile Arg Lys Val Thr Ala Gly Asp Met Gly Ser
    275                 280                 285

Tyr Thr Cys Val Ala Glu Asn Met Val Gly Lys Ala Glu Ala Ser Ala
290                 295                 300

Thr Leu Thr Val Gln Glu Pro Pro His Phe Val Val Lys Pro Arg Asp
305                 310                 315                 320

Gln Val Val Ala Leu Gly Arg Thr Val Thr Phe Gln Cys Glu Ala Thr
            325                 330                 335

Gly Asn Pro Gln Pro Ala Ile Phe Trp Arg Arg Glu Gly Ser Gln Asn
        340                 345                 350

Leu Leu Phe Ser Tyr Gln Pro Pro Gln Ser Ser Arg Phe Ser Val
    355                 360                 365

Ser Gln Thr Gly Asp Leu Thr Ile Thr Asn Val Gln Arg Ser Asp Val
370                 375                 380

Gly Tyr Tyr Ile Cys Gln Thr Leu Asn Val Ala Gly Ser Ile Ile Thr
385                 390                 395                 400

Lys Ala Tyr Leu Glu Val Thr Asp Val Ile Ala Asp Arg Pro Pro Pro
            405                 410                 415

Val Ile Arg Gln Gly Pro Val Asn Gln Thr Val Ala Val Asp Gly Thr
        420                 425                 430

Leu Ile Leu Ser Cys Val Ala Thr Gly Ser Pro Ala Pro Thr Ile Leu
    435                 440                 445

Trp Arg Lys Asp Gly Val Leu Val Ser Thr Gln Asp Ser Arg Ile Lys
450                 455                 460

Gln Leu Glu Ser Gly Val Leu Gln Ile Arg Tyr Ala Lys Leu Gly Asp
465                 470                 475                 480

Thr Gly Arg Tyr Thr Cys Thr Ala Ser Thr Pro Ser Gly Glu Ala Thr
            485                 490                 495

Trp Ser Ala Tyr Ile Glu Val Gln Glu Phe Gly Val Pro Val Gln Pro
        500                 505                 510

Pro Arg Pro Thr Asp Pro Asn Leu Ile Pro Ser Ala Pro Ser Lys Pro
    515                 520                 525

Glu Val Thr Asp Val Ser Lys Asn Thr Val Thr Leu Ser Trp Gln Pro
530                 535                 540

Asn Leu Asn Ser Gly Ala Thr Pro Thr Ser Tyr Ile Ile Glu Ala Phe
545                 550                 555                 560

Ser His Ala Ser Gly Ser Ser Trp Gln Thr Ala Ala Glu Asn Val Lys
            565                 570                 575
```

```
Thr Glu Thr Phe Ala Ile Lys Gly Leu Lys Pro Asn Ala Ile Tyr Leu
            580                 585                 590

Phe Leu Val Arg Ala Ala Asn Ala Tyr Gly Ile Ser Asp Pro Ser Gln
            595                 600                 605

Ile Ser Asp Pro Val Lys Thr Gln Asp Val Pro Pro Thr Ser Gln Gly
        610                 615                 620

Val Asp His Lys Gln Val Gln Arg Glu Leu Gly Asn Val Val Leu His
625                 630                 635                 640

Leu His Asn Pro Thr Ile Leu Ser Ser Ser Val Glu Val His Trp
            645                 650                 655

Thr Val Asp Gln Gln Ser Gln Tyr Ile Gln Gly Tyr Lys Ile Leu Tyr
            660                 665                 670

Arg Pro Ser Gly Ala Ser His Gly Glu Ser Glu Trp Leu Val Phe Glu
            675                 680                 685

Val Arg Thr Pro Thr Lys Asn Ser Val Val Ile Pro Asp Leu Arg Lys
            690                 695                 700

Gly Val Asn Tyr Glu Ile Lys Ala Arg Pro Phe Phe Asn Glu Phe Gln
705                 710                 715                 720

Gly Ala Asp Ser Glu Ile Lys Phe Ala Lys Thr Leu Glu Glu Ala Pro
                725                 730                 735

Ser Ala Pro Pro Arg Ser Val Thr Val Ser Lys Asn Asp Gly Asn Gly
            740                 745                 750

Thr Ala Ile Leu Val Thr Trp Gln Pro Pro Glu Asp Thr Gln Asn
            755                 760                 765

Gly Met Val Gln Glu Tyr Lys Val Trp Cys Leu Gly Asn Glu Thr Lys
770                 775                 780

Tyr His Ile Asn Lys Thr Val Asp Gly Ser Thr Phe Ser Val Val Ile
785                 790                 795                 800

Pro Ser Leu Val Pro Gly Ile Arg Tyr Ser Val Glu Val Ala Ala Ser
                805                 810                 815

Thr Gly Ala Gly Pro Gly Val Lys Ser Glu Pro Gln Phe
            820                 825

<210> SEQ ID NO 8
<211> LENGTH: 506
<212> TYPE: PRT
<213> ORGANISM: Bison bison

<400> SEQUENCE: 8

Met Ile Ala Glu Pro Ala Arg Phe Tyr Leu Phe Gly Leu Ile Cys Leu
1               5                   10                  15

Cys Ser Gly Ser Arg Leu Arg Gln Glu Asp Phe Pro Pro Arg Ile Val
            20                  25                  30

Glu His Pro Ser Asp Leu Ile Val Ser Lys Gly Glu Pro Ala Thr Leu
        35                  40                  45

Asn Cys Lys Ala Glu Gly Arg Pro Thr Pro Thr Ile Glu Trp Tyr Lys
    50                  55                  60

Gly Gly Glu Arg Val Glu Thr Asp Lys Asp Asp Pro Arg Ser His Arg
65                  70                  75                  80

Met Leu Leu Pro Ser Gly Ser Leu Phe Phe Leu Arg Ile Val His Gly
                85                  90                  95

Arg Lys Ser Arg Pro Asp Glu Gly Val Tyr Ile Cys Val Ala Arg Asn
            100                 105                 110

Tyr Leu Gly Glu Ala Val Ser His Asn Ala Ser Leu Glu Val Ala Ile
        115                 120                 125
```

Leu Arg Asp Asp Phe Arg Gln Asn Pro Ser Asp Val Met Val Ala Val
130                 135                 140

Gly Glu Pro Ala Val Met Glu Cys Gln Pro Arg Gly His Pro Glu
145                 150                 155                 160

Pro Thr Ile Ser Trp Lys Lys Asp Gly Ser Pro Leu Asp Asp Lys Asp
                165                 170                 175

Glu Arg Ile Thr Ile Arg Gly Gly Lys Leu Met Ile Thr Tyr Thr Arg
                180                 185                 190

Lys Ser Asp Ala Gly Lys Tyr Val Cys Val Gly Thr Asn Met Val Gly
                195                 200                 205

Glu Arg Glu Ser Glu Val Ala Glu Leu Thr Val Leu Glu Arg Pro Ser
210                 215                 220

Phe Val Lys Arg Pro Ser Asn Leu Ala Val Thr Val Asp Asp Ser Ala
225                 230                 235                 240

Glu Phe Lys Cys Glu Ala Arg Gly Asp Pro Val Pro Thr Val Arg Trp
                245                 250                 255

Arg Lys Asp Asp Gly Glu Leu Pro Lys Ser Arg Tyr Glu Ile Arg Asp
                260                 265                 270

Asp His Thr Leu Lys Ile Arg Lys Val Thr Ala Gly Asp Met Gly Ser
                275                 280                 285

Tyr Thr Cys Val Ala Glu Asn Met Val Gly Lys Ala Glu Ala Ser Ala
290                 295                 300

Thr Leu Thr Val Gln Glu Pro Pro His Phe Val Val Lys Pro Arg Asp
305                 310                 315                 320

Gln Val Val Ala Leu Gly Arg Thr Val Thr Phe Gln Cys Glu Ala Thr
                325                 330                 335

Gly Asn Pro Gln Pro Ala Ile Phe Trp Arg Arg Glu Gly Ser Gln Asn
                340                 345                 350

Leu Leu Phe Ser Tyr Gln Pro Pro Gln Ser Ser Ser Arg Phe Ser Val
                355                 360                 365

Ser Gln Thr Gly Asp Leu Thr Ile Thr Asn Val Gln Arg Ser Asp Val
370                 375                 380

Gly Tyr Tyr Ile Cys Gln Thr Leu Asn Val Ala Gly Ser Ile Ile Thr
385                 390                 395                 400

Lys Ala Tyr Leu Glu Val Thr Asp Val Ile Ala Asp Arg Pro Pro Pro
                405                 410                 415

Val Ile Arg Gln Gly Pro Val Asn Gln Thr Val Ala Val Asp Gly Thr
                420                 425                 430

Leu Ile Leu Ser Cys Val Ala Thr Gly Ser Pro Ala Pro Thr Ile Leu
                435                 440                 445

Trp Arg Lys Asp Gly Val Leu Val Ser Thr Gln Asp Ser Arg Ile Lys
450                 455                 460

Gln Leu Glu Ser Gly Val Leu Gln Ile Arg Tyr Ala Lys Leu Gly Asp
465                 470                 475                 480

Thr Gly Arg Tyr Thr Cys Thr Ala Ser Thr Pro Ser Gly Glu Ala Thr
                485                 490                 495

Trp Ser Ala Tyr Ile Glu Val Gln Glu Phe
                500                 505

<210> SEQ ID NO 9
<211> LENGTH: 225
<212> TYPE: PRT
<213> ORGANISM: Bison bison

```
<400> SEQUENCE: 9

Met Ile Ala Glu Pro Ala Arg Phe Tyr Leu Phe Gly Leu Ile Cys Leu
1               5                   10                  15

Cys Ser Gly Ser Arg Leu Arg Gln Glu Asp Phe Pro Pro Arg Ile Val
            20                  25                  30

Glu His Pro Ser Asp Leu Ile Val Ser Lys Gly Glu Pro Ala Thr Leu
        35                  40                  45

Asn Cys Lys Ala Glu Gly Arg Pro Thr Pro Thr Ile Glu Trp Tyr Lys
    50                  55                  60

Gly Gly Glu Arg Val Glu Thr Asp Lys Asp Pro Arg Ser His Arg
65                  70                  75                  80

Met Leu Leu Pro Ser Gly Ser Leu Phe Phe Leu Arg Ile Val His Gly
                85                  90                  95

Arg Lys Ser Arg Pro Asp Glu Gly Val Tyr Ile Cys Val Ala Arg Asn
            100                 105                 110

Tyr Leu Gly Glu Ala Val Ser His Asn Ala Ser Leu Glu Val Ala Ile
        115                 120                 125

Leu Arg Asp Asp Phe Arg Gln Asn Pro Ser Asp Val Met Val Ala Val
    130                 135                 140

Gly Glu Pro Ala Val Met Glu Cys Gln Pro Pro Arg Gly His Pro Glu
145                 150                 155                 160

Pro Thr Ile Ser Trp Lys Lys Asp Gly Ser Pro Leu Asp Asp Lys Asp
                165                 170                 175

Glu Arg Ile Thr Ile Arg Gly Gly Lys Leu Met Ile Thr Tyr Thr Arg
            180                 185                 190

Lys Ser Asp Ala Gly Lys Tyr Val Cys Val Gly Thr Asn Met Val Gly
        195                 200                 205

Glu Arg Glu Ser Glu Val Ala Glu Leu Thr Val Leu Glu Arg Pro Ser
    210                 215                 220

Phe
225

<210> SEQ ID NO 10
<211> LENGTH: 832
<212> TYPE: PRT
<213> ORGANISM: Camelus bactrianus

<400> SEQUENCE: 10

Met Ile Ala Glu Pro Ala His Phe Tyr Leu Phe Gly Leu Ile Cys Leu
1               5                   10                  15

Cys Ser Gly Ser Arg Leu Arg Gln Glu Asp Phe Pro Pro Arg Ile Val
            20                  25                  30

Glu His Pro Ser Asp Leu Ile Val Ser Lys Gly Glu Pro Ala Thr Leu
        35                  40                  45

Asn Cys Lys Ala Glu Gly Arg Pro Thr Pro Thr Ile Glu Trp Tyr Lys
    50                  55                  60

Gly Gly Glu Arg Val Glu Thr Asp Lys Asp Pro Arg Ser His Arg
65                  70                  75                  80

Met Leu Leu Pro Ser Gly Ser Leu Phe Phe Leu Arg Ile Val His Gly
                85                  90                  95

Arg Lys Ser Arg Pro Asp Glu Gly Val Tyr Val Cys Val Ala Arg Asn
            100                 105                 110

Tyr Leu Gly Glu Ala Val Ser His Asn Ala Ser Leu Glu Val Ala Ile
        115                 120                 125
```

-continued

```
Leu Arg Asp Asp Phe Arg Gln Asn Pro Ser Asp Val Met Val Ala Val
    130                 135                 140
Gly Glu Pro Ala Val Met Glu Cys Gln Pro Pro Arg Gly His Pro Glu
145                 150                 155                 160
Pro Thr Ile Ser Trp Lys Lys Asp Gly Ser Ser Leu Asp Asp Lys Asp
                165                 170                 175
Glu Arg Ile Thr Ile Arg Gly Gly Lys Leu Met Ile Thr Tyr Thr Arg
            180                 185                 190
Lys Ser Asp Ala Gly Lys Tyr Val Cys Val Gly Thr Asn Met Val Gly
        195                 200                 205
Glu Arg Glu Ser Glu Val Ala Glu Leu Thr Val Leu Glu Arg Pro Ser
    210                 215                 220
Phe Val Lys Arg Pro Ser Asn Leu Ala Val Thr Val Asp Asp Ser Ala
225                 230                 235                 240
Glu Phe Lys Cys Glu Ala Arg Gly Asp Pro Val Pro Thr Val Arg Trp
                245                 250                 255
Arg Lys Asp Asp Gly Glu Leu Pro Lys Ser Arg Tyr Glu Ile Arg Asp
            260                 265                 270
Asp His Thr Leu Lys Ile Arg Lys Val Met Ala Ser Asp Met Gly Ser
        275                 280                 285
Tyr Thr Cys Val Ala Glu Asn Met Val Gly Lys Ala Glu Ala Ser Ala
    290                 295                 300
Thr Leu Thr Val Gln Val Gly Ser Glu Pro Pro His Phe Val Val Lys
305                 310                 315                 320
Pro Arg Asp Gln Val Val Ala Leu Gly Arg Thr Val Thr Phe Gln Cys
                325                 330                 335
Glu Ala Thr Gly Asn Pro Gln Pro Ala Ile Phe Trp Arg Arg Glu Gly
            340                 345                 350
Ser Gln Asn Leu Leu Phe Ser Tyr Gln Pro Pro Gln Ser Ser Ser Arg
        355                 360                 365
Phe Ser Val Ser Gln Thr Gly Asp Leu Thr Ile Thr Asn Val Gln Arg
    370                 375                 380
Ser Asp Val Gly Tyr Tyr Ile Cys Gln Thr Leu Asn Val Ala Gly Ser
385                 390                 395                 400
Ile Ile Thr Lys Ala Tyr Leu Glu Val Thr Asp Val Ile Ala Asp Arg
                405                 410                 415
Pro Pro Pro Val Ile Arg Gln Gly Pro Val Asn Gln Thr Val Ala Val
            420                 425                 430
Asp Gly Thr Leu Val Leu Ser Cys Val Ala Thr Gly Ser Pro Val Pro
        435                 440                 445
Thr Ile Leu Trp Arg Lys Asp Gly Val Leu Val Ser Thr Gln Asp Ser
    450                 455                 460
Arg Ile Lys Gln Leu Glu Thr Gly Val Leu Gln Ile Arg Tyr Ala Lys
465                 470                 475                 480
Leu Gly Asp Thr Gly Arg Tyr Thr Cys Ile Ala Ser Thr Pro Ser Gly
                485                 490                 495
Glu Ala Thr Trp Ser Ala Tyr Ile Glu Val Gln Glu Phe Gly Val Pro
            500                 505                 510
Val Gln Pro Pro Arg Pro Thr Asp Pro Asn Leu Ile Pro Ser Ala Pro
        515                 520                 525
Ser Lys Pro Glu Val Thr Asp Val Ser Arg Asn Thr Val Thr Leu Ser
    530                 535                 540
Trp Gln Pro Asn Leu Asn Ser Gly Ala Thr Pro Thr Ser Tyr Ile Ile
```

-continued

```
                545                 550                 555                 560
            Glu Ala Phe Ser His Ala Ser Gly Ser Ser Trp Gln Thr Val Ala Glu
                            565                 570                 575

Asn Val Lys Met Glu Thr Phe Ala Val Lys Gly Leu Lys Pro Asn Ala
                        580                 585                 590

Ile Tyr Leu Phe Leu Val Arg Ala Ala Asn Ala Tyr Gly Ile Ser Asp
                    595                 600                 605

Pro Ser Gln Ile Ser Asp Pro Val Lys Thr Gln Asp Val Pro Pro Thr
                610                 615                 620

Ser Gln Gly Val Asp His Lys Gln Val Gln Arg Glu Leu Gly Asn Val
            625                 630                 635                 640

Val Leu His Leu His Asn Pro Thr Ile Leu Ser Ser Ser Ile Glu
                            645                 650                 655

Val His Trp Thr Val Asp Gln Gln Ser Gln Tyr Ile Gln Gly Tyr Lys
                        660                 665                 670

Ile Leu Tyr Arg Pro Ser Gly Ala Asn His Gly Glu Ser Gly Trp Leu
                    675                 680                 685

Val Phe Glu Val Arg Thr Pro Thr Lys Asn Ser Val Val Ile Pro Asp
                690                 695                 700

Leu Lys Lys Gly Val Asn Tyr Glu Ile Lys Ala Arg Pro Phe Phe Asn
            705                 710                 715                 720

Glu Phe Gln Gly Ala Asp Ser Glu Ile Lys Phe Ala Lys Thr Leu Glu
                            725                 730                 735

Glu Ala Pro Ser Ala Pro Gln Ser Val Thr Val Ser Lys Asn Asp
                        740                 745                 750

Gly Asn Gly Thr Ala Ile Leu Val Ser Trp Gln Pro Pro Glu Asp
                    755                 760                 765

Thr Gln Asn Gly Met Val Gln Glu Tyr Lys Val Trp Cys Leu Gly Asn
                770                 775                 780

Glu Thr Arg Tyr His Ile Asn Lys Thr Val Asp Gly Ser Thr Phe Ser
            785                 790                 795                 800

Val Val Ile Pro Ser Leu Val Pro Gly Ile Arg Tyr Ser Val Glu Val
                            805                 810                 815

Ala Ala Ser Thr Gly Ala Gly Ser Gly Val Lys Ser Glu Pro Gln Phe
                        820                 825                 830

<210> SEQ ID NO 11
<211> LENGTH: 509
<212> TYPE: PRT
<213> ORGANISM: Camelus bactrianus

<400> SEQUENCE: 11

Met Ile Ala Glu Pro Ala His Phe Tyr Leu Phe Gly Leu Ile Cys Leu
1               5                   10                  15

Cys Ser Gly Ser Arg Leu Arg Gln Glu Asp Phe Pro Pro Arg Ile Val
            20                  25                  30

Glu His Pro Ser Asp Leu Ile Val Ser Lys Gly Glu Pro Ala Thr Leu
        35                  40                  45

Asn Cys Lys Ala Glu Gly Arg Pro Thr Pro Thr Ile Glu Trp Tyr Lys
    50                  55                  60

Gly Gly Glu Arg Val Glu Thr Asp Lys Asp Asp Pro Arg Ser His Arg
65                  70                  75                  80

Met Leu Leu Pro Ser Gly Ser Leu Phe Phe Leu Arg Ile Val His Gly
                85                  90                  95
```

-continued

```
Arg Lys Ser Arg Pro Asp Glu Gly Val Tyr Val Cys Val Ala Arg Asn
            100                 105                 110
Tyr Leu Gly Glu Ala Val Ser His Asn Ala Ser Leu Glu Val Ala Ile
        115                 120                 125
Leu Arg Asp Asp Phe Arg Gln Asn Pro Ser Asp Val Met Val Ala Val
    130                 135                 140
Gly Glu Pro Ala Val Met Glu Cys Gln Pro Pro Arg Gly His Pro Glu
145                 150                 155                 160
Pro Thr Ile Ser Trp Lys Lys Asp Gly Ser Ser Leu Asp Asp Lys Asp
                165                 170                 175
Glu Arg Ile Thr Ile Arg Gly Gly Lys Leu Met Ile Thr Tyr Thr Arg
            180                 185                 190
Lys Ser Asp Ala Gly Lys Tyr Val Cys Val Gly Thr Asn Met Val Gly
        195                 200                 205
Glu Arg Glu Ser Glu Val Ala Glu Leu Thr Val Leu Glu Arg Pro Ser
    210                 215                 220
Phe Val Lys Arg Pro Ser Asn Leu Ala Val Thr Val Asp Asp Ser Ala
225                 230                 235                 240
Glu Phe Lys Cys Glu Ala Arg Gly Asp Pro Val Pro Thr Val Arg Trp
                245                 250                 255
Arg Lys Asp Asp Gly Glu Leu Pro Lys Ser Arg Tyr Glu Ile Arg Asp
            260                 265                 270
Asp His Thr Leu Lys Ile Arg Lys Val Met Ala Ser Asp Met Gly Ser
        275                 280                 285
Tyr Thr Cys Val Ala Glu Asn Met Val Gly Lys Ala Glu Ala Ser Ala
    290                 295                 300
Thr Leu Thr Val Gln Val Gly Ser Glu Pro Pro His Phe Val Val Lys
305                 310                 315                 320
Pro Arg Asp Gln Val Val Ala Leu Gly Arg Thr Val Thr Phe Gln Cys
                325                 330                 335
Glu Ala Thr Gly Asn Pro Gln Pro Ala Ile Phe Trp Arg Arg Glu Gly
            340                 345                 350
Ser Gln Asn Leu Leu Phe Ser Tyr Gln Pro Pro Gln Ser Ser Ser Arg
        355                 360                 365
Phe Ser Val Ser Gln Thr Gly Asp Leu Thr Ile Thr Asn Val Gln Arg
    370                 375                 380
Ser Asp Val Gly Tyr Tyr Ile Cys Gln Thr Leu Asn Val Ala Gly Ser
385                 390                 395                 400
Ile Ile Thr Lys Ala Tyr Leu Glu Val Thr Asp Val Ile Ala Asp Arg
                405                 410                 415
Pro Pro Pro Val Ile Arg Gln Gly Pro Val Asn Gln Thr Val Ala Val
            420                 425                 430
Asp Gly Thr Leu Val Leu Ser Cys Val Ala Thr Gly Ser Pro Val Pro
        435                 440                 445
Thr Ile Leu Trp Arg Lys Asp Gly Val Leu Val Ser Thr Gln Asp Ser
    450                 455                 460
Arg Ile Lys Gln Leu Glu Thr Gly Val Leu Gln Ile Arg Tyr Ala Lys
465                 470                 475                 480
Leu Gly Asp Thr Gly Arg Tyr Thr Cys Ile Ala Ser Thr Pro Ser Gly
                485                 490                 495
Glu Ala Thr Trp Ser Ala Tyr Ile Glu Val Gln Glu Phe
            500                 505
```

<210> SEQ ID NO 12
<211> LENGTH: 225
<212> TYPE: PRT
<213> ORGANISM: Camelus bactrianus

<400> SEQUENCE: 12

```
Met Ile Ala Glu Pro Ala His Phe Tyr Leu Phe Gly Leu Ile Cys Leu
1               5                   10                  15

Cys Ser Gly Ser Arg Leu Arg Gln Glu Asp Phe Pro Pro Arg Ile Val
            20                  25                  30

Glu His Pro Ser Asp Leu Ile Val Ser Lys Gly Glu Pro Ala Thr Leu
        35                  40                  45

Asn Cys Lys Ala Glu Gly Arg Pro Thr Pro Thr Ile Glu Trp Tyr Lys
    50                  55                  60

Gly Gly Glu Arg Val Glu Thr Asp Lys Asp Asp Pro Arg Ser His Arg
65                  70                  75                  80

Met Leu Leu Pro Ser Gly Ser Leu Phe Phe Leu Arg Ile Val His Gly
                85                  90                  95

Arg Lys Ser Arg Pro Asp Glu Gly Val Tyr Val Cys Val Ala Arg Asn
            100                 105                 110

Tyr Leu Gly Glu Ala Val Ser His Asn Ala Ser Leu Glu Val Ala Ile
        115                 120                 125

Leu Arg Asp Asp Phe Arg Gln Asn Pro Ser Asp Val Met Val Ala Val
    130                 135                 140

Gly Glu Pro Ala Val Met Glu Cys Gln Pro Pro Arg Gly His Pro Glu
145                 150                 155                 160

Pro Thr Ile Ser Trp Lys Lys Asp Gly Ser Ser Leu Asp Asp Lys Asp
                165                 170                 175

Glu Arg Ile Thr Ile Arg Gly Gly Lys Leu Met Ile Thr Tyr Thr Arg
            180                 185                 190

Lys Ser Asp Ala Gly Lys Tyr Val Cys Val Gly Thr Asn Met Val Gly
        195                 200                 205

Glu Arg Glu Ser Glu Val Ala Glu Leu Thr Val Leu Glu Arg Pro Ser
    210                 215                 220

Phe
225
```

<210> SEQ ID NO 13
<211> LENGTH: 832
<212> TYPE: PRT
<213> ORGANISM: Capra hircus

<400> SEQUENCE: 13

```
Met Ile Ala Glu Pro Ala His Phe Tyr Leu Phe Gly Phe Ile Cys Leu
1               5                   10                  15

Cys Ser Gly Ser Arg Leu Arg Gln Glu Asp Phe Pro Pro Arg Ile Val
            20                  25                  30

Glu His Pro Ser Asp Leu Ile Val Ser Lys Gly Glu Pro Ala Thr Leu
        35                  40                  45

Asn Cys Lys Ala Glu Gly Arg Pro Thr Pro Thr Ile Glu Trp Tyr Lys
    50                  55                  60

Gly Gly Glu Arg Val Glu Thr Asp Lys Asp Asp Pro Arg Ser His Arg
65                  70                  75                  80

Met Leu Leu Pro Ser Gly Ser Leu Phe Phe Leu Arg Ile Val His Gly
                85                  90                  95

Arg Lys Ser Arg Pro Asp Glu Gly Val Tyr Val Cys Val Ala Arg Asn
```

```
                100                 105                 110
Tyr Leu Gly Glu Ala Val Ser His Asn Ala Ser Leu Glu Val Ala Ile
            115                 120                 125
Leu Arg Asp Asp Phe Arg Gln Asn Pro Ser Asp Val Met Val Ala Val
        130                 135                 140
Gly Glu Pro Ala Val Met Glu Cys Gln Pro Pro Arg Gly His Pro Glu
145                 150                 155                 160
Pro Thr Ile Ser Trp Lys Lys Asp Gly Ser Pro Leu Asp Asp Lys Asp
                165                 170                 175
Glu Arg Ile Thr Ile Arg Gly Gly Lys Leu Met Ile Thr Tyr Thr Arg
            180                 185                 190
Lys Ser Asp Ala Gly Lys Tyr Val Cys Val Gly Thr Asn Met Val Gly
        195                 200                 205
Glu Arg Glu Ser Glu Val Ala Glu Leu Thr Val Leu Glu Arg Pro Ser
210                 215                 220
Phe Val Lys Arg Pro Ser Asn Leu Ala Val Thr Val Asp Asp Ser Ala
225                 230                 235                 240
Glu Phe Lys Cys Glu Ala Arg Gly Asp Pro Val Pro Thr Val Arg Trp
                245                 250                 255
Arg Lys Asp Asp Gly Glu Leu Pro Lys Ser Arg Tyr Glu Ile Arg Asp
            260                 265                 270
Asp His Thr Leu Lys Ile Arg Lys Val Thr Ala Gly Asp Met Gly Ser
        275                 280                 285
Tyr Thr Cys Val Ala Glu Asn Met Val Gly Lys Ala Glu Ala Ser Ala
        290                 295                 300
Thr Leu Thr Val Gln Val Gly Ser Glu Pro Pro His Phe Val Val Lys
305                 310                 315                 320
Pro Arg Asp Gln Val Val Ala Leu Gly Arg Thr Val Thr Phe Gln Cys
                325                 330                 335
Glu Ala Thr Gly Asn Pro Gln Pro Ala Ile Phe Trp Arg Arg Glu Gly
            340                 345                 350
Ser Gln Asn Leu Leu Phe Ser Tyr Gln Pro Pro Gln Ser Ser Ser Arg
        355                 360                 365
Phe Ser Val Ser Gln Thr Gly Asp Leu Thr Ile Thr Asn Val Gln Arg
370                 375                 380
Ser Asp Val Gly Tyr Tyr Ile Cys Gln Thr Leu Asn Val Ala Gly Ser
385                 390                 395                 400
Ile Ile Thr Lys Ala Tyr Leu Glu Val Thr Asp Val Ile Ala Asp Arg
                405                 410                 415
Pro Pro Pro Val Ile Arg Gln Gly Pro Val Asn Gln Thr Val Ala Val
            420                 425                 430
Asp Gly Thr Leu Val Leu Ser Cys Val Ala Thr Gly Ser Pro Val Pro
        435                 440                 445
Thr Ile Leu Trp Arg Lys Asp Gly Val Leu Val Ser Thr Gln Asp Ser
450                 455                 460
Arg Ile Lys Gln Leu Glu Thr Gly Val Leu Gln Ile Arg Tyr Ala Lys
465                 470                 475                 480
Leu Gly Asp Thr Gly Arg Tyr Thr Cys Ile Ala Ser Thr Pro Ser Gly
                485                 490                 495
Glu Ala Thr Trp Ser Ala Tyr Ile Glu Val Gln Glu Phe Gly Val Pro
            500                 505                 510
Val Gln Pro Pro Arg Pro Thr Asp Pro Asn Leu Ile Pro Ser Ala Pro
        515                 520                 525
```

```
Ser Lys Pro Glu Val Thr Asp Val Ser Arg Asn Thr Val Thr Leu Ser
    530                 535                 540

Trp Gln Pro Asn Leu Asn Ser Gly Ala Thr Pro Thr Ser Tyr Ile Ile
545                 550                 555                 560

Glu Ala Phe Ser His Ala Ser Gly Ser Ser Trp Gln Thr Val Ala Glu
                565                 570                 575

Asn Val Lys Thr Glu Thr Phe Ala Ile Lys Gly Leu Lys Pro Asn Ala
            580                 585                 590

Ile Tyr Leu Phe Leu Val Arg Ala Ala Asn Ala Tyr Gly Ile Ser Asp
        595                 600                 605

Pro Ser Gln Ile Ser Asp Pro Val Lys Thr Gln Asp Ile Pro Pro Thr
    610                 615                 620

Ser Gln Gly Val Asp His Lys Gln Val Gln Arg Glu Leu Gly Asn Val
625                 630                 635                 640

Val Leu His Leu His Asn Pro Thr Ile Leu Ser Ser Ser Ile Glu
                645                 650                 655

Val His Trp Thr Val Asp Gln Gln Ser Gln Tyr Ile Gln Gly Tyr Lys
            660                 665                 670

Val Leu Tyr Arg Pro Ser Gly Ala Asn His Gly Glu Ser Glu Trp Leu
        675                 680                 685

Val Phe Glu Val Arg Thr Pro Thr Lys Asn Ser Val Val Ile Pro Asp
    690                 695                 700

Leu Lys Lys Gly Val Asn Tyr Glu Ile Lys Ala Arg Pro Phe Phe Asn
705                 710                 715                 720

Glu Phe Gln Gly Ala Asp Ser Glu Ile Lys Phe Ala Lys Thr Leu Glu
                725                 730                 735

Glu Ala Pro Ser Ala Pro Pro Gln Ser Val Thr Val Ser Lys Asn Asp
            740                 745                 750

Gly Asn Gly Thr Ala Ile Leu Val Ser Trp Gln Pro Pro Glu Asp
        755                 760                 765

Thr Gln Asn Gly Met Val Gln Glu Tyr Lys Val Trp Cys Leu Gly Asn
    770                 775                 780

Glu Thr Arg Tyr His Ile Asn Lys Thr Val Asp Gly Ser Thr Phe Ser
785                 790                 795                 800

Val Val Ile Pro Ser Leu Val Pro Gly Ile Arg Tyr Ser Val Glu Val
                805                 810                 815

Ala Ala Ser Thr Gly Ala Gly Ser Gly Val Lys Ser Glu Pro Gln Phe
            820                 825                 830

<210> SEQ ID NO 14
<211> LENGTH: 509
<212> TYPE: PRT
<213> ORGANISM: Capra hircus

<400> SEQUENCE: 14

Met Ile Ala Glu Pro Ala His Phe Tyr Leu Phe Gly Phe Ile Cys Leu
1               5                   10                  15

Cys Ser Gly Ser Arg Leu Arg Gln Glu Asp Phe Pro Pro Arg Ile Val
            20                  25                  30

Glu His Pro Ser Asp Leu Ile Val Ser Lys Gly Glu Pro Ala Thr Leu
        35                  40                  45

Asn Cys Lys Ala Glu Gly Arg Pro Thr Pro Thr Ile Glu Trp Tyr Lys
    50                  55                  60

Gly Gly Glu Arg Val Glu Thr Asp Lys Asp Asp Pro Arg Ser His Arg
```

```
                65                  70                  75                  80
        Met Leu Leu Pro Ser Gly Ser Leu Phe Phe Leu Arg Ile Val His Gly
                        85                  90                  95

Arg Lys Ser Arg Pro Asp Glu Gly Val Tyr Val Cys Val Ala Arg Asn
                        100                 105                 110

Tyr Leu Gly Glu Ala Val Ser His Asn Ala Ser Leu Glu Val Ala Ile
                        115                 120                 125

Leu Arg Asp Asp Phe Arg Gln Asn Pro Ser Asp Val Met Val Ala Val
                        130                 135                 140

Gly Glu Pro Ala Val Met Glu Cys Gln Pro Arg Gly His Pro Glu
        145                 150                 155                 160

Pro Thr Ile Ser Trp Lys Lys Asp Gly Ser Pro Leu Asp Asp Lys Asp
                        165                 170                 175

Glu Arg Ile Thr Ile Arg Gly Gly Lys Leu Met Ile Thr Tyr Thr Arg
                        180                 185                 190

Lys Ser Asp Ala Gly Lys Tyr Val Cys Val Gly Thr Asn Met Val Gly
                        195                 200                 205

Glu Arg Glu Ser Glu Val Ala Glu Leu Thr Val Leu Glu Arg Pro Ser
                        210                 215                 220

Phe Val Lys Arg Pro Ser Asn Leu Ala Val Thr Val Asp Asp Ser Ala
        225                 230                 235                 240

Glu Phe Lys Cys Glu Ala Arg Gly Asp Pro Val Pro Thr Val Arg Trp
                        245                 250                 255

Arg Lys Asp Asp Gly Glu Leu Pro Lys Ser Arg Tyr Glu Ile Arg Asp
                        260                 265                 270

Asp His Thr Leu Lys Ile Arg Lys Val Thr Ala Gly Asp Met Gly Ser
                        275                 280                 285

Tyr Thr Cys Val Ala Glu Asn Met Val Gly Lys Ala Glu Ala Ser Ala
                        290                 295                 300

Thr Leu Thr Val Gln Val Gly Ser Glu Pro Pro His Phe Val Val Lys
        305                 310                 315                 320

Pro Arg Asp Gln Val Val Ala Leu Gly Arg Thr Val Thr Phe Gln Cys
                        325                 330                 335

Glu Ala Thr Gly Asn Pro Gln Pro Ala Ile Phe Trp Arg Arg Glu Gly
                        340                 345                 350

Ser Gln Asn Leu Leu Phe Ser Tyr Gln Pro Pro Gln Ser Ser Ser Arg
                        355                 360                 365

Phe Ser Val Ser Gln Thr Gly Asp Leu Thr Ile Thr Asn Val Gln Arg
                        370                 375                 380

Ser Asp Val Gly Tyr Tyr Ile Cys Gln Thr Leu Asn Val Ala Gly Ser
        385                 390                 395                 400

Ile Ile Thr Lys Ala Tyr Leu Glu Val Thr Asp Val Ile Ala Asp Arg
                        405                 410                 415

Pro Pro Pro Val Ile Arg Gln Gly Pro Val Asn Gln Thr Val Ala Val
                        420                 425                 430

Asp Gly Thr Leu Val Leu Ser Cys Val Ala Thr Gly Ser Pro Val Pro
                        435                 440                 445

Thr Ile Leu Trp Arg Lys Asp Gly Val Leu Val Ser Thr Gln Asp Ser
        450                 455                 460

Arg Ile Lys Gln Leu Glu Thr Gly Val Leu Gln Ile Arg Tyr Ala Lys
                        465                 470                 475                 480

Leu Gly Asp Thr Gly Arg Tyr Thr Cys Ile Ala Ser Thr Pro Ser Gly
                        485                 490                 495
```

```
Glu Ala Thr Trp Ser Ala Tyr Ile Glu Val Gln Glu Phe
            500                 505

<210> SEQ ID NO 15
<211> LENGTH: 225
<212> TYPE: PRT
<213> ORGANISM: Capra hircus

<400> SEQUENCE: 15

Met Ile Ala Glu Pro Ala His Phe Tyr Leu Phe Gly Phe Ile Cys Leu
1               5                   10                  15

Cys Ser Gly Ser Arg Leu Arg Gln Glu Asp Phe Pro Arg Ile Val
            20                  25                  30

Glu His Pro Ser Asp Leu Ile Val Ser Lys Gly Glu Pro Ala Thr Leu
            35                  40                  45

Asn Cys Lys Ala Glu Gly Arg Pro Thr Pro Thr Ile Glu Trp Tyr Lys
        50                  55                  60

Gly Gly Glu Arg Val Glu Thr Asp Lys Asp Pro Arg Ser His Arg
65                  70                  75                  80

Met Leu Leu Pro Ser Gly Ser Leu Phe Phe Leu Arg Ile Val His Gly
                85                  90                  95

Arg Lys Ser Arg Pro Asp Glu Gly Val Tyr Val Cys Val Ala Arg Asn
            100                 105                 110

Tyr Leu Gly Glu Ala Val Ser His Asn Ala Ser Leu Glu Val Ala Ile
            115                 120                 125

Leu Arg Asp Asp Phe Arg Gln Asn Pro Ser Asp Val Met Val Ala Val
        130                 135                 140

Gly Glu Pro Ala Val Met Glu Cys Gln Pro Arg Gly His Pro Glu
145                 150                 155                 160

Pro Thr Ile Ser Trp Lys Lys Asp Gly Ser Pro Leu Asp Asp Lys Asp
                165                 170                 175

Glu Arg Ile Thr Ile Arg Gly Gly Lys Leu Met Ile Thr Tyr Thr Arg
            180                 185                 190

Lys Ser Asp Ala Gly Lys Tyr Val Cys Val Gly Thr Asn Met Val Gly
        195                 200                 205

Glu Arg Glu Ser Glu Val Ala Glu Leu Thr Val Leu Glu Arg Pro Ser
    210                 215                 220
Phe
225

<210> SEQ ID NO 16
<211> LENGTH: 829
<212> TYPE: PRT
<213> ORGANISM: Ovis aries

<400> SEQUENCE: 16

Met Ile Ala Glu Pro Ala Arg Phe Tyr Leu Phe Gly Leu Ile Cys Leu
1               5                   10                  15

Cys Ser Gly Ser Arg Leu Arg Gln Glu Asp Phe Pro Arg Ile Val
            20                  25                  30

Glu His Pro Ser Asp Leu Ile Val Ser Lys Gly Glu Pro Ala Thr Leu
            35                  40                  45

Asn Cys Lys Ala Glu Gly Arg Pro Thr Pro Thr Ile Glu Trp Tyr Lys
        50                  55                  60

Gly Gly Glu Arg Val Glu Thr Asp Lys Asp Pro Arg Ser His Arg
65                  70                  75                  80
```

```
Met Leu Leu Pro Ser Gly Ser Leu Phe Phe Leu Arg Ile Val His Gly
                85                  90                  95

Arg Lys Ser Arg Pro Asp Glu Gly Val Tyr Ile Cys Val Ala Arg Asn
                100                 105                 110

Tyr Leu Gly Glu Ala Val Ser His Asn Ala Ser Leu Glu Val Ala Ile
            115                 120                 125

Leu Arg Asp Asp Phe Arg Gln Asn Pro Ser Asp Val Met Val Ala Val
130                 135                 140

Gly Glu Pro Ala Val Met Glu Cys Gln Pro Arg Gly His Pro Glu
145                 150                 155                 160

Pro Thr Ile Ser Trp Lys Lys Asp Gly Ser Pro Leu Asp Lys Asp
                165                 170                 175

Glu Arg Ile Thr Ile Arg Gly Gly Lys Leu Met Ile Thr Tyr Thr Arg
            180                 185                 190

Lys Ser Asp Ala Gly Lys Tyr Val Cys Val Gly Thr Asn Met Val Gly
            195                 200                 205

Glu Arg Glu Ser Glu Val Ala Glu Leu Thr Val Leu Glu Arg Pro Ser
210                 215                 220

Phe Val Lys Arg Pro Ser Asn Leu Ala Val Thr Val Asp Asp Ser Ala
225                 230                 235                 240

Glu Phe Lys Cys Glu Ala Arg Gly Asp Pro Val Pro Thr Val Arg Trp
                245                 250                 255

Arg Lys Asp Asp Gly Glu Leu Pro Lys Ser Arg Tyr Glu Ile Arg Asp
                260                 265                 270

Asp His Thr Leu Lys Ile Arg Lys Val Thr Ala Gly Asp Met Gly Ser
            275                 280                 285

Tyr Thr Cys Val Ala Glu Asn Met Val Gly Lys Ala Glu Ala Ser Ala
            290                 295                 300

Thr Leu Thr Val Gln Glu Pro Pro His Phe Val Val Lys Pro Arg Asp
305                 310                 315                 320

Gln Val Val Ala Leu Gly Arg Thr Val Thr Phe Gln Cys Glu Ala Thr
                325                 330                 335

Gly Asn Pro Gln Pro Ala Ile Phe Trp Arg Arg Glu Gly Ser Gln Asn
                340                 345                 350

Leu Leu Phe Ser Tyr Gln Pro Pro Gln Ser Ser Ser Arg Phe Ser Val
                355                 360                 365

Ser Gln Thr Gly Asp Leu Thr Ile Thr Asn Val Gln Arg Ser Asp Val
370                 375                 380

Gly Tyr Tyr Ile Cys Gln Thr Leu Asn Val Ala Gly Ser Ile Ile Thr
385                 390                 395                 400

Lys Ala Tyr Leu Glu Val Thr Asp Val Ile Ala Asp Arg Pro Pro
                405                 410                 415

Val Ile Arg Gln Gly Pro Val Asn Gln Thr Val Ala Val Asp Gly Thr
                420                 425                 430

Leu Ile Leu Ser Cys Val Ala Thr Gly Ser Pro Ala Pro Thr Ile Leu
            435                 440                 445

Trp Arg Lys Asp Gly Val Leu Val Ser Thr Gln Asp Ser Arg Ile Lys
450                 455                 460

Gln Leu Glu Ser Gly Val Leu Gln Ile Arg Tyr Ala Lys Leu Gly Asp
465                 470                 475                 480

Thr Gly Arg Tyr Thr Cys Thr Ala Ser Thr Pro Ser Gly Glu Ala Thr
                485                 490                 495
```

-continued

Trp Ser Ala Tyr Ile Glu Val Gln Glu Phe Gly Val Pro Val Gln Pro
                500                 505                 510

Pro Arg Pro Thr Asp Pro Asn Leu Ile Pro Ser Ala Pro Ser Lys Pro
            515                 520                 525

Glu Val Thr Asp Val Ser Lys Asn Thr Val Thr Leu Ser Trp Gln Pro
        530                 535                 540

Asn Leu Asn Ser Gly Ala Thr Pro Thr Ser Tyr Ile Ile Glu Ala Phe
545                 550                 555                 560

Ser His Ala Ser Gly Ser Ser Trp Gln Thr Ala Ala Glu Asn Val Lys
                565                 570                 575

Thr Glu Thr Phe Ala Ile Lys Gly Leu Lys Pro Asn Ala Ile Tyr Leu
            580                 585                 590

Phe Leu Val Arg Ala Ala Asn Ala Tyr Gly Ile Ser Asp Pro Ser Gln
        595                 600                 605

Ile Ser Asp Pro Val Lys Thr Gln Asp Val Pro Pro Thr Ser Gln Gly
        610                 615                 620

Val Asp His Lys Gln Val Gln Arg Glu Leu Gly Asn Val Val Leu His
625                 630                 635                 640

Leu His Asn Pro Thr Ile Leu Ser Ser Ser Val Glu Val His Trp
                645                 650                 655

Thr Val Asp Gln Gln Ser Gln Tyr Ile Gln Gly Tyr Lys Ile Leu Tyr
            660                 665                 670

Arg Pro Ser Gly Ala Ser His Gly Glu Ser Glu Trp Leu Val Phe Glu
        675                 680                 685

Val Arg Thr Pro Thr Lys Asn Ser Val Val Ile Pro Asp Leu Arg Lys
        690                 695                 700

Gly Val Asn Tyr Glu Ile Lys Ala Arg Pro Phe Phe Asn Glu Phe Gln
705                 710                 715                 720

Gly Ala Asp Ser Glu Ile Lys Phe Ala Lys Thr Leu Glu Glu Ala Pro
                725                 730                 735

Ser Ala Pro Pro Arg Ser Val Thr Val Ser Lys Asn Asp Gly Asn Gly
            740                 745                 750

Thr Ala Ile Leu Val Thr Trp Gln Pro Pro Glu Asp Thr Gln Asn
        755                 760                 765

Gly Met Val Gln Glu Tyr Lys Val Trp Cys Leu Gly Asn Glu Thr Lys
    770                 775                 780

Tyr His Ile Asn Lys Thr Val Asp Gly Ser Thr Phe Ser Val Val Ile
785                 790                 795                 800

Pro Ser Leu Val Pro Gly Ile Arg Tyr Ser Val Glu Val Ala Ala Ser
                805                 810                 815

Thr Gly Ala Gly Pro Gly Val Lys Ser Glu Pro Gln Phe
            820                 825

<210> SEQ ID NO 17
<211> LENGTH: 506
<212> TYPE: PRT
<213> ORGANISM: Ovis aries

<400> SEQUENCE: 17

Met Ile Ala Glu Pro Ala Arg Phe Tyr Leu Phe Gly Leu Ile Cys Leu
1               5                   10                  15

Cys Ser Gly Ser Arg Leu Arg Gln Glu Asp Phe Pro Pro Arg Ile Val
            20                  25                  30

Glu His Pro Ser Asp Leu Ile Val Ser Lys Gly Glu Pro Ala Thr Leu
        35                  40                  45

```
Asn Cys Lys Ala Glu Gly Arg Pro Thr Pro Thr Ile Glu Trp Tyr Lys
     50                  55                  60

Gly Gly Glu Arg Val Glu Thr Asp Lys Asp Asp Pro Arg Ser His Arg
 65                  70                  75                  80

Met Leu Leu Pro Ser Gly Ser Leu Phe Phe Leu Arg Ile Val His Gly
                 85                  90                  95

Arg Lys Ser Arg Pro Asp Glu Gly Val Tyr Ile Cys Val Ala Arg Asn
                100                 105                 110

Tyr Leu Gly Glu Ala Val Ser His Asn Ala Ser Leu Glu Val Ala Ile
             115                 120                 125

Leu Arg Asp Asp Phe Arg Gln Asn Pro Ser Asp Val Met Val Ala Val
     130                 135                 140

Gly Glu Pro Ala Val Met Glu Cys Gln Pro Pro Arg Gly His Pro Glu
145                 150                 155                 160

Pro Thr Ile Ser Trp Lys Lys Asp Gly Ser Pro Leu Asp Asp Lys Asp
                165                 170                 175

Glu Arg Ile Thr Ile Arg Gly Gly Lys Leu Met Ile Thr Tyr Thr Arg
                180                 185                 190

Lys Ser Asp Ala Gly Lys Tyr Val Cys Val Gly Thr Asn Met Val Gly
             195                 200                 205

Glu Arg Glu Ser Glu Val Ala Glu Leu Thr Val Leu Glu Arg Pro Ser
     210                 215                 220

Phe Val Lys Arg Pro Ser Asn Leu Ala Val Thr Val Asp Asp Ser Ala
225                 230                 235                 240

Glu Phe Lys Cys Glu Ala Arg Gly Asp Pro Val Pro Thr Val Arg Trp
                245                 250                 255

Arg Lys Asp Asp Gly Glu Leu Pro Lys Ser Arg Tyr Glu Ile Arg Asp
             260                 265                 270

Asp His Thr Leu Lys Ile Arg Lys Val Thr Ala Gly Asp Met Gly Ser
     275                 280                 285

Tyr Thr Cys Val Ala Glu Asn Met Val Gly Lys Ala Glu Ala Ser Ala
             290                 295                 300

Thr Leu Thr Val Gln Glu Pro Pro His Phe Val Val Lys Pro Arg Asp
305                 310                 315                 320

Gln Val Val Ala Leu Gly Arg Thr Val Thr Phe Gln Cys Glu Ala Thr
                325                 330                 335

Gly Asn Pro Gln Pro Ala Ile Phe Trp Arg Arg Glu Gly Ser Gln Asn
             340                 345                 350

Leu Leu Phe Ser Tyr Gln Pro Pro Gln Ser Ser Ser Arg Phe Ser Val
     355                 360                 365

Ser Gln Thr Gly Asp Leu Thr Ile Thr Asn Val Gln Arg Ser Asp Val
370                 375                 380

Gly Tyr Tyr Ile Cys Gln Thr Leu Asn Val Ala Gly Ser Ile Ile Thr
385                 390                 395                 400

Lys Ala Tyr Leu Glu Val Thr Asp Val Ile Ala Asp Arg Pro Pro Pro
                405                 410                 415

Val Ile Arg Gln Gly Pro Val Asn Gln Thr Val Ala Val Asp Gly Thr
             420                 425                 430

Leu Ile Leu Ser Cys Val Ala Thr Gly Ser Pro Ala Pro Thr Ile Leu
     435                 440                 445

Trp Arg Lys Asp Gly Val Leu Val Ser Thr Gln Asp Ser Arg Ile Lys
450                 455                 460
```

```
Gln Leu Glu Ser Gly Val Leu Gln Ile Arg Tyr Ala Lys Leu Gly Asp
465                 470                 475                 480

Thr Gly Arg Tyr Thr Cys Thr Ala Ser Thr Pro Ser Gly Glu Ala Thr
            485                 490                 495

Trp Ser Ala Tyr Ile Glu Val Gln Glu Phe
            500                 505

<210> SEQ ID NO 18
<211> LENGTH: 225
<212> TYPE: PRT
<213> ORGANISM: Ovis aries

<400> SEQUENCE: 18

Met Ile Ala Glu Pro Ala Arg Phe Tyr Leu Phe Gly Leu Ile Cys Leu
1               5                   10                  15

Cys Ser Gly Ser Arg Leu Arg Gln Glu Asp Phe Pro Pro Arg Ile Val
            20                  25                  30

Glu His Pro Ser Asp Leu Ile Val Ser Lys Gly Glu Pro Ala Thr Leu
            35                  40                  45

Asn Cys Lys Ala Glu Gly Arg Pro Thr Pro Thr Ile Glu Trp Tyr Lys
50                  55                  60

Gly Gly Glu Arg Val Glu Thr Asp Lys Asp Pro Arg Ser His Arg
65                  70                  75                  80

Met Leu Leu Pro Ser Gly Ser Leu Phe Phe Leu Arg Ile Val His Gly
                85                  90                  95

Arg Lys Ser Arg Pro Asp Glu Gly Val Tyr Ile Cys Val Ala Arg Asn
            100                 105                 110

Tyr Leu Gly Glu Ala Val Ser His Asn Ala Ser Leu Glu Val Ala Ile
            115                 120                 125

Leu Arg Asp Asp Phe Arg Gln Asn Pro Ser Asp Val Met Val Ala Val
            130                 135                 140

Gly Glu Pro Ala Val Met Glu Cys Gln Pro Pro Arg Gly His Pro Glu
145                 150                 155                 160

Pro Thr Ile Ser Trp Lys Lys Asp Gly Ser Pro Leu Asp Asp Lys Asp
                165                 170                 175

Glu Arg Ile Thr Ile Arg Gly Gly Lys Leu Met Ile Thr Tyr Thr Arg
            180                 185                 190

Lys Ser Asp Ala Gly Lys Tyr Val Cys Val Gly Thr Asn Met Val Gly
            195                 200                 205

Glu Arg Glu Ser Glu Val Ala Glu Leu Thr Val Leu Glu Arg Pro Ser
            210                 215                 220

Phe
225

<210> SEQ ID NO 19
<211> LENGTH: 832
<212> TYPE: PRT
<213> ORGANISM: Bos Mutas

<400> SEQUENCE: 19

Met Ile Ala Glu Pro Ala His Phe Tyr Leu Phe Gly Leu Ile Cys Leu
1               5                   10                  15

Cys Ser Gly Ser Arg Leu Arg Gln Glu Asp Phe Pro Pro Arg Ile Val
            20                  25                  30

Glu His Pro Ser Asp Leu Ile Val Ser Lys Gly Glu Pro Ala Thr Leu
            35                  40                  45
```

```
Asn Cys Lys Ala Glu Gly Arg Pro Thr Pro Thr Ile Glu Trp Tyr Lys
    50                  55                  60

Gly Gly Glu Arg Val Glu Thr Asp Lys Asp Pro Arg Ser His Arg
65                  70                  75                  80

Met Leu Leu Pro Ser Gly Ser Leu Phe Phe Leu Arg Ile Val His Gly
                85                  90                  95

Arg Lys Ser Arg Pro Asp Glu Gly Val Tyr Val Cys Val Ala Arg Asn
                100                 105                 110

Tyr Leu Gly Glu Ala Val Ser His Asn Ala Ser Leu Glu Val Ala Ile
            115                 120                 125

Leu Arg Asp Asp Phe Arg Gln Asn Pro Ser Asp Val Met Val Ala Val
    130                 135                 140

Gly Glu Pro Ala Val Met Glu Cys Gln Pro Pro Arg Gly His Pro Glu
145                 150                 155                 160

Pro Thr Ile Ser Trp Lys Lys Asp Gly Ser Pro Leu Asp Asp Lys Asp
                165                 170                 175

Glu Arg Ile Thr Ile Arg Gly Gly Lys Leu Met Ile Thr Tyr Thr Arg
                180                 185                 190

Lys Ser Asp Ala Gly Lys Tyr Val Cys Val Gly Thr Asn Met Val Gly
    195                 200                 205

Glu Arg Glu Ser Glu Val Ala Glu Leu Thr Val Leu Glu Arg Pro Ser
    210                 215                 220

Phe Val Lys Arg Pro Ser Asn Leu Ala Val Thr Val Asp Asp Ser Ala
225                 230                 235                 240

Glu Phe Lys Cys Glu Ala Arg Gly Asp Pro Val Pro Thr Val Arg Trp
                245                 250                 255

Arg Lys Asp Asp Gly Glu Leu Pro Lys Ser Arg Tyr Glu Ile Arg Asp
            260                 265                 270

Asp His Thr Leu Lys Ile Arg Lys Val Thr Ala Gly Asp Met Gly Ser
        275                 280                 285

Tyr Thr Cys Val Ala Glu Asn Met Val Gly Lys Ala Glu Ala Ser Ala
    290                 295                 300

Thr Leu Thr Val Gln Val Gly Ser Glu Pro Pro His Phe Val Val Lys
305                 310                 315                 320

Pro Arg Asp Gln Val Val Ala Leu Gly Arg Thr Val Thr Phe Gln Cys
                325                 330                 335

Glu Ala Thr Gly Asn Pro Gln Pro Ala Ile Phe Trp Arg Arg Glu Gly
                340                 345                 350

Ser Gln Asn Leu Leu Phe Ser Tyr Gln Pro Pro Gln Ser Ser Ser Arg
    355                 360                 365

Phe Ser Val Ser Gln Thr Gly Asp Leu Thr Ile Thr Asn Val Gln Arg
370                 375                 380

Ser Asp Val Gly Tyr Tyr Ile Cys Gln Thr Leu Asn Val Ala Gly Ser
385                 390                 395                 400

Ile Ile Thr Lys Ala Tyr Leu Glu Val Thr Asp Val Ile Ala Asp Arg
                405                 410                 415

Pro Pro Pro Val Ile Arg Gln Gly Pro Val Asn Gln Thr Val Ala Val
                420                 425                 430

Asp Gly Thr Leu Val Leu Ser Cys Val Ala Thr Gly Ser Pro Val Pro
            435                 440                 445

Thr Ile Leu Trp Arg Lys Asp Gly Val Leu Val Ser Thr Gln Asp Ser
450                 455                 460

Arg Ile Lys Gln Leu Glu Thr Gly Val Leu Gln Ile Arg Tyr Ala Lys
```

```
            465                 470                 475                 480
Leu Gly Asp Thr Gly Arg Tyr Thr Cys Ile Ala Ser Thr Pro Ser Gly
                485                 490                 495

Glu Ala Thr Trp Ser Ala Tyr Ile Glu Val Gln Glu Phe Gly Val Pro
                500                 505                 510

Val Gln Pro Arg Pro Thr Asp Pro Asn Leu Ile Pro Ser Ala Pro
            515                 520                 525

Ser Lys Pro Glu Val Thr Asp Val Ser Arg Asn Thr Val Thr Leu Ser
            530                 535                 540

Trp Gln Pro Asn Leu Asn Ser Gly Ala Thr Pro Thr Ser Tyr Ile Ile
545                 550                 555                 560

Glu Ala Phe Ser His Ala Ser Gly Ser Ser Trp Gln Thr Val Ala Glu
                565                 570                 575

Asn Val Lys Thr Glu Thr Phe Ala Ile Lys Gly Leu Lys Pro Asn Ala
                580                 585                 590

Ile Tyr Leu Phe Leu Val Arg Ala Ala Asn Ala Tyr Gly Ile Ser Asp
            595                 600                 605

Pro Ser Gln Ile Ser Asp Pro Val Lys Thr Gln Asp Val Pro Pro Thr
            610                 615                 620

Ser Gln Gly Val Asp His Lys Gln Val Gln Arg Glu Leu Gly Asn Val
625                 630                 635                 640

Val Leu His Leu His Asn Pro Thr Ile Leu Ser Ser Ser Ser Ile Glu
                645                 650                 655

Val His Trp Thr Val Asp Gln Gln Ser Gln Tyr Ile Gln Gly Tyr Lys
                660                 665                 670

Val Leu Tyr Arg Pro Ser Gly Ala Asn His Gly Glu Ser Glu Trp Leu
            675                 680                 685

Val Phe Glu Val Arg Thr Pro Thr Lys Asn Ser Val Val Ile Pro Asp
            690                 695                 700

Leu Lys Lys Gly Val Asn Tyr Glu Ile Lys Ala Arg Pro Phe Phe Asn
705                 710                 715                 720

Glu Phe Gln Gly Ala Asp Ser Glu Ile Lys Phe Ala Lys Thr Leu Glu
                725                 730                 735

Glu Ala Pro Ser Ala Pro Pro Gln Ser Val Thr Val Ser Lys Asn Asp
                740                 745                 750

Gly Asn Gly Thr Ala Ile Leu Val Ser Trp Gln Pro Pro Glu Asp
            755                 760                 765

Thr Gln Asn Gly Met Val Gln Glu Tyr Lys Val Trp Cys Leu Gly Asn
            770                 775                 780

Glu Thr Arg Tyr His Ile Asn Lys Thr Val Asp Gly Ser Thr Phe Ser
785                 790                 795                 800

Val Val Ile Pro Ser Leu Val Pro Gly Ile Arg Tyr Ser Val Glu Val
                805                 810                 815

Ala Ala Ser Thr Gly Ala Gly Ser Gly Val Lys Ser Glu Pro Gln Phe
            820                 825                 830

<210> SEQ ID NO 20
<211> LENGTH: 509
<212> TYPE: PRT
<213> ORGANISM: Bos Mutas

<400> SEQUENCE: 20

Met Ile Ala Glu Pro Ala His Phe Tyr Leu Phe Gly Leu Ile Cys Leu
1               5                   10                  15
```

-continued

```
Cys Ser Gly Ser Arg Leu Arg Gln Glu Asp Phe Pro Arg Ile Val
             20                  25                  30

Glu His Pro Ser Asp Leu Ile Val Ser Lys Gly Glu Pro Ala Thr Leu
         35                  40                  45

Asn Cys Lys Ala Glu Gly Arg Pro Thr Pro Thr Ile Glu Trp Tyr Lys
 50                  55                  60

Gly Gly Glu Arg Val Glu Thr Asp Lys Asp Pro Arg Ser His Arg
 65                  70                  75                  80

Met Leu Leu Pro Ser Gly Ser Leu Phe Phe Leu Arg Ile Val His Gly
                 85                  90                  95

Arg Lys Ser Arg Pro Asp Glu Gly Val Tyr Val Cys Val Ala Arg Asn
             100                 105                 110

Tyr Leu Gly Glu Ala Val Ser His Asn Ala Ser Leu Glu Val Ala Ile
         115                 120                 125

Leu Arg Asp Asp Phe Arg Gln Asn Pro Ser Asp Val Met Val Ala Val
     130                 135                 140

Gly Glu Pro Ala Val Met Glu Cys Gln Pro Pro Arg Gly His Pro Glu
145                 150                 155                 160

Pro Thr Ile Ser Trp Lys Lys Asp Gly Ser Pro Leu Asp Asp Lys Asp
                 165                 170                 175

Glu Arg Ile Thr Ile Arg Gly Gly Lys Leu Met Ile Thr Tyr Thr Arg
             180                 185                 190

Lys Ser Asp Ala Gly Lys Tyr Val Cys Val Gly Thr Asn Met Val Gly
         195                 200                 205

Glu Arg Glu Ser Glu Val Ala Glu Leu Thr Val Leu Glu Arg Pro Ser
     210                 215                 220

Phe Val Lys Arg Pro Ser Asn Leu Ala Val Thr Val Asp Asp Ser Ala
225                 230                 235                 240

Glu Phe Lys Cys Glu Ala Arg Gly Asp Pro Val Pro Thr Val Arg Trp
                 245                 250                 255

Arg Lys Asp Asp Gly Glu Leu Pro Lys Ser Arg Tyr Glu Ile Arg Asp
             260                 265                 270

Asp His Thr Leu Lys Ile Arg Lys Val Thr Ala Gly Asp Met Gly Ser
         275                 280                 285

Tyr Thr Cys Val Ala Glu Asn Met Val Gly Lys Ala Glu Ala Ser Ala
     290                 295                 300

Thr Leu Thr Val Gln Val Gly Ser Glu Pro Pro His Phe Val Val Lys
305                 310                 315                 320

Pro Arg Asp Gln Val Val Ala Leu Gly Arg Thr Val Thr Phe Gln Cys
                 325                 330                 335

Glu Ala Thr Gly Asn Pro Gln Pro Ala Ile Phe Trp Arg Arg Glu Gly
             340                 345                 350

Ser Gln Asn Leu Leu Phe Ser Tyr Gln Pro Pro Gln Ser Ser Ser Arg
         355                 360                 365

Phe Ser Val Ser Gln Thr Gly Asp Leu Thr Ile Thr Asn Val Gln Arg
     370                 375                 380

Ser Asp Val Gly Tyr Tyr Ile Cys Gln Thr Leu Asn Val Ala Gly Ser
385                 390                 395                 400

Ile Ile Thr Lys Ala Tyr Leu Glu Val Thr Asp Val Ile Ala Asp Arg
                 405                 410                 415

Pro Pro Pro Val Ile Arg Gln Gly Pro Val Asn Gln Thr Val Ala Val
             420                 425                 430

Asp Gly Thr Leu Val Leu Ser Cys Val Ala Thr Gly Ser Pro Val Pro
```

```
                435                 440                 445
Thr Ile Leu Trp Arg Lys Asp Gly Val Leu Val Ser Thr Gln Asp Ser
    450                 455                 460

Arg Ile Lys Gln Leu Glu Thr Gly Val Leu Gln Ile Arg Tyr Ala Lys
465                 470                 475                 480

Leu Gly Asp Thr Gly Arg Tyr Thr Cys Ile Ala Ser Thr Pro Ser Gly
                485                 490                 495

Glu Ala Thr Trp Ser Ala Tyr Ile Glu Val Gln Glu Phe
            500                 505

<210> SEQ ID NO 21
<211> LENGTH: 225
<212> TYPE: PRT
<213> ORGANISM: Bos Mutas

<400> SEQUENCE: 21

Met Ile Ala Glu Pro Ala His Phe Tyr Leu Phe Gly Leu Ile Cys Leu
1               5                   10                  15

Cys Ser Gly Ser Arg Leu Arg Gln Glu Asp Phe Pro Pro Arg Ile Val
            20                  25                  30

Glu His Pro Ser Asp Leu Ile Val Ser Lys Gly Glu Pro Ala Thr Leu
        35                  40                  45

Asn Cys Lys Ala Glu Gly Arg Pro Thr Pro Thr Ile Glu Trp Tyr Lys
    50                  55                  60

Gly Gly Glu Arg Val Glu Thr Asp Lys Asp Asp Pro Arg Ser His Arg
65                  70                  75                  80

Met Leu Leu Pro Ser Gly Ser Leu Phe Phe Leu Arg Ile Val His Gly
                85                  90                  95

Arg Lys Ser Arg Pro Asp Glu Gly Val Tyr Val Cys Val Ala Arg Asn
            100                 105                 110

Tyr Leu Gly Glu Ala Val Ser His Asn Ala Ser Leu Glu Val Ala Ile
        115                 120                 125

Leu Arg Asp Asp Phe Arg Gln Asn Pro Ser Asp Val Met Val Ala Val
    130                 135                 140

Gly Glu Pro Ala Val Met Glu Cys Gln Pro Pro Arg Gly His Pro Glu
145                 150                 155                 160

Pro Thr Ile Ser Trp Lys Lys Asp Gly Ser Pro Leu Asp Asp Lys Asp
                165                 170                 175

Glu Arg Ile Thr Ile Arg Gly Gly Lys Leu Met Ile Thr Tyr Thr Arg
            180                 185                 190

Lys Ser Asp Ala Gly Lys Tyr Val Cys Val Gly Thr Asn Met Val Gly
        195                 200                 205

Glu Arg Glu Ser Glu Val Ala Glu Leu Thr Val Leu Glu Arg Pro Ser
    210                 215                 220

Phe
225

<210> SEQ ID NO 22
<211> LENGTH: 829
<212> TYPE: PRT
<213> ORGANISM: Mus musculus

<400> SEQUENCE: 22

Met Ile Ala Glu Pro Ala Arg Phe Tyr Leu Phe Gly Leu Ile Cys Leu
1               5                   10                  15

Cys Ser Gly Ser Arg Leu Arg Gln Glu Asp Phe Pro Pro Arg Ile Val
```

-continued

```
                    20                  25                  30
Glu His Pro Ser Asp Leu Ile Val Ser Lys Gly Glu Pro Ala Thr Leu
                35                  40                  45
Asn Cys Lys Ala Glu Gly Arg Pro Thr Pro Thr Ile Glu Trp Tyr Lys
            50                  55                  60
Gly Gly Glu Arg Val Glu Thr Asp Lys Asp Pro Arg Ser His Arg
65                  70                  75                  80
Met Leu Leu Pro Ser Gly Ser Leu Phe Phe Leu Arg Ile Val His Gly
                    85                  90                  95
Arg Lys Ser Arg Pro Asp Glu Gly Val Tyr Ile Cys Val Ala Arg Asn
                100                 105                 110
Tyr Leu Gly Glu Ala Val Ser His Asn Ala Ser Leu Glu Val Ala Ile
                115                 120                 125
Leu Arg Asp Asp Phe Arg Gln Asn Pro Ser Asp Val Met Val Ala Val
                130                 135                 140
Gly Glu Pro Ala Val Met Glu Cys Gln Pro Pro Arg Gly His Pro Glu
145                 150                 155                 160
Pro Thr Ile Ser Trp Lys Lys Asp Gly Ser Pro Leu Asp Asp Lys Asp
                165                 170                 175
Glu Arg Ile Thr Ile Arg Gly Gly Lys Leu Met Ile Thr Tyr Thr Arg
                180                 185                 190
Lys Ser Asp Ala Gly Lys Tyr Val Cys Val Gly Thr Asn Met Val Gly
                195                 200                 205
Glu Arg Glu Ser Glu Val Ala Glu Leu Thr Val Leu Glu Arg Pro Ser
                210                 215                 220
Phe Val Lys Arg Pro Ser Asn Leu Ala Val Thr Val Asp Asp Ser Ala
225                 230                 235                 240
Glu Phe Lys Cys Glu Ala Arg Gly Asp Pro Val Pro Thr Val Arg Trp
                245                 250                 255
Arg Lys Asp Asp Gly Glu Leu Pro Lys Ser Arg Tyr Glu Ile Arg Asp
                260                 265                 270
Asp His Thr Leu Lys Ile Arg Lys Val Thr Ala Gly Asp Met Gly Ser
                275                 280                 285
Tyr Thr Cys Val Ala Glu Asn Met Val Gly Lys Ala Glu Ala Ser Ala
                290                 295                 300
Thr Leu Thr Val Gln Glu Pro Pro His Phe Val Val Lys Pro Arg Asp
305                 310                 315                 320
Gln Val Val Ala Leu Gly Arg Thr Val Thr Phe Gln Cys Glu Ala Thr
                325                 330                 335
Gly Asn Pro Gln Pro Ala Ile Phe Trp Arg Arg Glu Gly Ser Gln Asn
                340                 345                 350
Leu Leu Phe Ser Tyr Gln Pro Pro Gln Ser Ser Ser Arg Phe Ser Val
                355                 360                 365
Ser Gln Thr Gly Asp Leu Thr Ile Thr Asn Val Gln Arg Ser Asp Val
                370                 375                 380
Gly Tyr Tyr Ile Cys Gln Thr Leu Asn Val Ala Gly Ser Ile Ile Thr
385                 390                 395                 400
Lys Ala Tyr Leu Glu Val Thr Asp Val Ile Ala Asp Arg Pro Pro Pro
                405                 410                 415
Val Ile Arg Gln Gly Pro Val Asn Gln Thr Val Ala Val Asp Gly Thr
                420                 425                 430
Leu Ile Leu Ser Cys Val Ala Thr Gly Ser Pro Ala Pro Thr Ile Leu
                435                 440                 445
```

Trp Arg Lys Asp Gly Val Leu Val Ser Thr Gln Asp Ser Arg Ile Lys
450                 455                 460

Gln Leu Glu Ser Gly Val Leu Gln Ile Arg Tyr Ala Lys Leu Gly Asp
465                 470                 475                 480

Thr Gly Arg Tyr Thr Cys Thr Ala Ser Thr Pro Ser Gly Glu Ala Thr
            485                 490                 495

Trp Ser Ala Tyr Ile Glu Val Gln Glu Phe Gly Val Pro Val Gln Pro
            500                 505                 510

Pro Arg Pro Thr Asp Pro Asn Leu Ile Pro Ser Ala Pro Ser Lys Pro
            515                 520                 525

Glu Val Thr Asp Val Ser Lys Asn Thr Val Thr Leu Ser Trp Gln Pro
530                 535                 540

Asn Leu Asn Ser Gly Ala Thr Pro Thr Ser Tyr Ile Ile Glu Ala Phe
545                 550                 555                 560

Ser His Ala Ser Gly Ser Ser Trp Gln Thr Ala Ala Glu Asn Val Lys
                565                 570                 575

Thr Glu Thr Phe Ala Ile Lys Gly Leu Lys Pro Asn Ala Ile Tyr Leu
            580                 585                 590

Phe Leu Val Arg Ala Ala Asn Ala Tyr Gly Ile Ser Asp Pro Ser Gln
            595                 600                 605

Ile Ser Asp Pro Val Lys Thr Gln Asp Val Pro Pro Thr Ser Gln Gly
610                 615                 620

Val Asp His Lys Gln Val Gln Arg Glu Leu Gly Asn Val Val Leu His
625                 630                 635                 640

Leu His Asn Pro Thr Ile Leu Ser Ser Ser Val Glu Val His Trp
                645                 650                 655

Thr Val Asp Gln Gln Ser Gln Tyr Ile Gln Gly Tyr Lys Ile Leu Tyr
            660                 665                 670

Arg Pro Ser Gly Ala Ser His Gly Glu Ser Glu Trp Leu Val Phe Glu
            675                 680                 685

Val Arg Thr Pro Thr Lys Asn Ser Val Val Ile Pro Asp Leu Arg Lys
690                 695                 700

Gly Val Asn Tyr Glu Ile Lys Ala Arg Pro Phe Phe Asn Glu Phe Gln
705                 710                 715                 720

Gly Ala Asp Ser Glu Ile Lys Phe Ala Lys Thr Leu Glu Glu Ala Pro
            725                 730                 735

Ser Ala Pro Pro Arg Ser Val Thr Val Ser Lys Asn Asp Gly Asn Gly
            740                 745                 750

Thr Ala Ile Leu Val Thr Trp Gln Pro Pro Glu Asp Thr Gln Asn
            755                 760                 765

Gly Met Val Gln Glu Tyr Lys Val Trp Cys Leu Gly Asn Glu Thr Lys
770                 775                 780

Tyr His Ile Asn Lys Thr Val Asp Gly Ser Thr Phe Ser Val Val Ile
785                 790                 795                 800

Pro Ser Leu Val Pro Gly Ile Arg Tyr Ser Val Glu Val Ala Ala Ser
                805                 810                 815

Thr Gly Ala Gly Pro Gly Val Lys Ser Glu Pro Gln Phe
            820                 825

<210> SEQ ID NO 23
<211> LENGTH: 506
<212> TYPE: PRT
<213> ORGANISM: Mus musculus

```
<400> SEQUENCE: 23

Met Ile Ala Glu Pro Ala Arg Phe Tyr Leu Phe Gly Leu Ile Cys Leu
1               5                   10                  15

Cys Ser Gly Ser Arg Leu Arg Gln Glu Asp Phe Pro Pro Arg Ile Val
            20                  25                  30

Glu His Pro Ser Asp Leu Ile Val Ser Lys Gly Glu Pro Ala Thr Leu
        35                  40                  45

Asn Cys Lys Ala Glu Gly Arg Pro Thr Pro Thr Ile Glu Trp Tyr Lys
    50                  55                  60

Gly Gly Glu Arg Val Glu Thr Asp Lys Asp Pro Arg Ser His Arg
65                  70                  75                  80

Met Leu Leu Pro Ser Gly Ser Leu Phe Phe Leu Arg Ile Val His Gly
                85                  90                  95

Arg Lys Ser Arg Pro Asp Glu Gly Val Tyr Ile Cys Val Ala Arg Asn
            100                 105                 110

Tyr Leu Gly Glu Ala Val Ser His Asn Ala Ser Leu Glu Val Ala Ile
        115                 120                 125

Leu Arg Asp Asp Phe Arg Gln Asn Pro Ser Asp Val Met Val Ala Val
    130                 135                 140

Gly Glu Pro Ala Val Met Glu Cys Gln Pro Pro Arg Gly His Pro Glu
145                 150                 155                 160

Pro Thr Ile Ser Trp Lys Lys Asp Gly Ser Pro Leu Asp Asp Lys Asp
                165                 170                 175

Glu Arg Ile Thr Ile Arg Gly Gly Lys Leu Met Ile Thr Tyr Thr Arg
            180                 185                 190

Lys Ser Asp Ala Gly Lys Tyr Val Cys Val Gly Thr Asn Met Val Gly
        195                 200                 205

Glu Arg Glu Ser Glu Val Ala Glu Leu Thr Val Leu Glu Arg Pro Ser
    210                 215                 220

Phe Val Lys Arg Pro Ser Asn Leu Ala Val Thr Val Asp Asp Ser Ala
225                 230                 235                 240

Glu Phe Lys Cys Glu Ala Arg Gly Asp Pro Val Pro Thr Val Arg Trp
                245                 250                 255

Arg Lys Asp Asp Gly Glu Leu Pro Lys Ser Arg Tyr Glu Ile Arg Asp
            260                 265                 270

Asp His Thr Leu Lys Ile Arg Lys Val Thr Ala Gly Asp Met Gly Ser
        275                 280                 285

Tyr Thr Cys Val Ala Glu Asn Met Val Gly Lys Ala Glu Ala Ser Ala
    290                 295                 300

Thr Leu Thr Val Gln Glu Pro Pro His Phe Val Val Lys Pro Arg Asp
305                 310                 315                 320

Gln Val Val Ala Leu Gly Arg Thr Val Thr Phe Gln Cys Glu Ala Thr
                325                 330                 335

Gly Asn Pro Gln Pro Ala Ile Phe Trp Arg Arg Glu Gly Ser Gln Asn
            340                 345                 350

Leu Leu Phe Ser Tyr Gln Pro Pro Gln Ser Ser Arg Phe Ser Val
        355                 360                 365

Ser Gln Thr Gly Asp Leu Thr Ile Thr Asn Val Gln Arg Ser Asp Val
    370                 375                 380

Gly Tyr Tyr Ile Cys Gln Thr Leu Asn Val Ala Gly Ser Ile Ile Thr
385                 390                 395                 400

Lys Ala Tyr Leu Glu Val Thr Asp Val Ile Ala Asp Arg Pro Pro Pro
                405                 410                 415
```

Val Ile Arg Gln Gly Pro Val Asn Gln Thr Val Ala Val Asp Gly Thr
            420                 425                 430

Leu Ile Leu Ser Cys Val Ala Thr Gly Ser Pro Ala Pro Thr Ile Leu
            435                 440                 445

Trp Arg Lys Asp Gly Val Leu Val Ser Thr Gln Asp Ser Arg Ile Lys
450                 455                 460

Gln Leu Glu Ser Gly Val Leu Gln Ile Arg Tyr Ala Lys Leu Gly Asp
465                 470                 475                 480

Thr Gly Arg Tyr Thr Cys Thr Ala Ser Thr Pro Ser Gly Glu Ala Thr
                485                 490                 495

Trp Ser Ala Tyr Ile Glu Val Gln Glu Phe
            500                 505

<210> SEQ ID NO 24
<211> LENGTH: 225
<212> TYPE: PRT
<213> ORGANISM: Mus musculus

<400> SEQUENCE: 24

Met Ile Ala Glu Pro Ala Arg Phe Tyr Leu Phe Gly Leu Ile Cys Leu
1               5                   10                  15

Cys Ser Gly Ser Arg Leu Arg Gln Glu Asp Phe Pro Pro Arg Ile Val
                20                  25                  30

Glu His Pro Ser Asp Leu Ile Val Ser Lys Gly Glu Pro Ala Thr Leu
            35                  40                  45

Asn Cys Lys Ala Glu Gly Arg Pro Thr Pro Thr Ile Glu Trp Tyr Lys
        50                  55                  60

Gly Gly Glu Arg Val Glu Thr Asp Lys Asp Asp Pro Arg Ser His Arg
65                  70                  75                  80

Met Leu Leu Pro Ser Gly Ser Leu Phe Phe Leu Arg Ile Val His Gly
                85                  90                  95

Arg Lys Ser Arg Pro Asp Glu Gly Val Tyr Ile Cys Val Ala Arg Asn
                100                 105                 110

Tyr Leu Gly Glu Ala Val Ser His Asn Ala Ser Leu Glu Val Ala Ile
            115                 120                 125

Leu Arg Asp Asp Phe Arg Gln Asn Pro Ser Asp Val Met Val Ala Val
        130                 135                 140

Gly Glu Pro Ala Val Met Glu Cys Gln Pro Pro Arg Gly His Pro Glu
145                 150                 155                 160

Pro Thr Ile Ser Trp Lys Lys Asp Gly Ser Pro Leu Asp Asp Lys Asp
                165                 170                 175

Glu Arg Ile Thr Ile Arg Gly Gly Lys Leu Met Ile Thr Tyr Thr Arg
            180                 185                 190

Lys Ser Asp Ala Gly Lys Tyr Val Cys Val Gly Thr Asn Met Val Gly
        195                 200                 205

Glu Arg Glu Ser Glu Val Ala Glu Leu Thr Val Leu Glu Arg Pro Ser
    210                 215                 220

Phe
225

<210> SEQ ID NO 25
<211> LENGTH: 829
<212> TYPE: PRT
<213> ORGANISM: Rattus norvegicus

<400> SEQUENCE: 25

-continued

```
Met Ile Ala Glu Pro Ala His Phe Tyr Leu Phe Gly Leu Ile Cys Leu
1               5                   10                  15

Cys Ser Gly Ser Arg Leu Arg Gln Glu Asp Phe Pro Pro Arg Ile Val
            20                  25                  30

Glu His Pro Ser Asp Leu Ile Val Ser Lys Gly Glu Pro Ala Thr Leu
            35                  40                  45

Asn Cys Lys Ala Glu Gly Arg Pro Thr Pro Thr Ile Glu Trp Tyr Lys
    50                  55                  60

Gly Gly Glu Arg Val Glu Thr Asp Lys Asp Asp Pro Arg Ser His Arg
65                  70                  75                  80

Met Leu Leu Pro Ser Gly Ser Leu Phe Phe Leu Arg Ile Val His Gly
                85                  90                  95

Arg Lys Ser Arg Pro Asp Glu Gly Val Tyr Ile Cys Val Ala Arg Asn
                100                 105                 110

Tyr Leu Gly Glu Ala Val Ser His Asn Ala Ser Leu Glu Val Ala Ile
            115                 120                 125

Leu Arg Asp Asp Phe Arg Gln Asn Pro Ser Asp Val Met Val Ala Val
    130                 135                 140

Gly Glu Pro Ala Val Met Glu Cys Gln Pro Pro Arg Gly His Pro Glu
145                 150                 155                 160

Pro Thr Ile Ser Trp Lys Lys Asp Gly Ser Pro Leu Asp Asp Lys Asp
                165                 170                 175

Glu Arg Ile Thr Ile Arg Gly Gly Lys Leu Met Ile Thr Tyr Thr Arg
                180                 185                 190

Lys Ser Asp Ala Gly Lys Tyr Val Cys Val Gly Thr Asn Met Val Gly
            195                 200                 205

Glu Arg Glu Ser Glu Val Ala Glu Leu Thr Val Leu Glu Arg Pro Ser
    210                 215                 220

Phe Val Lys Arg Pro Ser Asn Leu Ala Val Thr Val Asp Asp Ser Ala
225                 230                 235                 240

Glu Phe Lys Cys Glu Ala Arg Gly Asp Pro Val Pro Thr Val Arg Trp
                245                 250                 255

Arg Lys Asp Gly Glu Leu Pro Lys Ser Arg Tyr Glu Ile Arg Asp
                260                 265                 270

Asp His Thr Leu Lys Ile Arg Lys Val Thr Ala Gly Asp Met Gly Ser
            275                 280                 285

Tyr Thr Cys Val Ala Glu Asn Met Val Gly Lys Ala Glu Ala Ser Ala
    290                 295                 300

Thr Leu Thr Val Gln Glu Pro Pro His Phe Val Lys Pro Arg Asp
305                 310                 315                 320

Gln Val Val Ala Leu Gly Arg Thr Val Thr Phe Gln Cys Glu Ala Thr
                325                 330                 335

Gly Asn Pro Gln Pro Ala Ile Phe Trp Arg Arg Glu Gly Ser Gln Asn
                340                 345                 350

Leu Leu Phe Ser Tyr Gln Pro Pro Gln Ser Ser Ser Arg Phe Ser Val
            355                 360                 365

Ser Gln Thr Gly Asp Leu Thr Val Thr Asn Val Gln Arg Ser Asp Val
    370                 375                 380

Gly Tyr Tyr Ile Cys Gln Thr Leu Asn Val Ala Gly Ser Ile Ile Thr
385                 390                 395                 400

Lys Ala Tyr Leu Glu Val Thr Asp Val Ile Ala Asp Arg Pro Pro
                405                 410                 415
```

```
Val Ile Arg Gln Gly Pro Val Asn Gln Thr Val Ala Val Asp Gly Thr
            420                 425                 430

Leu Thr Leu Ser Cys Val Ala Thr Gly Ser Pro Val Pro Thr Ile Leu
        435                 440                 445

Trp Arg Lys Asp Gly Val Leu Val Ser Thr Gln Asp Ser Arg Ile Lys
    450                 455                 460

Gln Leu Glu Ser Gly Val Leu Gln Ile Arg Tyr Ala Lys Leu Gly Asp
465                 470                 475                 480

Thr Gly Arg Tyr Thr Cys Thr Ala Ser Thr Pro Ser Gly Glu Ala Thr
                485                 490                 495

Trp Ser Ala Tyr Ile Glu Val Gln Glu Phe Gly Val Pro Val Gln Pro
            500                 505                 510

Pro Arg Pro Thr Asp Pro Asn Leu Ile Pro Ser Ala Pro Ser Lys Pro
        515                 520                 525

Glu Val Thr Asp Val Ser Lys Asn Thr Val Thr Leu Leu Trp Gln Pro
    530                 535                 540

Asn Leu Asn Ser Gly Ala Thr Pro Thr Ser Tyr Ile Ile Glu Ala Phe
545                 550                 555                 560

Ser His Ala Ser Gly Ser Ser Trp Gln Thr Val Ala Glu Asn Val Lys
                565                 570                 575

Thr Glu Thr Phe Ala Ile Lys Gly Leu Lys Pro Asn Ala Ile Tyr Leu
            580                 585                 590

Phe Leu Val Arg Ala Ala Asn Ala Tyr Gly Ile Ser Asp Pro Ser Gln
        595                 600                 605

Ile Ser Asp Pro Val Lys Thr Gln Asp Val Pro Pro Thr Thr Gln Gly
    610                 615                 620

Val Asp His Lys Gln Val Gln Arg Glu Leu Gly Asn Val Val Leu His
625                 630                 635                 640

Leu His Asn Pro Thr Ile Leu Ser Ser Ser Val Glu Val His Trp
                645                 650                 655

Thr Val Asp Gln Gln Ser Gln Tyr Ile Gln Gly Tyr Lys Ile Leu Tyr
            660                 665                 670

Arg Pro Ser Gly Ala Ser His Gly Glu Ser Glu Trp Leu Val Phe Glu
        675                 680                 685

Val Arg Thr Pro Thr Lys Asn Ser Val Val Ile Pro Asp Leu Arg Lys
    690                 695                 700

Gly Val Asn Tyr Glu Ile Lys Ala Arg Pro Phe Phe Asn Glu Phe Gln
705                 710                 715                 720

Gly Ala Asp Ser Glu Ile Lys Phe Ala Lys Thr Leu Glu Glu Ala Pro
                725                 730                 735

Ser Ala Pro Pro Arg Ser Val Thr Val Ser Lys Asn Asp Gly Asn Gly
            740                 745                 750

Thr Ala Ile Leu Val Thr Trp Gln Pro Pro Glu Asp Thr Gln Asn
        755                 760                 765

Gly Met Val Gln Glu Tyr Lys Val Trp Cys Leu Gly Asn Glu Thr Arg
    770                 775                 780

Tyr His Ile Asn Lys Thr Val Asp Gly Ser Thr Phe Ser Val Val Ile
785                 790                 795                 800

Pro Ser Leu Val Pro Gly Ile Arg Tyr Ser Val Glu Val Ala Ala Ser
                805                 810                 815

Thr Gly Ala Gly Pro Gly Val Lys Ser Glu Pro Gln Phe
            820                 825
```

-continued

```
<210> SEQ ID NO 26
<211> LENGTH: 506
<212> TYPE: PRT
<213> ORGANISM: Rattus norvegicus

<400> SEQUENCE: 26

Met Ile Ala Glu Pro Ala His Phe Tyr Leu Phe Gly Leu Ile Cys Leu
1               5                   10                  15

Cys Ser Gly Ser Arg Leu Arg Gln Glu Asp Phe Pro Pro Arg Ile Val
                20                  25                  30

Glu His Pro Ser Asp Leu Ile Val Ser Lys Gly Glu Pro Ala Thr Leu
            35                  40                  45

Asn Cys Lys Ala Glu Gly Arg Pro Thr Pro Thr Ile Glu Trp Tyr Lys
        50                  55                  60

Gly Gly Glu Arg Val Glu Thr Asp Lys Asp Asp Pro Arg Ser His Arg
65                  70                  75                  80

Met Leu Leu Pro Ser Gly Ser Leu Phe Phe Leu Arg Ile Val His Gly
                85                  90                  95

Arg Lys Ser Arg Pro Asp Glu Gly Val Tyr Ile Cys Val Ala Arg Asn
                100                 105                 110

Tyr Leu Gly Glu Ala Val Ser His Asn Ala Ser Leu Glu Val Ala Ile
            115                 120                 125

Leu Arg Asp Asp Phe Arg Gln Asn Pro Ser Asp Val Met Val Ala Val
        130                 135                 140

Gly Glu Pro Ala Val Met Glu Cys Gln Pro Pro Arg Gly His Pro Glu
145                 150                 155                 160

Pro Thr Ile Ser Trp Lys Lys Asp Gly Ser Pro Leu Asp Asp Lys Asp
                165                 170                 175

Glu Arg Ile Thr Ile Arg Gly Gly Lys Leu Met Ile Thr Tyr Thr Arg
                180                 185                 190

Lys Ser Asp Ala Gly Lys Tyr Val Cys Val Gly Thr Asn Met Val Gly
            195                 200                 205

Glu Arg Glu Ser Glu Val Ala Glu Leu Thr Val Leu Glu Arg Pro Ser
        210                 215                 220

Phe Val Lys Arg Pro Ser Asn Leu Ala Val Thr Val Asp Asp Ser Ala
225                 230                 235                 240

Glu Phe Lys Cys Glu Ala Arg Gly Asp Pro Val Pro Thr Val Arg Trp
                245                 250                 255

Arg Lys Asp Asp Gly Glu Leu Pro Lys Ser Arg Tyr Glu Ile Arg Asp
                260                 265                 270

Asp His Thr Leu Lys Ile Arg Lys Val Thr Ala Gly Asp Met Gly Ser
            275                 280                 285

Tyr Thr Cys Val Ala Glu Asn Met Val Gly Lys Ala Glu Ala Ser Ala
        290                 295                 300

Thr Leu Thr Val Gln Glu Pro Pro His Phe Val Val Lys Pro Arg Asp
305                 310                 315                 320

Gln Val Val Ala Leu Gly Arg Thr Val Thr Phe Gln Cys Glu Ala Thr
                325                 330                 335

Gly Asn Pro Gln Pro Ala Ile Phe Trp Arg Arg Glu Gly Ser Gln Asn
                340                 345                 350

Leu Leu Phe Ser Tyr Gln Pro Pro Gln Ser Ser Arg Phe Ser Val
            355                 360                 365

Ser Gln Thr Gly Asp Leu Thr Val Thr Asn Val Gln Arg Ser Asp Val
        370                 375                 380
```

```
Gly Tyr Tyr Ile Cys Gln Thr Leu Asn Val Ala Gly Ser Ile Ile Thr
385                 390                 395                 400

Lys Ala Tyr Leu Glu Val Thr Asp Val Ile Ala Asp Arg Pro Pro Pro
            405                 410                 415

Val Ile Arg Gln Gly Pro Val Asn Gln Thr Val Ala Val Asp Gly Thr
        420                 425                 430

Leu Thr Leu Ser Cys Val Ala Thr Gly Ser Pro Val Pro Thr Ile Leu
            435                 440                 445

Trp Arg Lys Asp Gly Val Leu Val Ser Thr Gln Asp Ser Arg Ile Lys
        450                 455                 460

Gln Leu Glu Ser Gly Val Leu Gln Ile Arg Tyr Ala Lys Leu Gly Asp
465                 470                 475                 480

Thr Gly Arg Tyr Thr Cys Thr Ala Ser Thr Pro Ser Gly Glu Ala Thr
                485                 490                 495

Trp Ser Ala Tyr Ile Glu Val Gln Glu Phe
                500                 505

<210> SEQ ID NO 27
<211> LENGTH: 225
<212> TYPE: PRT
<213> ORGANISM: Rattus norvegicus

<400> SEQUENCE: 27

Met Ile Ala Glu Pro Ala His Phe Tyr Leu Phe Gly Leu Ile Cys Leu
1               5                   10                  15

Cys Ser Gly Ser Arg Leu Arg Gln Glu Asp Phe Pro Pro Arg Ile Val
            20                  25                  30

Glu His Pro Ser Asp Leu Ile Val Ser Lys Gly Glu Pro Ala Thr Leu
        35                  40                  45

Asn Cys Lys Ala Glu Gly Arg Pro Thr Pro Thr Ile Glu Trp Tyr Lys
    50                  55                  60

Gly Gly Glu Arg Val Glu Thr Asp Lys Asp Asp Pro Arg Ser His Arg
65                  70                  75                  80

Met Leu Leu Pro Ser Gly Ser Leu Phe Phe Leu Arg Ile Val His Gly
                85                  90                  95

Arg Lys Ser Arg Pro Asp Glu Gly Val Tyr Ile Cys Val Ala Arg Asn
            100                 105                 110

Tyr Leu Gly Glu Ala Val Ser His Asn Ala Ser Leu Glu Val Ala Ile
        115                 120                 125

Leu Arg Asp Asp Phe Arg Gln Asn Pro Ser Asp Val Met Val Ala Val
    130                 135                 140

Gly Glu Pro Ala Val Met Glu Cys Gln Pro Pro Arg Gly His Pro Glu
145                 150                 155                 160

Pro Thr Ile Ser Trp Lys Lys Asp Gly Ser Pro Leu Asp Asp Lys Asp
                165                 170                 175

Glu Arg Ile Thr Ile Arg Gly Gly Lys Leu Met Ile Thr Tyr Thr Arg
            180                 185                 190

Lys Ser Asp Ala Gly Lys Tyr Val Cys Val Gly Thr Asn Met Val Gly
        195                 200                 205

Glu Arg Glu Ser Glu Val Ala Glu Leu Thr Val Leu Glu Arg Pro Ser
    210                 215                 220

Phe
225

<210> SEQ ID NO 28
```

<211> LENGTH: 200
<212> TYPE: PRT
<213> ORGANISM: Rattus norvegicus

<400> SEQUENCE: 28

```
Phe Thr Ser Leu His Phe Val Ser Glu Pro Ser Asp Ala Val Thr Met
1               5                   10                  15

Arg Gly Gly Asn Val Leu Leu Asn Cys Ser Ala Glu Ser Asp Arg Gly
            20                  25                  30

Val Pro Val Ile Lys Trp Lys Lys Asp Gly Leu Ile Leu Ala Leu Gly
        35                  40                  45

Met Asp Asp Arg Lys Gln Gln Leu Pro Asn Gly Ser Leu Leu Ile Gln
    50                  55                  60

Asn Ile Leu His Ser Arg His His Lys Pro Asp Glu Gly Leu Tyr Gln
65                  70                  75                  80

Cys Glu Ala Ser Leu Gly Asp Ser Gly Ser Ile Ile Ser Arg Thr Ala
                85                  90                  95

Lys Val Met Val Ala Gly Pro Leu Arg Phe Leu Ser Gln Thr Glu Ser
            100                 105                 110

Ile Thr Ala Phe Met Gly Asp Thr Val Leu Leu Lys Cys Glu Val Ile
        115                 120                 125

Gly Asp Pro Met Pro Thr Ile His Trp Gln Lys Asn Gln Gln Asp Leu
    130                 135                 140

Asn Pro Ile Pro Gly Asp Ser Arg Val Val Leu Pro Ser Gly Ala
145                 150                 155                 160

Leu Gln Ile Ser Arg Leu Gln Pro Gly Asp Ser Gly Val Tyr Arg Cys
                165                 170                 175

Ser Ala Arg Asn Pro Ala Ser Thr Arg Thr Gly Asn Glu Ala Glu Val
            180                 185                 190

Arg Ile Leu Ser Asp Pro Gly Leu
        195                 200
```

<210> SEQ ID NO 29
<211> LENGTH: 380
<212> TYPE: PRT
<213> ORGANISM: Rattus norvegicus

<400> SEQUENCE: 29

```
Phe Thr Ser Leu His Phe Val Ser Glu Pro Ser Asp Ala Val Thr Met
1               5                   10                  15

Arg Gly Gly Asn Val Leu Leu Asn Cys Ser Ala Glu Ser Asp Arg Gly
            20                  25                  30

Val Pro Val Ile Lys Trp Lys Lys Asp Gly Leu Ile Leu Ala Leu Gly
        35                  40                  45

Met Asp Asp Arg Lys Gln Gln Leu Pro Asn Gly Ser Leu Leu Ile Gln
    50                  55                  60

Asn Ile Leu His Ser Arg His His Lys Pro Asp Glu Gly Leu Tyr Gln
65                  70                  75                  80

Cys Glu Ala Ser Leu Gly Asp Ser Gly Ser Ile Ile Ser Arg Thr Ala
                85                  90                  95

Lys Val Met Val Ala Gly Pro Leu Arg Phe Leu Ser Gln Thr Glu Ser
            100                 105                 110

Ile Thr Ala Phe Met Gly Asp Thr Val Leu Leu Lys Cys Glu Val Ile
        115                 120                 125

Gly Asp Pro Met Pro Thr Ile His Trp Gln Lys Asn Gln Gln Asp Leu
    130                 135                 140
```

-continued

Asn Pro Ile Pro Gly Asp Ser Arg Val Val Leu Pro Ser Gly Ala
145                 150                 155                 160

Leu Gln Ile Ser Arg Leu Gln Pro Gly Asp Ser Gly Val Tyr Arg Cys
            165                 170                 175

Ser Ala Arg Asn Pro Ala Ser Thr Arg Thr Gly Asn Glu Ala Glu Val
            180                 185                 190

Arg Ile Leu Ser Asp Pro Gly Leu His Arg Gln Leu Tyr Phe Leu Gln
            195                 200                 205

Arg Pro Ser Asn Val Ile Ala Ile Glu Gly Lys Asp Ala Val Leu Glu
            210                 215                 220

Cys Cys Val Ser Gly Tyr Pro Pro Pro Ser Phe Thr Trp Leu Arg Gly
225                 230                 235                 240

Glu Glu Val Ile Gln Leu Arg Ser Lys Lys Tyr Ser Leu Leu Gly Gly
            245                 250                 255

Ser Asn Leu Leu Ile Ser Asn Val Thr Asp Asp Ser Gly Thr Tyr Tyr
            260                 265                 270

Thr Cys Val Val Thr Tyr Lys Asn Glu Asn Ile Ser Ala Ser Ala Glu
            275                 280                 285

Leu Thr Val Leu Val Pro Pro Trp Phe Leu Asn His Pro Ser Asn Leu
290                 295                 300

Tyr Ala Tyr Glu Ser Met Asp Ile Glu Phe Glu Cys Ala Val Ser Gly
305                 310                 315                 320

Lys Pro Val Pro Thr Val Asn Trp Met Lys Asn Gly Asp Val Val Ile
            325                 330                 335

Pro Ser Asp Tyr Phe Gln Ile Val Gly Gly Ser Asn Leu Arg Ile Leu
            340                 345                 350

Gly Val Val Lys Ser Asp Glu Gly Phe Tyr Gln Cys Val Ala Glu Asn
            355                 360                 365

Glu Ala Gly Asn Ala Gln Ser Ser Ala Gln Leu Ile
            370                 375                 380

<210> SEQ ID NO 30
<211> LENGTH: 71
<212> TYPE: DNA
<213> ORGANISM: Artificial sequence
<220> FEATURE:
<223> OTHER INFORMATION: synthetic sequence

<400> SEQUENCE: 30
cgcgtccccg ccgccacatt tcgtggtaaa ttcaagagat ttacaacgaa atgtggcggc    60
tttttggaaa t                                                        71

<210> SEQ ID NO 31
<211> LENGTH: 69
<212> TYPE: DNA
<213> ORGANISM: Artificial sequence
<220> FEATURE:
<223> OTHER INFORMATION: synthetic sequence

<400> SEQUENCE: 31
cgatttccaa aaagccgcca catttcgttg taaatctctt gaatttacaa cgaaatgtgg    60
cggcgggga                                                           69

<210> SEQ ID NO 32
<211> LENGTH: 71
<212> TYPE: DNA
<213> ORGANISM: Artificial sequence

```
<220> FEATURE:
<223> OTHER INFORMATION: synthetic sequence

<400> SEQUENCE: 32
cgcgtccccc tgcgataatg cgaggaagat ttcaagagaa tcttcctctc attatcgcag    60
tttttggaaa t                                                         71

<210> SEQ ID NO 33
<211> LENGTH: 69
<212> TYPE: DNA
<213> ORGANISM: Artificial sequence
<220> FEATURE:
<223> OTHER INFORMATION: synthetic sequence

<400> SEQUENCE: 33
cgatttccaa aaactgcgat aatgcgagga agattctctt gaaatcttcc tcgcattatc    60
gcaggggga                                                            69

<210> SEQ ID NO 34
<211> LENGTH: 86
<212> TYPE: DNA
<213> ORGANISM: Artificial sequence
<220> FEATURE:
<223> OTHER INFORMATION: synthetic sequence

<400> SEQUENCE: 34
cgcgtccccc cattcgctct gtagtaatag gtggctgttc aagagacaag ccacctatta    60
ctacagagcg aatggttttt ggaaat                                         86

<210> SEQ ID NO 35
<211> LENGTH: 85
<212> TYPE: DNA
<213> ORGANISM: Artificial sequence
<220> FEATURE:
<223> OTHER INFORMATION: synthetic sequence

<400> SEQUENCE: 35
cgatttccaa aaaccattcg ctctgtagta ataggtggct tgtctcttga acaagccacc    60
tattactaca gagccaatgg gggga                                          85

<210> SEQ ID NO 36
<211> LENGTH: 20
<212> TYPE: DNA
<213> ORGANISM: Artificial sequence
<220> FEATURE:
<223> OTHER INFORMATION: synthetic sequence

<400> SEQUENCE: 36
gtgggtccta acgcagtgtc                                                20

<210> SEQ ID NO 37
<211> LENGTH: 21
<212> TYPE: DNA
<213> ORGANISM: Artificial sequence
<220> FEATURE:
<223> OTHER INFORMATION: synthetic sequence

<400> SEQUENCE: 37
acaaaggcgc aatccaatat g                                              21

<210> SEQ ID NO 38
<211> LENGTH: 20
<212> TYPE: DNA
```

```
<213> ORGANISM: Artificial sequence
<220> FEATURE:
<223> OTHER INFORMATION: synthetic sequence

<400> SEQUENCE: 38
tgagctgaga aggctggtac                                                   20

<210> SEQ ID NO 39
<211> LENGTH: 20
<212> TYPE: DNA
<213> ORGANISM: Artificial sequence
<220> FEATURE:
<223> OTHER INFORMATION: synthetic sequence

<400> SEQUENCE: 39
accccaaact ccgatagtcc                                                   20

<210> SEQ ID NO 40
<211> LENGTH: 20
<212> TYPE: DNA
<213> ORGANISM: Artificial sequence
<220> FEATURE:
<223> OTHER INFORMATION: synthetic sequence

<400> SEQUENCE: 40
ccgcatcaac agtagccttt                                                   20

<210> SEQ ID NO 41
<211> LENGTH: 20
<212> TYPE: DNA
<213> ORGANISM: Artificial sequence
<220> FEATURE:
<223> OTHER INFORMATION: synthetic sequence

<400> SEQUENCE: 41
tgcaagacct cagctttctc                                                   20

<210> SEQ ID NO 42
<211> LENGTH: 22
<212> TYPE: DNA
<213> ORGANISM: Artificial sequence
<220> FEATURE:
<223> OTHER INFORMATION: synthetic sequence

<400> SEQUENCE: 42
tctgccaaac caacgaggag tg                                                22

<210> SEQ ID NO 43
<211> LENGTH: 22
<212> TYPE: DNA
<213> ORGANISM: Artificial sequence
<220> FEATURE:
<223> OTHER INFORMATION: synthetic sequence

<400> SEQUENCE: 43
agaagccagc tttcggaaca cc                                                22

<210> SEQ ID NO 44
<211> LENGTH: 22
<212> TYPE: DNA
<213> ORGANISM: Artificial sequence
<220> FEATURE:
<223> OTHER INFORMATION: synthetic sequence

<400> SEQUENCE: 44
gagtcggaga acatctgtgg ca                                                22
```

<210> SEQ ID NO 45
<211> LENGTH: 22
<212> TYPE: DNA
<213> ORGANISM: Artificial sequence
<220> FEATURE:
<223> OTHER INFORMATION: synthetic sequence

<400> SEQUENCE: 45
cttctcagag cacatgggct tg                                          22

<210> SEQ ID NO 46
<211> LENGTH: 21
<212> TYPE: DNA
<213> ORGANISM: Artificial sequence
<220> FEATURE:
<223> OTHER INFORMATION: synthetic sequence

<400> SEQUENCE: 46
gctcttcgtg agcaccagaa c                                           21

<210> SEQ ID NO 47
<211> LENGTH: 23
<212> TYPE: DNA
<213> ORGANISM: Artificial sequence
<220> FEATURE:
<223> OTHER INFORMATION: synthetic sequence

<400> SEQUENCE: 47
ccacccattc ttttcactcg gac                                         23

<210> SEQ ID NO 48
<211> LENGTH: 22
<212> TYPE: DNA
<213> ORGANISM: Artificial sequence
<220> FEATURE:
<223> OTHER INFORMATION: synthetic sequence

<400> SEQUENCE: 48
agacaacgac gacttcgagg ag                                          22

<210> SEQ ID NO 49
<211> LENGTH: 23
<212> TYPE: DNA
<213> ORGANISM: Artificial sequence
<220> FEATURE:
<223> OTHER INFORMATION: synthetic sequence

<400> SEQUENCE: 49
gtaccatcca gaggaggtgc aac                                         23

<210> SEQ ID NO 50
<211> LENGTH: 23
<212> TYPE: DNA
<213> ORGANISM: Artificial sequence
<220> FEATURE:
<223> OTHER INFORMATION: synthetic sequence

<400> SEQUENCE: 50
ttatggtgat gtggacctta gta                                         23

<210> SEQ ID NO 51
<211> LENGTH: 21
<212> TYPE: DNA
<213> ORGANISM: Artificial sequence
<220> FEATURE:

```
<223> OTHER INFORMATION: synthetic sequence

<400> SEQUENCE: 51
ggttgtatgg gatggttgga g                                              21

<210> SEQ ID NO 52
<211> LENGTH: 22
<212> TYPE: DNA
<213> ORGANISM: Artificial sequence
<220> FEATURE:
<223> OTHER INFORMATION: synthetic sequence

<400> SEQUENCE: 52
accctgcctt tgagcatcag ac                                             22

<210> SEQ ID NO 53
<211> LENGTH: 22
<212> TYPE: DNA
<213> ORGANISM: Artificial sequence
<220> FEATURE:
<223> OTHER INFORMATION: synthetic sequence

<400> SEQUENCE: 53
gcttgtactg gtcgcagcag aa                                             22

<210> SEQ ID NO 54
<211> LENGTH: 20
<212> TYPE: DNA
<213> ORGANISM: Artificial sequence
<220> FEATURE:
<223> OTHER INFORMATION: synthetic sequence

<400> SEQUENCE: 54
catggccttc cgtgttccta                                                20

<210> SEQ ID NO 55
<211> LENGTH: 22
<212> TYPE: DNA
<213> ORGANISM: Artificial sequence
<220> FEATURE:
<223> OTHER INFORMATION: synthetic sequence

<400> SEQUENCE: 55
cctgcttcac caccttcttg at                                             22
```

COMPOSITIONS AND METHODS USEFUL IN PROMOTING MILK PRODUCTION

CROSS-REFERENCE TO RELATED APPLICATIONS

This application claims priority benefit of U.S. Provisional Patent Application No. 62/837,590, filed Apr. 23, 2019, which application is incorporated herein by reference in its entirety.

INCORPORATION BY REFERENCE OF SEQUENCE LISTING PROVIDED AS A TEXT FILE

A sequence listing is provided herewith as a text file, UCSC-383PRV2_seq_list_ST25.txt, created on Feb. 15, 2019, and having a size of 130 KB. The text file is herein incorporated by reference in its entirety.

INTRODUCTION

The mammary gland, or breast, is a dynamic epithelial organ responsible for the production of milk in mammals 1. Beginning as an anlage located at the nipple, the mammary gland develops postnatally in response to hormonal cues produced during puberty, forming ductal structures that branch into the underlying stromal fat pad. Each duct is bilayered, comprising an outer layer of basal/myoepithelial cells (which are referred to herein as BCs) and an inner layer of luminal cells (which are referred to herein as LCs). The luminal cells can be further subdivided into two subpopulations: a ductal subpopulation that encloses the lumen, and an alveolar subpopulation from which milk-producing alveoli are generated during pregnancy (FIG. 1A). Once offspring are weaned off their mother's milk, the mammary gland is remodeled to its pre-pregnancy state in a process called involution. Within the alveolar cell subpopulation, there are alveolar progenitor cells (AVPs). It is currently thought that the generation of alveoli during pregnancy results from the differentiation of alveolar progenitors into the milk-producing alveolar cells (AVs).

Notch is a major signaling pathway that regulates stem/progenitor cell maintenance and fate decisions. There are four NOTCH receptors: NOTCH1, NOTCH2, NOTCH3, and NOTCH4—all of which are expressed in the mammary gland 2. During mammary gland development, Notch signaling promotes luminal cell fates at the expense of basal cell fates[3-6]. In addition, inhibition of NOTCH4 activity appears to be required for alveolar expansion and differentiation due to results in studies showing that overexpression of constitutively active NOTCH4 intracellular domain (ICD) greatly diminishes alveolar development[7-9]. This indicates that signaling through NOTCH4 must be inhibited in alveolar progenitor cells for them to differentiate into alveolar cells.

Roundabout (ROBO) receptors are conserved immunoglobulin (Ig) superfamily members that participate in numerous developmental processes. They bind to a family of conserved, secreted, glycoprotein extracellular matrix ligands called SLITs (e.g. SLIT2 and SLIT3 in the mammary gland), which are expressed throughout the mammary gland epithelium (FIG. 1B)[10,11]. This signaling system has been shown to regulate cell fate decisions in the murine nervous system and *Drosophila* intestine[12,13].

SUMMARY

To build a milk supply with every pregnancy requires significantly accelerated cell growth and differentiation. Disclosed herein are methods of promoting that accelerated cell growth and differentiation by treating with agents that affect a disinhibitory signaling circuit whereby ROBO2 inhibits ROBO1, which in turn inhibits NOTCH4 activation. ROBO1 is expressed on both BCs and LCs in the virgin mammary gland, but is upregulated in LCs during pregnancy. ROBO2 expression is restricted to a subset of luminal cells. Disclosed herein for the first time are the following findings: Loss (or deletion) of the Robo1 gene results in inhibition of mammary gland alveolar differentiation. This has been demonstrated in both the HC11 cell lactation model, and in vivo in the mammary gland. Loss (or deletion) of Robo2 results in the opposite phenotype in both models—i.e. greater mammary gland alveolar differentiation. ROBO1 has been shown to specifically bind to NOTCH4 and inhibit its signaling. ROBO2 has been shown to specifically bind to ROBO1 and prevent ROBO1 from inhibiting NOTCH4. The interaction between ROBO1 and ROBO2 is potentiated by SLIT2. Disclosed herein are ROBO1 receptor fragments, comprising portions of the ROBO1 extracellular domain that inhibit NOTCH4 signaling. The experiments disclosed herein demonstrate that SLIT/ROBO signaling regulates mammary alveologenesis by governing NOTCH4 activation and controlling the number of alveolar progenitor cells that differentiate into milk-producing alveolar cells.

Methods, agents, and compositions for promoting milk production in a mammal are provided. Agents useful for promoting milk production may include an agent that inhibits NOTCH4 activity. The agent may be a soluble ROBO1 extracellular domain or the agent may inhibit NOTCH4 activity by binding to ROBO2 and/or by binding to NOTCH4. The agent may inhibit NOTCH4 by competing with ROBO1 from binding to ROBO2, thereby making ROBO1 available to inhibit NOTCH4 activity. The agent may be an anti-NOTCH4 antibody that inhibits NOTCH4 activity. The agent may be an RNAi construct that inhibits expression of NOTCH4. The agent may be an RNAi construct that inhibits expression of ROBO2. Also provided herein are transgenic mammals genetically modified for expression of a soluble ROBO1 extracellular domain; inhibition of expression of ROBO2; and/or inhibition of expression of NOTCH4. Methods for promoting milk production in such transgenic mammals by administering one or more of the agents disclosed herein are also provided.

SEQUENCE LISTING

Figure 1:
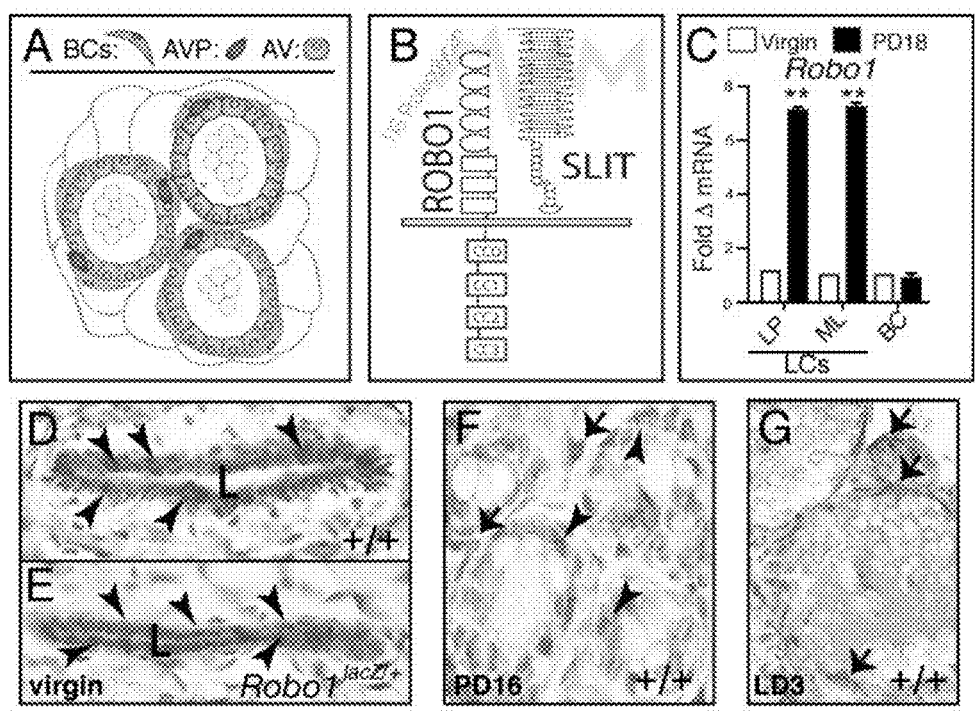
FIG. 1: ROBO1 expression. (A) Cartoon of bilayered alveoli comprising basal (myoepithelial and stem) (BC), luminal alveolar progenitor (AVP) and alveolar (AV) cells. (B) Cartoon of SLIT/ROBO1. (C) RT-qPCR of Robo1 in virgin and PD18 luminal progenitor (LP), mature luminal (ML) and basal (BC) cells shows upregulation in luminal cells (LCs) during pregnancy (n=3). (D-G) ROBO1 immunohistochemistry (D) or β-galactosidase (LacZ) staining (E) in a subpopulation of luminal cells (arrowheads) in mature virgin ducts (D,E) and PD16 alveoli (F). ROBO1 is also expressed in basal cells (arrows) in PD16 (F) and lactation day (LD3) (G) alveoli. (SEM, t-test p<0.01).

SEQ ID NO: 1—*Bos taurus* ROBO1-Ecto
SEQ ID NO: 2—*Bos taurus* ROBO1-Ig5
SEQ ID NO: 3—*Bos taurus*—ROBO1-Ig2
SEQ ID NO: 4—*Homo sapiens* ROBO1-Ecto
SEQ ID NO: 5—*Homo sapiens* ROBO1-Ig5
SEQ ID NO: 6—*Homo sapiens* ROBO1-Ig2
SEQ ID NO: 7—*Bison bison* ROBO1-Ecto
SEQ ID NO: 8—*Bison bison* ROBO1-Ig5
SEQ ID NO: 9—*Bison bison* ROBO1-Ig2
SEQ ID NO 10—*Camelus bactrianus* ROBO1-Ecto
SEQ ID NO: 11—*Camelus bactrianus* ROBO1-Ig5
SEQ ID NO: 12—*Camelus bactrianus* ROBO1-Ig2
SEQ ID NO: 13—*Capra hircus* ROBO1-Ecto
SEQ ID NO: 14—*Capra hircus* ROBO1-Ig5
SEQ ID NO: 15—*Capra hircus* ROBO1-Ig2

SEQ ID NO: 16—*Ovis aries* ROBO1-Ecto
SEQ ID NO: 17—*Ovis aries* ROBO1-Ig5
SEQ ID NO: 18—*Ovis aries* ROBO1-Ig2
SEQ ID NO: 19—*Bos Mutas* ROBO1-Ecto
SEQ ID NO: 20—*Bos Mutas* ROBO1-Ig5
SEQ ID NO: 21—*Bos Mutas* ROBO1-Ig2
SEQ ID NO: 22—*Mus musculus* ROBO1-Ecto
SEQ ID NO: 23—*Mus musculus* ROBO1-Ig5
SEQ ID NO: 24—*Mus musculus* ROBO1-Ig2
SEQ ID NO: 25—*Rattus norvegicus* ROBO1-Ecto
SEQ ID NO: 26—*Rattus norvegicus* ROBO1-Ig5
SEQ ID NO: 27—*Rattus norvegicus* ROBO1-Ig2
SEQ ID NO: 28—*Rattus norvegicus* DCC Ig2
SEQ ID NO: 29—*Rattus norvegicus* DCC Ig4
SEQ ID NO: 30—Robo1 shRNA forward strand
SEQ ID NO: 31—Robo1 shRNA reverse strand
SEQ ID NO: 32—Notch4 shRNA forward strand
SEQ ID NO: 33—Notch4 shRNA reverse strand
SEQ ID NO: 34—Robo2 shRNA forward strand
SEQ ID NO: 35—Robo2 shRNA reverse strand

DETAILED DESCRIPTION

Methods, agents, and compositions for promoting milk production in a mammal are provided. Agents useful for promoting milk production may include an agent that inhibits NOTCH4 activity. The agent may be a soluble ROBO1 extracellular domain, the agent may inhibit NOTCH4 activity by binding to ROBO2 and/or by binding to NOTCH4. The agent may inhibit NOTCH4 by competing with ROBO1 from binding to ROBO2, thereby making ROBO1 available to inhibit NOTCH4 activity. The agent may be an anti-NOTCH4 antibody that inhibits NOTCH4 activity. The agent may be an RNAi construct that inhibits expression of NOTCH4. The agent may be an RNAi construct that inhibits expression of ROBO2. Also provided herein are transgenic mammals genetically modified for expression of a soluble ROBO1 extracellular domain; inhibition of expression of ROBO2; and/or inhibition of expression of NOTCH4. Methods for promoting milk production in such transgenic mammals by administering one or more of the agents disclosed herein are also provided.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present methods, compositions, and transgenic mammals are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual aspects described and illustrated herein has discrete components and features which may be readily separated from or combined with the features of any of the other several aspects without departing from the scope or spirit of the present methods. Any recited method can be carried out in the order of events recited or in any other order that is logically possible.

Definitions

The term "antibody" as used herein refers to an immunoglobulin molecule that recognizes and binds a target through at least one antigen-binding site. "Antibody" is used herein in the broadest sense and encompasses various antibody structures, including but not limited to, polyclonal antibodies, recombinant antibodies, monoclonal antibodies, chimeric antibodies (e.g., chimera of antibody sequences from two or more different species, such as, human, bovine, ovine, caprine, camelid, etc.), humanized antibodies, human antibodies, bovinized antibodies, ovinized antibodies, caprinized antibodies, camelidized antibodies, bispecific antibodies, multispecific antibodies, diabodies, tribodies, tetrabodies, single chain Fv (scFv) antibodies, single domain antibodies (e.g., camelid/lama antibodies), and antibody fragments.

The term "intact antibody" or "full-length antibody" refers to an antibody having a structure substantially similar to a native antibody structure. This includes an antibody comprising two light chains each comprising a variable region and a light chain constant region (CL) and two heavy chains each comprising a variable region and at least heavy chain constant regions CH1, CH2, and CH3.

The term "antibody fragment" as used herein refers to a molecule other than an intact antibody that comprises a portion of an antibody and generally an antigen-binding site. Examples of antibody fragments include, but are not limited to, Fab, Fab', F(ab')2, Fv, disulfide-linked Fv (sdFv), Fd, linear antibodies, single chain antibody molecules (e.g., scFv), diabodies, tribodies, tetrabodies, minibodies, dual variable domain antibodies (DVD), single variable domain antibodies, and multispecific antibodies formed from antibody fragments.

The term "variable region" as used herein refers to the region of an antibody light chain or the region of an antibody heavy chain that is involved in binding the antibody to antigen. The variable region of an antibody heavy chain and an antibody light chain have similar structures, and generally comprise four framework regions and three complementarity determining regions (CDRs) (also known as hypervariable regions).

The term "framework regions" refers to amino acid residues other than the CDR residues within a variable region. The variable region generally comprises four framework regions, FR1, FR2, FR3, and FR4.

The term "monoclonal antibody" as used herein refers to a substantially homogenous antibody population involved in the highly specific recognition and binding of a single antigenic determinant or epitope. The individual antibodies comprising the population are identical, except for possible naturally occurring mutations that may be present in minor amounts. The term "monoclonal antibody" encompasses intact and full-length monoclonal antibodies as well as antibody fragments (e.g., Fab, Fab', F(ab')2, Fv), single chain (scFv) antibodies, fusion proteins comprising an antibody fragment, and any other modified immunoglobulin molecule comprising an antigen-binding site. Furthermore, "monoclonal antibody" refers to such antibodies made by any number of techniques, including but not limited to, hybridoma production, phage library display, recombinant expression, and transgenic animals.

The term "chimeric antibody" as used herein refers to an antibody in which a portion of the heavy and/or light chain is derived from a particular source or species, while the remainder of the heavy and/or light chain is derived from a different source or species.

The term "humanized antibody" as used herein refers to a chimeric antibody that generally comprises human immunoglobulins (e.g., recipient antibody) in which the native CDR residues are replaced by residues from corresponding CDRs from a nonhuman species (e.g., donor antibody) such as mouse, rat, rabbit, or nonhuman primate, wherein the donor antibody has the desired specificity, affinity, and/or activity. In some instances, one or more residues within one or more framework regions of the human immunoglobulin are replaced by corresponding nonhuman residues. Furthermore, humanized antibodies can comprise residues that are not found in the recipient antibody or in the donor antibody. These modifications may be made to further refine and/or optimize antibody characteristics. A humanized antibody may comprise variable regions containing all or substantially all of the CDRs that correspond to those of a nonhuman immunoglobulin and all or substantially all of the framework regions that correspond to those of a human immunoglobulin. In some aspects, the humanized antibody will comprise at least a portion of an immunoglobulin Fc region (e.g., hinge region, CH1, CH2, and/or CH3), typically that of a human immunoglobulin. Similar definition applies to bovinized, ovinized, caprinized, and camelized antibodies.

The term "human antibody" as used herein refers to an antibody that possesses an amino acid sequence that corresponds to an antibody produced by a human and/or an antibody that has been made using any of the techniques that are known to those of skill in the art for making human antibodies. These techniques include, but not limited to, phage display libraries, yeast display libraries, transgenic animals, and B-cell hybridoma technology. A human antibody as defined herein excludes a humanized antibody comprising residues from a non-human source.

The terms "epitope" and "antigenic determinant" are used interchangeably herein and refer to that portion of an antigen or target capable of being recognized and bound by a particular binding agent or binding agent (e.g., an antibody). When the antigen or target is a polypeptide, epitopes can be formed both from contiguous amino acids and noncontiguous amino acids juxtaposed by tertiary folding of the protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5, 6, 7, or 8-10 amino acids in a unique spatial conformation. Epitopes can be predicted using any one of a large number of software bioinformatic tools available on the internet. X-ray crystallography may be used to characterize an epitope on a target protein by analyzing the amino acid residue interactions of an antigen/antibody complex.

The term "specifically binds" as used herein refers to a binding agent (e.g., an antibody) that interacts more frequently, more rapidly, with greater duration, with greater affinity, or with some combination of the above to a particular antigen, epitope, protein, or target molecule than with alternative substances. An antibody that specifically binds an antigen can be identified, for example, by immunoassays, ELISAs, surface plasmon resonance (SPR) technology (e.g., Biacore), FACS, or other techniques known to those of ordinary skill in the art.

The terms "polypeptide" and "peptide" and "protein" are used interchangeably herein and refer to polymers of amino acids of any length. The term "peptide" may be used to refer to a polymer of less than 50 amino acids, e.g., 5-50 amino acids. The polymer may be linear or branched, it may comprise modified amino acids, and it may be interrupted by non-amino acids. The terms also encompass an amino acid polymer that has been modified naturally or by intervention; for example, by disulfide bond formation, glycosylation, lipidation, acetylation, phosphorylation, or any other manipulation or modification. Also included within the definition are, for example, polypeptides containing one or more analogs of an amino acid, including but not limited to, unnatural amino acids, as well as other modifications known in the art. It is understood that, because some of the polypeptides of this disclosure may be based upon antibodies, the term "polypeptide" encompasses polypeptides as a single chain and polypeptides of two or more associated chains.

The terms "polynucleotide" and "nucleic acid" and "nucleic acid molecule" are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variants thereof. In some aspects, two polynucleotides or polypeptides of the disclosure are substantially identical, meaning they have at least 70%, at least 75%, at least 80%, at least 85%, at least 90%, and in some aspects at least 95%, 96%, 97%, 98%, 99% nucleotide or amino acid residue identity, when compared and aligned for maximum correspondence, as measured using a sequence comparison algorithm or by visual inspection. In some aspects, identity exists over a region of the sequences that is at least about 10, at least about 20, at least about 40-60 nucleotides or amino acid residues, at least about 60-80 nucleotides or amino acid residues in length, or any integral value there between. In some aspects, identity exists over a longer region than 60-80 nucleotides or amino acid residues, such as at least about 80-100 nucleotides or amino acid residues, and in some aspects the sequences are substantially identical over the full length of the sequences being compared, for example, (i) the coding region of a nucleotide sequence or (ii) an amino acid sequence.

The phrase "conservative amino acid substitution" as used herein refers to a substitution in which one amino acid residue is replaced with another amino acid residue having a similar side chain. Families of amino acid residues having similar side chains have been generally defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is considered to be a conservative substitution. Generally, conservative substitutions in the sequences of polypeptides and/or antibodies do not abrogate the binding of the polypeptide or antibody to the target binding site. Methods of identifying nucleotide and amino acid conservative substitutions that do not eliminate binding are well-known in the art.

The term "vector" as used herein means a construct, which is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

The term "isolated" as used herein refers to a polypeptide, peptide, soluble protein, antibody, polynucleotide, vector, cell, or composition that is in a form not found in nature. An "isolated" antibody is substantially free of material from the cellular source from which it is derived. In some aspects, isolated polypeptides, peptides, soluble proteins, antibodies, polynucleotides, vectors, cells, or compositions are those which have been purified to a degree that they are no longer in a form in which they are found in nature. In some aspects, a polypeptide, peptide, soluble protein, antibody, polynucleotide, vector, cell, or composition that is isolated is substantially pure. A polypeptide, peptide, soluble protein, antibody, polynucleotide, vector, cell, or composition may be isolated from a natural source or from a source such as an engineered cell line.

The term "substantially pure" as used herein refers to material which is at least 50% pure (i.e., free from contaminants), at least 90% pure, at least 95% pure, at least 98% pure, or at least 99% pure.

As used herein, the term "derived" in the context of a polypeptide refers to a polypeptide that has a sequence that is based on that of a protein from a particular source. A polypeptide derived from a protein from a particular source may be a variant of the protein from the particular source. For example, a polypeptide derived from a protein from a particular source may have a sequence that is modified with respect to the protein's sequence from which it is derived. A polypeptide derived from a protein from a particular source shares at least 50% sequence identity with, at least 60% sequence identity with, at least 70% sequence identity with, at least 80% sequence identity with, or at least 90% sequence identity with the protein from which it is derived.

The term "effective amount" as used herein refers to the amount of an agent (e.g., an antibody, polypeptide, nucleic acid, etc.) which is sufficient to produce an intended effect in a subject, such as mammal.

As used herein, reference to "about" or "approximately" a value or parameter includes (and describes) aspects that are directed to that value or parameter. For example, a description referring to "about X" includes description of "X".

As used in the present disclosure and claims, the singular forms "a", "an" and "the" include plural forms unless the context clearly dictates otherwise.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following aspects: A, B, and C; A, B, or C; A or C; A or B; B or C; A and C; A and B; and B and C; A (alone); B (alone); and C (alone).

As used herein, the term RNAi construct encompasses RNA molecules and vectors whose presence within a cell results in RNA interference (RNAi) and leads to reduced expression of a transcript to which the RNAi construct is targeted. The term includes siRNA, shRNA, and RNAi-inducing vectors.

As used herein, an RNAi-inducing vector is a vector whose presence within a cell results in transcription of one or more RNAs that self-hybridize or hybridize to each other to form an shRNA or siRNA. This term encompasses plasmids, e.g., DNA vectors or viral vectors. The vector may include a nucleic acid operably linked to expression signal(s) so that one or more RNA molecules that hybridize or self-hybridize to form an siRNA or shRNA are transcribed when the vector is present within a cell. Thus the vector provides a template for intracellular synthesis of the RNA or RNAs or precursors thereof.

A short, interfering RNA (siRNA) comprises an RNA duplex that is approximately 19 base pairs long and optionally further comprises one or two single-stranded overhangs. An siRNA may be formed from two RNA molecules that hybridize together, or may alternatively be generated from a single RNA molecule that includes a self-hybridizing portion. The duplex portion of an siRNA may, include one or more unpaired nucleotides. One strand of an siRNA includes a portion that hybridizes with a target transcript with perfect complementary or one or two mismatches. In aspects where perfect complementarity is not achieved, any mismatches may be located at or near the siRNA termini.

The term short hairpin RNA refers to an RNA molecule comprising at least two complementary portions hybridized or capable of hybridizing to form a double-stranded (duplex) structure sufficiently long to mediate RNAi (typically at least 19 base pairs in length), and at least one single-stranded portion, typically between approximately 1 and 10 nucleotides in length that forms a loop. The duplex portion may, but typically does not, contain one or more bulges consisting of one or more unpaired nucleotides.

Disclosed herein is an examination of the role of ROBO receptors during mammary alveologenesis. In particular, the loss of Robo1 inhibits alveologenesis and the loss of Robo2 enhances alveologenesis. Biochemical studies in cell lines are disclosed that reveal that ROBO1 specifically binds NOTCH4 and inhibits NOTCH4 activation. ROBO1 is shown to be broadly expressed throughout the mammary gland epithelial compartment, while expression of ROBO2 is restricted to alveolar progenitor cells and basal/myoepithelial cells (BCs). Also disclosed are ROBO1 receptor fragments, comprising portions of the ROBO1 extracellular domain (ECD) that inhibit NOTCH4 signaling and promote alveologenesis. It is also disclosed that alveologenesis is enhanced by treatment of cells and mammals with antibodies that inhibit ROBO2 binding to ROBO1. Without being bound by theory, the findings disclosed herein indicate a disinhibitory circuit mechanism (ROBO2-|ROBO1-|NOTCH4) that regulates NOTCH4 signaling and, consequently, the number of alveolar progenitor cells that differentiate into milk-producing alveoli with each pregnancy.

Methods for Enhancing Milk Production in a Mammal

The present disclosure provides methods of promoting milk production in a mammal. In certain aspects, the method may include administering to the mammal a first agent that inhibits NOTCH4 activity, wherein the first agent is administered in an amount sufficient to inhibit NOTCH4 activity, thereby promoting milk production. The first agent may inhibit NOTCH4 activity by directly binding to NOTCH4 protein, by inhibiting the binding of ROBO2 to ROBO1, by promoting the binding of ROBO1 to NOTCH4, by inhibiting the expression of NOTCH4, or by inhibiting the expression of ROBO2.

In certain aspects, the first agent may comprise a soluble ROBO1 extracellular domain (ECD). In certain aspects, the soluble ROBO1 ECD may include the entire extracellular domain of ROBO1 or a ROBO2 binding fragment thereof. In certain aspects, the soluble ROBO1 ECD may include at least two immunoglobulin (Ig) domains of ROBO1, e.g., the first two Ig domains of ROBO1. In certain aspects, the soluble ROBO1 ECD may be include at least five immunoglobulin domains of ROBO1. In certain aspects, the soluble ROBO1 ECD may be derived from the extracellular domain of a murine, bovine, ovine, caprine, or human ROBO1. In certain aspects, the soluble ROBO1 ECD may include an amino acid sequence at least 70%, at least 80%, at least 90%, at least 92%, at least 93%, at least 94%, at least 95%, at least 96%, at least 97%, at least 98%, at least 99%, or a 100% identical to the amino acid sequence set forth in any one of SEQ ID NOs:1-27. In certain aspects, the soluble ROBO1 ECD may include the sequence of any one of SEQ ID NOs:1-27 with one or more (e.g., 1, 2, 3, 4, 5, 6, 7, 8, 9, 10, or up to 20) conservative amino acid substitutions thereto. In certain aspects, the soluble ROBO1 ECD administered to the mammal may be derived from the sequence of ROBO1 protein expressed by the mammal, to reduce an immune response to the soluble ROBO1 ECD.

A soluble ROBO1 ECD that may include the entire extracellular region of ROBO1 or a ROBO2 binding fragment thereof may be identified by any means. For example, soluble ROBO1 ECD effective in inhibiting NOTCH4 activity may be identified by performing an assay for measuring binding of the soluble ROBO1 ECD to ROBO2. The assay may include determining whether soluble ROBO1 ECD binds to ROBO2 in the presence of a competitor, such as, a full length ROBO1 or a soluble ROBO1 ECD having the amino acid sequence set forth in any one of SEQ ID NOs. 1-27. In certain aspects, soluble ROBO1 ECD effective in inhibiting NOTCH4 activity may be identified by performing an assay for measuring binding of the soluble ROBO1 ECD to NOTCH4. Binding of soluble ROBO1 ECD to ROBO2 and/or NOTCH4 may be measured by detecting formation of a ROBO1 ECD::ROBO2 complex and/or ROBO1 ECD::NOTCH4 complex. Other methods for identifying binding of a soluble ROBO1 ECD to ROBO2 and/or NOTCH4 may also be used.

In some aspects, soluble ROBO1 fused or linked to a heterologous polypeptide. In some aspects, the heterologous polypeptide is linked to the amino-terminus, the carboxyl-terminus, or both termini of the soluble ROBO1 ECD. As used herein, the term soluble used in the context of ROBO1 ECD means that the ROBO1 ECD is not localized ECD described herein can be and is not able to localized to the cell surface since it is missing the transmembrane region required for cell surface localization. The soluble ROBO1 ECD is also devoid of the sequence of the intracellular region of ROBO1. In certain aspects, the soluble ROBO1 ECD polypeptide may be fused to an immunoglobulin Fc polypeptide (e.g., human IgG Fc, such as IgG1 Fc), a serum albumin (e.g., human serum albumin, cynomolgus serum albumin or bovine serum albumin), or maltose binding protein. In certain aspects, the soluble ROBO1 ECD may be fused to a protein tag that facilitates purification or tracking of the polypeptide. Such proteins tags include His tag, a hemagglutinin tag, a Fc region (derived from an Ig from a human, bovine, ovine, or caprine antibody, e.g., IgG, IgM, IgA, IgE, or IgD), or a Myc tag.

In some aspects, the first agent may be an anti-NOTCH4 antibody or a NOTCH4 binding fragment thereof that inhibits NOTCH4 activity. As used herein, the term antibody encompasses antigen-binding fragment thereof unless the context clearly dictates otherwise. In some aspects, the antibody comprises a plurality of polyclonal antibodies that bind to different epitopes on the antigen. In some aspects, the antibody is a recombinant antibody. In some aspects, the antibody is a monoclonal antibody. In some aspects, the antibody is a chimeric antibody. In certain aspects, the antibody is modified to provide for decreased immunogenicity in the mammal receiving the antibody. In some aspects, the antibody is a humanized antibody. In some aspects, the antibody is a human antibody. In some aspects, the antibody is a bovinized antibody. In some aspects, the antibody is a bovine antibody. In some aspects, the antibody is an ovinized antibody. In some aspects, the antibody is an ovine antibody. In some aspects, the antibody is a caprinized antibody. In some aspects, the antibody is a caprine antibody. In some aspects, the antibody is a camelized antibody. In some aspects, the antibody is a camelid antibody. In some aspects, the antibody is an IgA, IgD, IgE, IgG, or IgM antibody. In some aspects, the antibody is an IgG antibody. In some aspects, the antibody is an IgG1, IgG2, IgG3, or IgG4 antibody. In some aspects, the antibody is an antibody fragment comprising at least one antigen-binding site. In some aspects, the antibody is a scFv. In some aspects, the antibody is a disulfide-linked scFv. In some aspects, the antibody is a Fab. In some aspects, the antibody is a bispecific antibody or a multispecific antibody.

In some aspects, the first agent is a polyclonal antibody that binds to NOTCH4. Polyclonal antibodies can be prepared by any method known to those of skill in the art. In some aspects, polyclonal antibodies are produced by immunizing an animal (e.g., a cow, sheep, camel, rabbit, rat, mouse, goat, donkey) with an antigen of interest (e.g., a purified peptide fragment, a recombinant protein, or a fusion protein) using multiple subcutaneous or intraperitoneal injections. In some aspects, the antigen is conjugated to a carrier such as keyhole limpet hemocyanin (KLH), serum albumin, bovine thyroglobulin, or soybean trypsin inhibitor. The antigen (with or without a carrier protein) is diluted in sterile saline and usually combined with an adjuvant (e.g., Complete or Incomplete Freund's Adjuvant) to form a stable emulsion. After a period of time, polyclonal antibodies are recovered from the immunized animal (e.g., from blood or ascites). In some aspects, the polyclonal antibodies are purified from serum or ascites according to standard methods in the art including, but not limited to, affinity chromatography, ion-exchange chromatography, gel electrophoresis, and/or dialysis.

In some aspects, first agent is a monoclonal antibody that binds to NOTCH4. Monoclonal antibodies can be prepared by any method known to those of skill in the art. In some aspects, monoclonal antibodies are prepared using hybridoma methods known to one of skill in the art. A mouse, rat, rabbit, hamster, or other appropriate host animal, is immunized as described above. In some aspects, lymphocytes are immunized in vitro. In some aspects, the immunizing antigen is a human protein or a fragment thereof. Following immunization, lymphocytes are isolated and fused with a suitable myeloma cell line using, for example, polyethylene glycol. The hybridoma cells are selected using specialized media as known in the art and unfused lymphocytes and myeloma cells do not survive the selection process. Hybridomas that produce monoclonal antibodies directed to a chosen antigen can be identified by a variety of methods including, but not limited to, immunoprecipitation, immunoblotting, and in vitro binding assays (e.g., flow cytometry, FACS, ELISA, SPR (e.g., Biacore), and radioimmunoassay). Once hybridoma cells that produce antibodies of the desired specificity, affinity, and/or activity are identified, the clones may be subcloned by limiting dilution or other techniques. The hybridomas can be propagated either in in vitro culture using standard methods or in vivo as ascites tumors in an animal. The monoclonal antibodies can be purified from the culture medium or ascites fluid according to standard methods in the art including, but not limited to, affinity chromatography, ion-exchange chromatography, gel electrophoresis, and dialysis.

In some aspects, monoclonal antibodies are made using recombinant DNA techniques as known to one skilled in the art. For example, the polynucleotides encoding an antibody are isolated from mature B-cells or hybridoma cells, such as by RT-PCR using oligonucleotide primers that specifically amplify the genes encoding the heavy and light chains of the antibody and their sequence is determined using standard techniques. The isolated polynucleotides encoding the heavy and light chains are then cloned into suitable expression vectors that produce the monoclonal antibodies when transfected into host cells such as *E. coli*, simian COS cells, Chinese hamster ovary (CHO) cells, or myeloma cells that do not otherwise produce immunoglobulin proteins.

In some aspects, recombinant monoclonal antibodies are isolated from phage display libraries expressing variable domains or CDRs of a desired species (e.g., cow or human). Screening of phage libraries can be accomplished by various techniques known in the art.

In some aspects, a monoclonal antibody is modified by using recombinant DNA technology to generate alternative antibodies. In some aspects, the constant domains of the light chain and heavy chain of a mouse monoclonal antibody are replaced with the constant regions of a human antibody, ovine antibody, bovine antibody, caprine antibody, or camelid antibody to generate a chimeric antibody. In some aspects, the constant regions are truncated or removed to generate a desired antibody fragment of a monoclonal antibody. In some aspects, site-directed or high-density mutagenesis of the variable region(s) is used to optimize specificity and/or affinity of a monoclonal antibody.

In some aspects the anti-NOTCH4 antibody is a humanized antibody. Various methods for generating humanized antibodies are known in the art. In some aspects, a humanized antibody comprises one or more amino acid residues that have been introduced into its sequence from a source that is non-human. In some aspects, humanization is performed by substituting one or more amino acids of a CDR sequence of a human antibody with the corresponding amino acids from a non-human antibody (e.g., a mouse antibody). In some aspects, the humanized antibodies are constructed by substituting all six CDRs of a human antibody with corresponding amino acids from the CDRs of a non-human antibody (e.g., a mouse antibody).

The choice of which human heavy chain variable region and/or light chain variable region are used for generating humanized antibodies can be made based on a variety of factors and by a variety of methods known in the art. In some aspects, the "best-fit" method is used where the sequence of the variable region of a non-human (e.g., rodent) antibody is screened against the entire library of known human variable region sequences. The human sequence that is most similar to that of the non-human (e.g., rodent) sequence is selected as the human variable region framework for the humanized antibody. In some aspects, a particular variable region framework derived from a consensus sequence of all human antibodies of a particular subgroup of light or heavy chains is selected as the variable region framework. In some aspects, the variable region framework sequence is derived from the consensus sequences of the most abundant human subclasses. In some aspects, human germline genes are used as the source of the variable region framework sequences.

In some aspects, the anti-NOTCH4 antibody is a human antibody. Human antibodies can be prepared using various techniques known in the art. In some aspects, human antibodies are generated from immortalized human B lymphocytes immunized in vitro. In some aspects, human antibodies are generated from lymphocytes isolated from an immunized individual. In any case, cells that produce an antibody directed against a target antigen can be generated and isolated. In some aspects, a human antibody is selected from a phage library, where that phage library expresses human antibodies. Alternatively, phage display technology may be used to produce human antibodies and antibody fragments in vitro, from immunoglobulin variable region gene repertoires from unimmunized donors. Techniques for the generation and use of antibody phage libraries are well-known in the art. Once antibodies are identified, affinity maturation strategies known in the art, including but not limited to, chain shuffling and site-directed mutagenesis, may be employed to generate higher affinity human antibodies. In some aspects, human antibodies are produced in transgenic mice that contain human immunoglobulin loci. Upon immunization these mice are capable of producing the full repertoire of human antibodies in the absence of endogenous immunoglobulin production.

In certain aspects, the antibodies may be bovinized antibodies or fully bovine antibodies. Methods for producing a bovinized antibody from a non-bovine antibody may comprise forming a chimeric antibody that retains CDRs from the non-bovine antibody while other regions of the antibody may be replaced with corresponding sequences from a bovine antibody. introducing one or more amino acid residues into it from a bovine antibody. In certain aspects, the non-bovine antibody may be bovinized by replacing the constant regions with constant regions from a bovine antibody. In certain aspects, the non-bovine antibody may be bovinized by replacing the constant regions with constant regions from a bovine antibody and replacing the framework regions with framework regions from a bovine antibody. In certain aspects, a bovinized antibody may be generated by replacing the CDRS of a bovine antibody with the CDRs from a non-bovine antibody. In certain cases, the antibody may be a fully bovine antibody that is produced using gene sequences encoding a bovine antibody. A fully bovine antibody may be produced in a bovine, in a bovine cell line, in a non-bovine cell lines genetically modified to express bovine antibodies, or in a transgenic non-bovine animal genetically modified to express bovine antibodies. Similar methods may be used to generate species specific antibodies that when administered to the species produces reduced immune response to the antibody. For example, ovinized antibodies, caprinized antibodies, camelized antibodies may be produced for purpose of administering the antibody to an ovine, caprine, and camelid, respectively.

CDRs of an antibody are defined by those skilled in the art using a variety of methods/systems. These systems and/or definitions have been developed and refined over a number of years and include Kabat, Chothia, IMGT, AbM, and Contact. The Kabat definition is based on sequence variability and is commonly used. The Chothia definition is based on the location of the structural loop regions. The IMGT system is based on sequence variability and location within the structure of the variable domain. The AbM definition is a compromise between Kabat and Chothia. The Contact definition is based on analyses of the available antibody crystal structures. An Exemplary system is a combination of Kabat and Chothia. Software programs (e.g., abYsis) are available and known to those of skill in the art for analysis of antibody sequence and determination of CDRs.

The specific CDR sequences defined herein are generally based on a combination of Kabat and Chothia definitions (Exemplary system). However, it will be understood that reference to a heavy chain CDR or CDRs and/or a light chain CDR or CDRs of a specific antibody will encompass all CDR definitions as known to those of skill in the art.

In some aspects, an anti-NOTCH4 antibody comprises an antibody in which at least one or more of the constant regions has been modified or deleted. In some aspects, the antibodies may comprise modifications to one or more of the three heavy chain constant regions (CH1, CH2 or CH3) and/or to the light chain constant region (CL). In some aspects, the heavy chain constant region of the modified antibodies comprises at least one human constant region. In some aspects, the heavy chain constant region of the modified antibodies comprises more than one human constant region. In some aspects, modifications to the constant region comprise additions, deletions, or substitutions of one or more amino acids in one or more regions. In some aspects, one or more regions are partially or entirely deleted from the constant regions of the modified antibodies. In some aspects, the entire CH2 domain has been removed from an antibody (ΔCH2 constructs). In some aspects, a deleted constant region is replaced by a short amino acid spacer that provides some of the molecular flexibility typically imparted by the absent constant region. In some aspects, a modified antibody comprises a CH3 domain directly fused to the hinge region of the antibody. In some aspects, a modified antibody comprises a peptide spacer inserted between the hinge region and modified CH2 and/or CH3 domains.

It is known in the art that the constant region(s) of an antibody mediates several effector functions and these effector functions can vary depending on the isotype of the antibody. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can be involved in autoimmune hypersensitivity. In addition, the Fc region of an antibody can bind a cell expressing a Fc receptor (FcR). There are a number of Fc receptors that are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell cytotoxicity or ADCC), release of inflammatory mediators, placental transfer, and control of immunoglobulin production.

In some aspects, an anti-NOTCH4 antibody comprises a variant Fc region. The amino acid sequences of the Fc region of human IgG1, IgG2, IgG3, and IgG4 are known to those of ordinary skill in the art. In some aspects, the variant Fc region provide for altered effector functions that, in turn, affect the biological profile of the antibody. For example, in some aspects, the deletion or inactivation (through point mutations or other means) of a constant region reduces or eliminates Fc receptor binding of the modified antibody as it circulates. In some aspects, the constant region modifications increase the serum half-life of the antibody. In some aspects, the constant region modifications reduce the serum half-life of the antibody. In some aspects, the constant region modifications decrease, reduce, or remove ADCC and/or complement dependent cytotoxicity (CDC) of the antibody. In some aspects, specific amino acid substitutions in a human IgG1 Fc region with corresponding IgG2 or IgG4 residues may reduce effector functions (e.g., ADCC and CDC) in the modified antibody. In some aspects, an antibody does not have one or more effector functions. In some aspects, the antibody has no ADCC activity and/or no CDC activity. In some aspects, the antibody does not bind an Fc receptor and/or complement factors. In some aspects, the antibody has no effector function(s) (e.g., "effectorless" antibodies). In some aspects, the constant region modifications increase or enhance effector functions of the antibody. In some aspects, the constant region modifications increase or enhance ADCC and/or CDC of the antibody. In some aspects, the constant region is modified to eliminate disulfide linkages or oligosaccharide moieties. In some aspects, the constant region is modified to add/substitute one or more amino acids to provide one or more cytotoxin, oligosaccharide, or carbohydrate attachment sites.

Modifications to the constant region of antibodies described herein may be made using well-known biochemical or molecular engineering techniques. In some aspects, antibody variants are prepared by introducing appropriate nucleotide changes into the encoding DNA, and/or by synthesis of the desired antibody or polypeptide. Using this technique, it may be possible to disrupt the activity or effector function provided by a specific sequence or region while substantially maintaining the structure, binding activity, and other desired characteristics of the modified antibody.

The present disclosure further embraces additional variants and equivalents that are substantially homologous to the recombinant, monoclonal, chimeric, humanized, and human antibodies, or antibody fragments thereof, described herein. In some aspects, it is desirable to improve the binding affinity of the antibody. In some aspects, it is desirable to modulate biological properties of the antibody, including but not limited to, specificity, thermostability, expression level, effector function(s), glycosylation, immunogenicity, and/or solubility. Those skilled in the art will appreciate that amino acid changes may alter post-translational processes of an antibody, such as changing the number or position of glycosylation sites or altering membrane anchoring characteristics. Variations may be a substitution, deletion, or insertion of one or more nucleotides encoding the antibody or polypeptide that results in a change in the amino acid sequence as compared with the native antibody or polypeptide sequence. In some aspects, amino acid substitutions are the result of replacing one amino acid with another amino acid having similar structural and/or chemical properties, such as the replacement of a leucine with a serine, e.g., conservative amino acid replacements. The variant antibodies or polypeptides described herein may be generated using methods known in the art, including but not limited to, site-directed mutagenesis, alanine scanning mutagenesis, and PCR mutagenesis.

In some aspects, an agent that inhibits NOTCH4 activity as described herein is chemically modified. In some aspects, the soluble ROBO1 ECD and/or the anti-NOTCH4 antibody that has been chemically modified by glycosylation, acetylation, pegylation, phosphorylation, amidation, derivatization by known protecting/blocking groups, proteolytic cleavage, and/or linkage to a cellular ligand or other protein. Any of numerous chemical modifications may be carried out by known techniques.

In some aspects, the method may involve increasing milk production in a mammalian species, where the mammalian species comprises human, bovine, ovine, caprine, or camelid and the method may include administering to the mammalian species a soluble ROBO1 ECD derived from a human ROBO1, a bovine ROBO1, a ovine ROBO1, a caprine ROBO1, or a camelid ROBO1, respectively. In certain aspects, the mammal is a female at a stage of development suitable for milk production. For example, the mammal may be a female that has developed mammary glands. In certain aspects, the mammal is a woman, a cow, a doe, an ewe, or a female camel. In certain aspects, the mammal may be pregnant when an agent that inhibits NOTCH4 activity is administered to the mammal. In certain aspects, the mammal may have given birth prior to the administering of an agent that inhibits NOTCH4 activity. For example, the mammal may have given birth within 1-2 years of the administering, e.g., within 3 months, 6 months, 1 year, or 18 months. In other aspects, the mammal is not pregnant. In some aspects, the mammal has not given birth prior to the administering of an agent that inhibits NOTCH4 activity. For example, the mammal has not given birth within 1-2 years of the administering, e.g., within 3 months, 6 months, 1 year, or 18 months.

In some aspects, an agent that inhibits NOTCH4 activity as described herein may be an RNAi construct that binds to NOTCH4 mRNA and decreases expression of NOTCH4. In some aspects, an agent that inhibits ROBO2 activity as described herein may be an RNAi construct that binds to ROBO2 mRNA and decrease expression of ROBO2. The RNAi construct may be a short interfering RNA (siRNA). The siRNA may be a short hairpin RNA (shRNA). The RNAi construct may be a micro RNA (miRNA). Methods for making RNAi constructs to inhibit expression of any known gene sequence are known to those of skill in the art. In certain aspects, the siRNA for decreasing expression of NOTCH4 may include a nucleic acid sequence set forth in SEQ ID NOs: 32 or 33. In certain aspects, the siRNA for decreasing expression of ROBO2 may include a nucleic acid sequence set forth in SEQ ID NOs: 34 or 35. In certain aspects, the RNAi construct may be administered to the mammal. In other aspects, a nucleic acid In certain aspects, the method for promoting milk production in a mammal may involve administering one or more of the agents that inhibit NOTCH4 activity. In certain aspects, the method may include administering at least one of a first agent and a second agent, where the first agent and the second agent is independently selected from a soluble ROBO1 ECD, an anti-NOTCH4 antibody, an RNAi construct that inhibits the expression of NOTCH4, or an RNAi construct that inhibits the expression of ROBO2. In certain aspects, the method may include administering at least one of first agent, a second agent, and a third agent where the first agent, the second agent, and the third agent is independently selected from a soluble ROBO1 ECD, an anti-NOTCH4 antibody, an RNAi construct that inhibits the expression of NOTCH4, or an RNAi construct that inhibits the expression of ROBO2. In certain aspects, the method may include administering a first agent, a second agent, a third agent, and a fourth agent where the first agent, the second agent, the third agent, and the fourth agent is independently selected from a soluble ROBO1 ECD, an anti-NOTCH4 antibody, an RNAi construct that inhibits the expression of NOTCH4, or an RNAi construct that inhibits the expression of ROBO2.

One or more agents for inhibiting NOTCH4 activity may be administered to a mammal for promoting milk production via any suitable route including parenteral (e.g., intramuscular, intravenous, subcutaneous (e.g., injection or implant), intraperitoneal, intracisternal, intraarticular, intraperitoneal, intracerebral (intraparenchymal) and intracerebroventricular), oral, nasal, vaginal, sublingual, intraocular, rectal, topical (e.g., transdermal), sublingual and inhalation. In certain aspects, the one or more agents may be administered via direct injection, e.g., injection into mammary tissue, e.g., intraductal injection.

Agents for Inhibiting NOTCH4 Activity and Compositions Thereof

Also provided herein are agents and compositions thereof that may be used for performing the methods disclosed herein.

In certain aspects, a polypeptide comprising a soluble ROBO1 ECD polypeptide as disclosed herein is provided. The soluble ROBO1 ECD polypeptide may be fused to a heterologous polypeptide as disclosed herein. In certain aspects, a nucleic acid encoding a soluble ROBO1 ECD polypeptide as disclosed herein is provided. Description of soluble ROBO1 ECD polypeptides is provided in the preceding sections and elsewhere herein and is not reiterated here for brevity. A soluble ROBO1 ECD can be produced using methods known in the art. Polypeptides can be produced, in whole or in part, using standard recombinant DNA technology or using chemical methods. Chemical methods for synthesizing polypeptides may involve using various solid-phase techniques that may be performed using an automated peptide synthesizer (e.g., a Biotage instrument). Chemical methods for synthesizing polypeptides may involve using combinatorial methodologies. In addition, polypeptides can be modified by a wide variety of chemical methods known to those of skill in the art. Polypeptide sequence variations, substitutions, and/or modifications can also be made using methods such as site-directed mutagenesis, alanine scanning, and/or PCR-based mutagenesis. Site-directed mutagenesis, cassette mutagenesis, restriction selection mutagenesis, and other techniques can be performed on cloned DNA to produce soluble ROBO1 ECD, variants, fusions, chimeras, and other derivatives thereof. A "produced" or "synthesized" polypeptide sequence is a polypeptide made by any method involving manipulation by the hand of man. Such methods include but are not limited to, chemical synthesis, recombinant DNA technology, biochemical or enzymatic fragmentation of larger molecules, and combinations of the foregoing.

Where a polypeptide, e.g., soluble ROBO1 ECD polypeptide is produced using recombinant techniques, the polypeptide may be produced as an intracellular protein or as a secreted protein, using any suitable construct and any suitable host cell, which can be a prokaryotic or eukaryotic cell, such as a bacterial (e.g., *E. coli*) or a yeast host cell, respectively. In certain aspects, eukaryotic cells that are used as host cells for production of the polypeptide include insect cells, mammalian cells, and/or plant cells. In certain aspects, mammalian host cells are used and may include human cells (e.g., HeLa, 293, H9 and Jurkat cells); mouse cells (e.g., NIH3T3, L cells, and C127 cells); primate cells (e.g., Cos 1, Cos 7 and CV1) and hamster cells (e.g., Chinese hamster ovary (CHO) cells). In specific aspects, the polypeptides disclosed herein are produced in CHO cells or HEK cells. In certain aspects, the polypeptides of the present disclosure, e.g., soluble ROBO1 ECD, are produced in cells cultured in the presence of heparin. For example, about 300 ng/ml of heparin may be included in the culture medium. In other aspects, the polypeptides of the present disclosure, e.g., soluble ROBO1 ECD, are produced in cells cultured in a culture medium not containing significant amounts of heparin, e.g., the culture medium may contain less than 300 ng/ml, 100 ng/ml, 50 ng/ml, 25 ng/ml, 10 ng/ml, or 1 ng/ml heparin, or no heparin.

A variety of host-vector systems suitable for the expression of a polypeptide may be employed according to standard procedures known in the art. See, e.g., Sambrook et al., 1989 Current Protocols in Molecular Biology Cold Spring Harbor Press, New York; and Ausubel et al. 1995 Current Protocols in Molecular Biology, Eds. Wiley and Sons. Methods for introduction of genetic material into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically integrated. A variety of appropriate vectors for use in production of a polypeptide of interest are commercially available.

Vectors can provide for extrachromosomal maintenance in a host cell or can provide for integration into the host cell genome. The expression vector provides transcriptional and translational regulatory sequences and may provide for inducible or constitutive expression where the coding region is operably-linked under the transcriptional control of the transcriptional initiation region, and a transcriptional and translational termination region. In general, the transcriptional and translational regulatory sequences may include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7).

Also provided herein are nucleic acids encoding the polypeptides disclosed herein. In certain aspects, a nucleic acid encoding the polypeptides disclosed herein is operably linked to a promoter sequence that confers expression of the polypeptides. In certain aspects, the sequence of the nucleic acid is codon optimized for expression of the polypeptide in a mammalian cell. In certain aspects, the nucleic acid is a deoxyribonucleic acid (DNA). In certain aspects, the nucleic acid is a ribonucleic acid (RNA). Also provided herein is a vector comprising the nucleic acid encoding the polypeptide for promoting milk productions, as described herein. In certain aspects, the vector is a viral vector.

In certain aspects, an anti-NOTCH4 antibody as disclosed herein is provided. Description of anti-NOTCH4 antibodies is provided in the preceding sections and elsewhere herein and is not reiterated here for brevity. An anti-NOTCH4 antibody for inhibiting NOTCH4 activity may be identified by using any suitable means, such as, assays and/or cells and animal models disclosed herein.

In certain aspects, an RNAi construct that inhibits expression of NOTCH4 or an RNAi construct that inhibits expression of ROBO2 as disclosed herein is provided. Description of such RNAi constructs is provided in the preceding sections and elsewhere herein and is not reiterated here for brevity. RNAi constructs for inhibiting NOTCH4 activity may be identified by using any suitable means, such as, assays and/or cells and animal models disclosed herein.

Also disclosed herein are pharmaceutical compositions comprising one or more inhibitors of NOTCH4 activity as disclosed herein and a pharmaceutically acceptable carrier. The term "pharmaceutically acceptable" as used herein refers to a substance approved or approvable by a regulatory agency or listed in the U.S. Pharmacopeia, European Pharmacopeia, or other generally recognized pharmacopeia for use in animals, including humans.

The terms "pharmaceutically acceptable excipient, carrier, or adjuvant" or "acceptable pharmaceutical carrier" as used herein refer to an excipient, carrier, or adjuvant that can be administered to a subject, together with at least one agent, and which does not have an effect on the pharmacological activity of the agent. In general, those of skill in the art and the U.S. FDA consider a pharmaceutically acceptable excipient, carrier, or adjuvant to be an inactive ingredient of any formulation.

The term "pharmaceutical formulation" or "pharmaceutical composition" as used herein refers to a preparation that is in such form as to permit the biological activity of the agent (e.g., an antibody) to be effective. A pharmaceutical formulation or composition generally comprises additional components, such as a pharmaceutically acceptable excipient, carrier, adjuvant, buffers, etc.

In certain aspects, the polypeptides and the nucleic acids (e.g., encoding the polypeptides or RNAi) are present in a therapeutically effective amount in the pharmaceutical composition. A therapeutically effective amount can be determined based on an observed effectiveness of the composition. A therapeutically effective amount can be determined using assays that measure the desired effect in a cell, e.g., in a reporter cell line in which expression of a reporter is modulated in response to the polypeptides of the present disclosure. The pharmaceutical compositions can be administered ex vivo or in vivo to a mammal in order to practice the methods and uses described herein.

The pharmaceutical compositions of the present disclosure can be formulated to be compatible with the intended method or route of administration; exemplary routes of administration are set forth herein. Suitable pharmaceutically acceptable or physiologically acceptable diluents, carriers or excipients include, but are not limited to, nuclease inhibitors, protease inhibitors, a suitable vehicle such as physiological saline solution or citrate buffered saline.

Solutions or suspensions used for parenteral, intradermal, or subcutaneous administration can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS).

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Formulations for oral delivery may advantageously incorporate agents to improve stability within the gastrointestinal tract and/or to enhance absorption.

For administration by inhalation, the compositions are formulated with a delivery agent for delivery in the form of an aerosol spray from a pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds and delivery agents are formulated into ointments, salves, gels, or creams as generally known in the art. The compositions can also be prepared in the form of suppositories (e.g., with conventional suppository bases such as cocoa butter and other glycerides) or retention enemas for rectal administration.

In one aspect, the compositions are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers.

Oral or parenteral compositions may be formulated in dosage unit form for ease of administration and uniformity of dosage. Dosage unit form as used herein refers to physically discrete units suited as unitary dosages for the intended subject; each unit containing a predetermined quantity of active compound calculated to produce the desired effect in association with the required pharmaceutical carrier.

As described above, nucleic acid molecules that serve as templates for transcription of siRNA or shRNA can be inserted into vectors which can be used as gene therapy vectors. Nucleic acid molecules encoding soluble ROBO1 ECD may also be can be inserted into vectors which can be used as gene therapy vectors. In general, gene therapy vectors can be delivered to a subject by, for example, intravenous injection, local administration, or by stereotactic injection. In certain aspects, compositions comprising gene therapy vectors and a delivery agent may be delivered orally or via inhalation and may be encapsulated or otherwise manipulated to protect them from degradation, etc. The pharmaceutical compositions comprising a gene therapy vector can include an acceptable diluent, or can comprise a slow release matrix in which the gene delivery vehicle is imbedded. Alternatively, where the complete gene delivery vector can be produced intact from recombinant cells, e.g., retroviral or lentiviral vectors, the pharmaceutical preparation can include one or more cells which produce the gene delivery system.

Pharmaceutical compositions can be included in a container, pack, or dispenser together with instructions for administration.

Transgenic Mammals

In certain aspects, a transgenic mammal comprising a genetic modification that results in one or more of the following phenotypes: expression of a soluble ROBO1 extracellular domain; inhibition of expression of ROBO2; and inhibition of expression of NOTCH4 is provided. In certain aspects, the transgenic mammal may be a murine, bovine, ovine, caprine, or camelid.

In certain aspects, the phenotype is limited to mammary tissue. In certain aspects, the phenotype is limited to mammary tissue by using a mammary tissue specific promoter to induce the expression of the phenotype.

In certain aspects, the transgenic mammal may include two genetic modifications that result in two of the listed phenotypes. In certain aspects, the transgenic mammal may include three genetic modifications that result in all three of the listed phenotypes.

In certain aspects, the methods for promoting milk production as disclosed herein may involve administering to the transgenic mammal at least one of the pharmaceutical compositions that inhibits NOTCH4 activity, as disclosed herein.

In certain aspects, the transgenic animal may include a genetic modification that results in expression of a soluble ROBO1 extracellular domain, the method may further include administering the pharmaceutical composition comprising an anti-ROBO1 antibody, and anti-NOTCH4 antibody, or an RNAi construct that inhibition of expression of ROBO2 and/or NOTCH4 to the transgenic animal.

In certain aspects, the transgenic animal may include a genetic modification that results in inhibition of expression of ROBO2 and/or NOTCH4, the method may further include administering to the transgenic animal the pharmaceutical composition comprising a soluble ROBO1 ECD as disclosed herein.

A transgenic mammal may be produced using methods known in the art. Exemplary methods for making a transgenic mammal may include the following steps: 1) producing a gene construct containing a nucleic acid encoding a soluble ROBO1 ECD or a nucleic acid sequence transcribed into a siRNA or shRNA targeting NOTCH4 or ROBO2 under the control of a promoter. The promoter can be a mammary gland specific promoter or a ubiquitously active promoter. 2) transfecting the gene construct into a cell from a mammal, e.g., a cow cell and selecting for transgenic cells that have incorporated the gene construct. 3) fusing (e.g., by applying an electrical pulse) the transgenic cell with an enucleated oocyte from the same species as the transgenic cell (e.g. cow) and allowing the oocyte to develop into an embryo. 4) Transplanting the embryo into a recipient mammal of the same species as the embryo (e.g. cow). 5) Confirming that the embryo developed into a transgenic mammal.

EXPERIMENTAL

ROBO1 is Expressed in Both Luminal and Basal Compartments and Upregulated During Pregnancy:

Previously published studies have focused on the role of SLIT/ROBO1 signaling during the period of branching morphogenesis in the virgin animal,[11,15,16] To investigate the role of ROBO1 during pregnancy, Robo1 mRNA levels in cells isolated from mammary glands were measured using RT qPCR (FIG. 1C). The cells were harvested from adult virgin and pregnant day 18 (PD18) wild type (WT) mice (as indicated in FIG. 1C), and then purified by fluorescent activated cell sorting (FACS) into three subpopulations: luminal progenitor (LP, Lin-CD24$^{lo}$CD29$^+$CD61$^+$), mature luminal (ML, Lin-CD24$^{lo}$CD29$^+$CD61$^-$), and basal (BC, Lin-CD24$^+$CD29$^{hi}$)[17,18]. Results show upregulation of Robo1 in both luminal progenitor and mature luminal, but not basal, subpopulations (FIG. 1C).

To evaluate the expression of ROBO1 and ROBO2 proteins in tissue, immunohistochemistry (FIG. 1D) and β-galactosidase (lacZ) staining (FIG. 1E) was performed on tissue sections from WT and Robo1$^{lacZ/+}$ mature virgin mammary glands from mice. immunohistochemistry and β-gal staining was also performed on pregnant day 16 (PD16) (FIG. 1F) and lactation day 3 (LD3) (FIG. 1G) mammary gland sections. ROBO1 protein is expressed in a subpopulation of luminal cells in mature virgin and pregnant mammary glands (FIG. 1D-F arrowheads). Basal, myoepithelial ROBO1 expression is also observed in pregnant and lactating mammary glands during pregnancy (FIG. 1F, G arrows).

ROBO1 Enhances Alveologenesis:

To investigate ROBO1 function during alveologenesis, Robo1 gene expression was inhibited in HC11 cells (Robo1 KD). HC11 cells are a well-established, prolactin-responsive model of lactation,[19,20] Cells in which Robo1 gene expression was not inhibited are referred to as WT or Robo1+/+ herein. To measure milk production, cells were grown to confluence and then primed by treatment with epidermal growth factor (EGF, 10 ng/ml). The EGF is administered for three days in combination with charcoal-stripped fetal bovine serum, followed by one day of charcoal-stripped fetal bovine serum in the absence of EGF. These primed cells are then differentiated by treatment with dexamethasone (1 µg/ml), insulin (5 µg/ml) and prolactin (Prl, 5 µg/ml) media (DIP media) for between 3 and 5 days (FIG. 2A). Differentiation (Dif) results in the development of milk-filled domes (FIG. 2B). Statistically significantly less milk dome formation and statistically significantly less whey acidic protein (WAP) gene expression was observed in response to treatment with the DIP media (FIG. 2B). If the cells were left undifferentiated (Undif), there was little dome formation in either WT or Robo1–/– cells (FIG. 2B). Next, tissue from Robo1 knockout mice (Robo1–/–) and wild type mice (WT or Robo1+/+) mice was analyzed. Mammary glands were harvested from pregnant day 18 WT and Robo1–/– animals and alveologenesis analyzed by serially sectioning, carmine staining and then quantifying the area occupied by alveoli in sections located at top, middle and bottom portions of the tissue. This analysis revealed significantly reduced alveolar area in the Robo1–/–, compared to WT, mammary glands (FIG. 2C).

To ensure this defect was due to Robo1 inhibition in mammary epithelia and not due to its global deletion that can affect hormone production[21], tissue from Robo1–/– and littermate Robo1+/+ mice were contralaterally transplanted into hosts that had been pre-cleared of endogenous mammary epithelium following standard protocols[22]. After ten weeks, the animals were mated and the tissue examined at pregnant day 18. Significantly less alveolar area was observed in transplanted Robo1–/– KO mammary glands (FIG. 2D), with results similar to those observed in the mammary glands of intact Robo1–/– animals (FIG. 2C). To evaluate the expression of specific markers that are regulated by pregnancy, Robo1–/– and Robo1+/+ tissue was harvested at lactation day 1, RNA extracted and RT-qPCR performed on genes known to be involved in milk production. Significantly lower expression of WAP, Lactalbumin Alpha (Lalba), Xanthine Dehydrogenase (XDH), Butyrophilin (Btn1) was observed in Robo1–/– tissue (FIG. 2E).

Selected markers were further evaluated using immunohistochemistry. WAP expression in Robo1–/– and WT pregnant day 18 mammary glands showed less WAP immunostaining staining in the Robo1–/– tissue (FIG. 2F). Transplanted pregnant day 16 tissue was immunostained with antibodies specific to the lipid binding protein perilipin 2 (PLIN2). Less PLIN2 immunostaining was observed in in Robo1–/– mammary tissue (FIG. 2G).

In addition, whole organ tissue clearing was used to optimize optical clarity and morphological preservation of the tissue. This was followed by dual immunohistochemistry using an antibody specific to the transcription factor ELF5, which is required for alveologenesis 6, and using an antibody specific to the cell-cell adhesion protein E-cadherin (CDH1) (FIG. 2H). Significantly less ELF5 staining was observed in the Robo1–/– relative to Robo1+/+ tissue (FIG. 2H).

Loss of Robo1 Hampers Milk Production In Vivo:

To assess the effect of Robo1 expression on milk production, crosses were performed to generate heterozygous pups that were then fed by either a Robo1–/– or WT dam. Heterozygous pups were generated by crossing a WT male with a Robo1–/– female and by crossing a Robo1–/– male with a WT female. The litter size was restricted to five pups and these pups were weighed daily (FIG. 2I). Heterozygous pups fed by a WT dam gained weight in a linear fashion, whereas heterozygous pups fed by a Robo1–/– dam gained less weight (FIG. 2J).

ROBO1 Interacts with and Inhibits NOTCH4 Signaling:

Notch signaling is exquisitely sensitive to dosage, with the outcome depending on the level of receptor activity[23].

Figure 3:
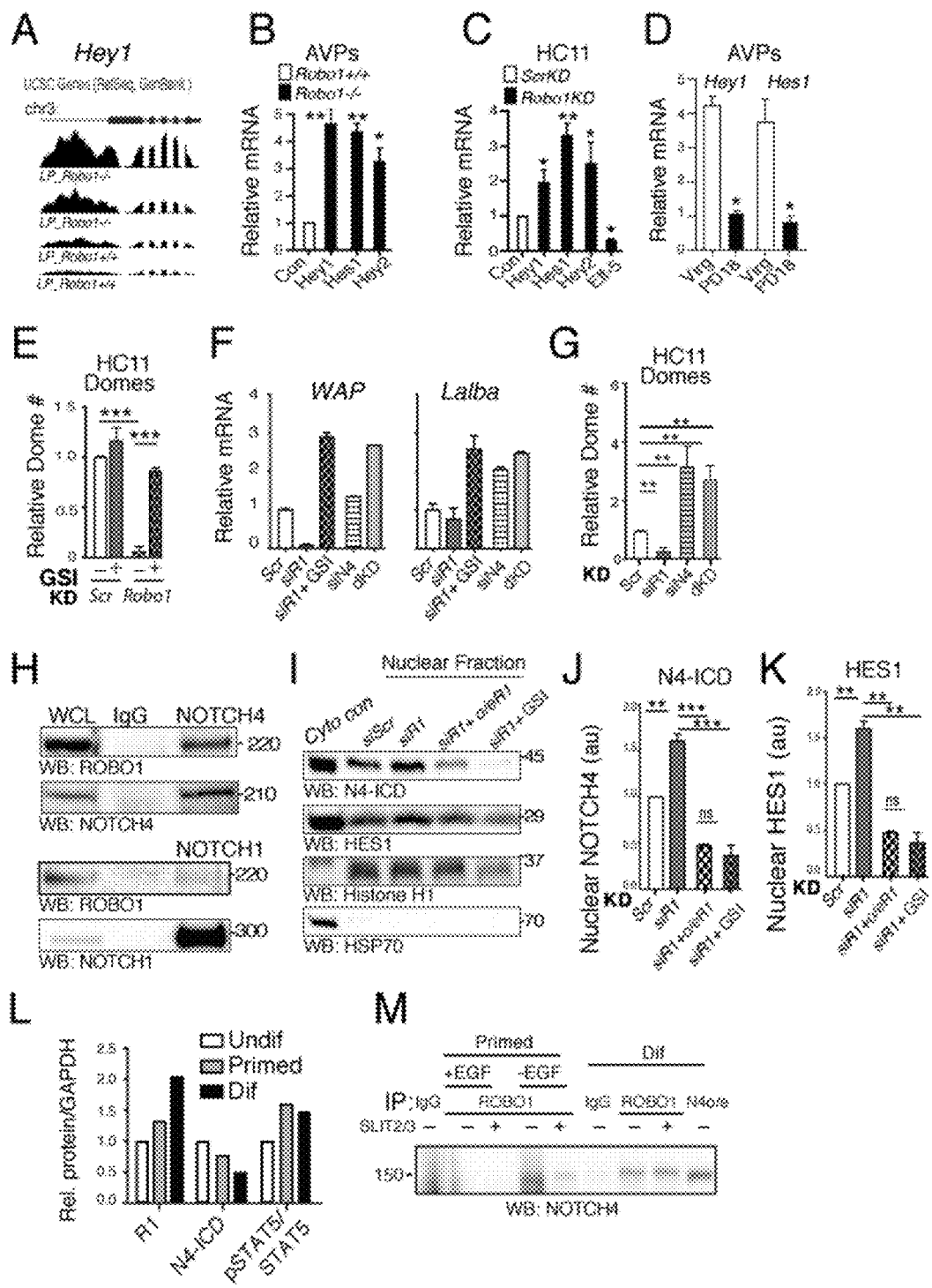
FIG. 3: ROBO1 regulates the activation of NOTCH4 through direct interaction. (A) Genome browser snap shots of Robo1-regulated gene Hey1 with RNA-seq read coverage of Robo1+/+& Robo1−/− luminalprogenitor (LP) samples plotted as a histogram (n=3). (B, C) RT-qPCR validation of Robo1− regulated gene expression shows increased Notch effector genes in Robo1 KO 1° alveolar progenitor cells (AVPs), normalized to WT (B) (n=3), and in Robo1 knockdown HC11 cells, normalized to control (Scr) cells (C) (n=3). (D) RT-qPCR shows significantly reduced expression of Notch effector genes Hey1 and Hes1 in AVPs harvested from pregnant, compared to virgin, mammary glands (n=3). (E) Decreased dome formation in Robo1 knockdown (KD) HC11 cells is rescued by GSI treatment (n=3). (F) Decreased WAP and Lalba expression in Robo1 knockdown (siR1) HC11 cells is rescued by GSI treatment (siR1+GSI). Notch4 knockdown (siN4) increases WAP and Lalba expression, as does double knockdown of both Notch4 and Robo1 (dKD) (n=1). (G) Robo1 decreases HC11 dome formation, a result that is rescued by knockdown of Notch4 and Robo1/Notch4 double knockdown (dKD) (n=2). (H) Endogenous ROBO1 co-immunoprecipitates with NOTCH4, but not NOTCH1 in MDA-MB-231 cell lysates (n=3). (I-K) Cell fractionated Western blot (1) and quantification shows increased NOTCH4 intracellular domain (N4-ICD) (J) and HES1 (K) in the nuclear fraction of Robo1 knockdown (siN4) differentiated HC11 cells. Robo1 overexpression (siR1+R1o/e) and GSI treatment (siR1+GSI) rescues the effect (n=3). (L) Increased ROBO1 and pSTAT5, but decreased NOTCH4 intracellular domain (N4-ICD) are present in differentiated (Dif), compared to undifferentiated (Undif), HC11 cells (n=1). (M) Endogenous NOTCH4 co-immunoprecipitates with ROBO1 from differentiated (Dif) and late stage primed (−EGF) HC11 cells. SLIT does not appear to influence complex formation in differentiated HC11 cells, although decreased complex in observed in late stage (−EGF) primed cells. No ROBO1/NOTCH4 complex is precipitated from early primed cells (+EGF) or when control IgG is used (n=1). (SEM, *$p<0.05$, $p<0.01$, *$p<0.001$).

After ligand binding, Notch receptors are activated by cleavage. First there is an extracellular cleavage, followed by a γ-secretase-mediated, intracellular cleavage that releases the Notch intracellular domain (ICD), which enters the nucleus and regulates transcription. RNA-sequencing analysis of FACS-purified subpopulations isolated from virgin mammary glands reveal higher expression of Notch signaling effector Hey1 in the Robo1−/− luminal progenitor (LP) subpopulation, relative to Robo1+/+(FIG. 3A).

The Sca/CD54 marker was used to enrich alveolar progenitor cells (AVPs) from the FACS-purified pool of luminal progenitor cells. Similar to the data from the bulk luminal progenitor cells (FIG. 3A), RT-qPCR analysis of alveolar progenitor cells (AVPs) revealed significantly greater expression in Robo1−/−, relative to Robo1+/+, of three downstream Notch effectors (Hey1, Hes1 and Hey2) (FIG. 3B). Similarly, in HC11 cells, significantly greater expression of Hey1, Hes1 and Hey2, relative to WT cells, was observed after inhibition of Robo1 expression (FIG. 3C). Inhibition of Robo1 expression in HC11 cells also resulted in significantly lower expression of the pro-differentiation marker Elf5 relative to WT (FIG. 3C). These data show that inhibition of Robo1 expression in both primary cells and tissue culture cells results in the upregulation of Notch effector genes and downregulation of the pro-differentiation Elf5 gene, and further suggests an activation of Notch signaling when ROBO1 is absent.

Previous studies have shown that alveologenesis requires the downregulation of Notch signaling[6], particularly Notch4[7-9]. Alveolar progenitor cells (AVPs) were FACS-purified from virgin (Virg) and pregnant day 18 (PD18) animals and expression of the Notch4 target genes Hes1 and Hey1 examined by RT-qPCR (FIG. 3D). It was observed that both Notch target genes were significantly downregulated in alveolar progenitor cells isolated from glands from pregnant animals, compared to alveolar progenitor cells isolated from glands from virgin animals.

The effect of Notch in the HC11 cell differentiation assay was also assessed. Inhibition of Robo1 expression (KD) resulted in significantly less HC11 milk dome formation relative to controls (Scr) (FIG. 3E). HC11 cells with inhibited Robo1 expression (siR1) also displayed less WAP and Lalba expression relative to controls (Scr) (FIG. 3F). Both these effects were rescued by the treatment of cells with the γ-secretase inhibitor (GSI, R04929097) (siR1+GSI) (FIG. 3E, F). This γ-secretase inhibitor acts to prevent Notch signaling, further supporting the notion that loss of Robo1 enhances Notch4 signaling, causing effects that can be rescued by γ-secretase treatment.

In additional experiments, Notch4 expression was inhibited in HC11 cells (siN4). These cells displayed greater WAP and Lalba expression relative to control cells (Scr). In still other experiments both Robo1 and Notch4 expression were inhibited in HC11 cells (dKD), resulting in increased WAP and Lalba expression relative to control cells (Scr), similar to the levels of WAP and Lalba expression observed with Robo1 inhibition plus GSI treatment (siR1+GSI) (FIG. 3F). Notch4 knockdown resulted in significantly higher dome number relative to control cells (Scr) (FIG. 3G)—a result that is consistent with the greater expression in milk genes (FIG. 3F). These data support a model that NOTCH4 inhibits alveologenesis. Inhibiting the expression of Robo1 (siR1) resulted in significantly fewer milk domes formed, relative to control cells (Scr) (FIG. 3G), but simultaneous inhibition of both Robo1 and Notch4 expression (dKD) resulted in more milk domes formed—the same effect observed with inhibition of Notch4 expression alone (siN4), (FIG. 3G). Together, these data suggest that ROBO1 and NOTCH4 function in the same pathway to regulate alveologenesis with ROBO1 inhibiting NOTCH4, and NOTCH4 inhibiting alveologenesis.

Notch receptor activation can be regulated through direct interactions with binding partners[24]. Consequently, it is possible that ROBO1 binds to and directly inhibits the cleavage and activation of NOTCH4. To address this possibility, co-immunoprecipitation experiments were performed using MBA-MD-231 cells lysates, which express detectable levels of all four Notch receptors (NOTCH1-4). Endogenous ROBO1 co-immunoprecipitated with NOTCH4, but not NOTCH, NOTCH2 or NOTCH3 (FIG. 3H and data not shown). Next, the expression and subcellular localization of the NOTCH4 intracellular domain (N4-ICD) and HES1 was examined in control (Scr) and Robo1 (siR1) knockdown HC11 cells. Expression of Robo1 was inhibited in HC11 cells that were then primed for differentiation as described above. Robo1 knockdown cells displayed significantly higher expression of nuclear NOTCH4 intracellular domain (N4-ICD) and HES1, relative to control cells (Scr). This effect was not observed in control Robo1 knockdown cells engineered to overexpress Robo1 (siR1+o/e) or cells treated with the γ-secretase inhibitor GSI (siR1+GSI) (FIGS. 3I-3K).

Additional work addressed how the formation of the ROBO1/NOTCH4 complex is regulated over the time course of HC11 differentiation. An expression analysis was performed during the stages of HC11 differentiation (confluence, primed, milk dome formation)[19,20]. Analysis of ROBO1, pSTAT5 and the intracellular domain of NOTCH4 by Western blot over this time course revealed higher levels of ROBO1 (R1) and pSTAT5 during the milk dome formation stage, compared to other stages. In contrast, the NOTCH4 intracellular domain (N4-ICD) was expressed at lower levels during the milk dome formation stage (FIG. 3L). This finding is consistent with previous studies showing that NOTCH4 signaling is attenuated during alveologenesis[7-9]. Co-immunoprecipitation with anti-ROBO1 was used to pull down NOTCH4 in early (+EGF) and late (−EGF) stage, primed and differentiated (Dif) HC11 cells both in the absence and presence of SLIT2 and SLIT3 (FIG. 3M). ROBO1/NOTCH4 complex formation does not appear to be influenced by SLIT2/SLIT3 treatment in differentiated (Dif) HC11 cells. However, less ROBO1/NOTCH4 complex formation was observed in the presence of SLIT2 and SLIT3 in late stage primed cells (−EGF) relative to untreated cells. The ROBO1/NOTCH4 complex was not detected in early primed cells (+EGF), nor was it detected in control IgG immunoprecipitates. Taken together, these data suggest that ROBO1 directly binds and inhibits NOTCH4 cleavage and signaling during alveologenesis, impeding mammary epithelial cell differentiation into milk-producing cells.

Figure 2:
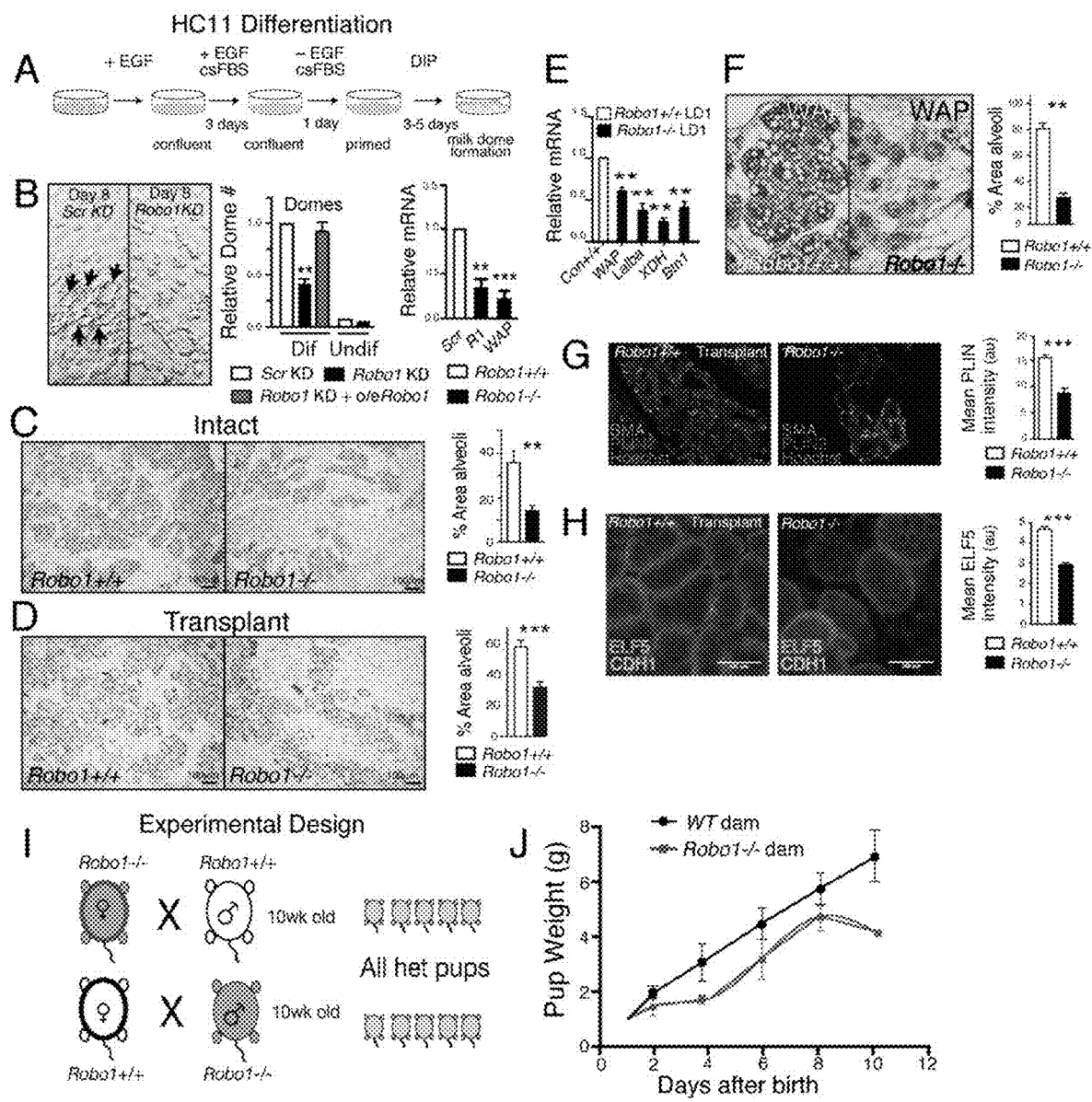
FIG. 2: ROBO1 enhances alveologenesis. (A) Cartoon representation of HC11 differentiation protocol. (B) Decreased dome formation in Robo1, compared to Scr, knockdown (KD) (arrows), HC11 cells, 8 days after differentiation (Dif) in dexamethasone (1 μg/ml), insulin (5 μg/ml) & prolactin (Prl, 5 μg/ml) (DIP media)[14]. Dome formation is rescued by Robo1 overexpression (o/e). Negligible dome formation under non-differentiation conditions (Undif). RT-qPCR, normalized to Scr control, shows reduced Robo1 & WAP after Robo1 knockdown (n=3). (C, D) Representative H&E-stained sections of PD18 Robo1 WT and KO intact mammary glands (C) and contralaterally transplanted outgrowths (D) with graphs showing decreased alveolar area (10 images, n=3). (E) RT-qPCR, relative to Robo1+/+, show decreased milk gene expression in LD1 Robo1−/− mammary glands (n=3). (F) Representative immunohistochemistry and graph of PD18 Robo1+/+, Robo1−/− mammary glands immunostained for WAP (n=10 images, n=1). (G) Representative immunohistochemistry for PLIN2 and SMA in pregnant day 18 contralaterally transplanted Robo1 WT/KO outgrowths with graphs showing decreased PLIN2 intensity in KO (10 images, n=3). (H) CUBIC method ELF5 and CDH1 immunohistochemistry on contralaterally transplanted pregnant day 18 Robo1 WT/KO outgrowths with graphs showing decreased ELF5 intensity (10 images, n=1). (1) Cartoon representation of assay to measure milk production by monitoring pup weight. (J) Current data showing reduced pup weight gain in pups nursed by a Robo1−/− dam (n=2). (SEM, $p<0.01$, *$p<0.001$).
Figure 4:
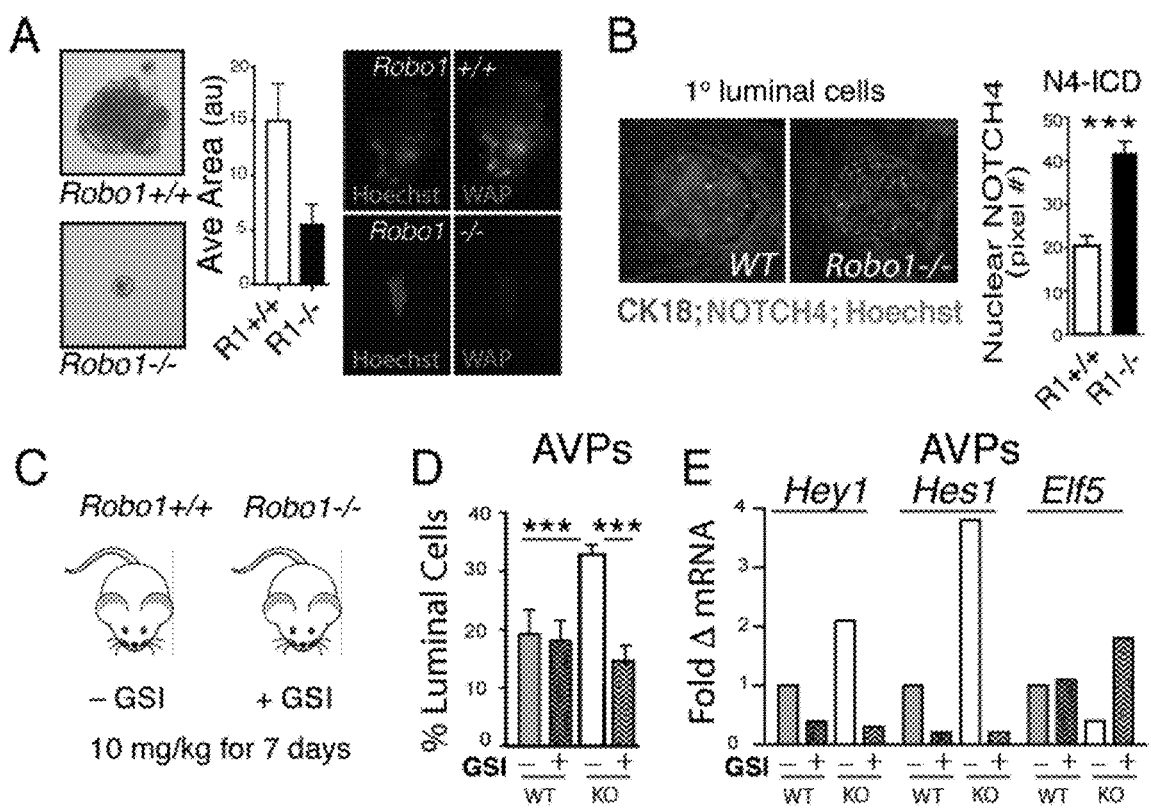
FIG. 4: FACS-purified Robo1−/− AVP colonies are smaller & express little/no WAP: (A) Robo1−/− FACS-purified alveolar progenitor cells (AVPs) cultured 5 days in Matrigel with Rho kinase inhibitor Y-27632 (10 μM, Tocris), Nrg1 (100 ng/ml, R&D), R-spondin 1 (600 ng/ml, R&D), prolactin (5 μg/ml, NHPP) are smaller than Robo1+/+ AVPs and express little to no WAP (n=2). (B) Increased levels of NOTCH4 ICD (N4-ICD) in nuclei of Robo1−/−, compared to Robo1+/+, primary (1°) luminal epithelial cells. (n=2). (C) Cartoon representation of assay to test Notch inhibition by treating Robo1+/+ and Robo1−/− mice with gamma-secretase (GSI) inhibitor. (D) The number of FACS-purified AVPs collected from Robo1+/+ and Robo1−/− mice treated with vehicle or GSI. (n=3). (E) RT-qPCR on FACs purified AVPs shows decreased Hey1, Hes1 expression in Robo1+/+ alveolar progenitor cells (AVPs), indicating that the GSI inhibited Notch signaling. There is also increased Hey1, Hes1 and decreased Elf5 expression in Robo1−/−, compared to Robo1+/+, cells, an effect that is rescued by GSI treatment (n=1). (SEM, ***$p<0.001$).

ROBO1 Inhibits Notch Signaling in Primary Cells and Mammals:

Because loss of Robo1 enhances NOTCH4 signaling and inhibits the differentiation of HC11 cells, this process was further evaluated in primary cells and animals. Alveolar progenitor cells were FACS-purified, plated at single cell density in Matrigel, and then allowed to grow in media supplemented with neuregulin (100 ng/ml) and R-spondin (42.5 ng/ml) for 5 days. The cells were then switched to a DIP media and allowed to differentiate for an additional 5 days 2. Colonies grown from Robo1−/− alveolar progenitor cells were observed to be smaller than colonies grown from WT alveolar progenitor cells and the Robo1−/− colonies did not produce WAP (FIG. 4A). Immunostaining was performed on cultured WT and Robo1−/− primary luminal cells. Significantly higher levels of NOTCH4 intracellular domain (N4-ICD) were detected in the nuclei of Robo1−/− primary cells relative to WT cells (FIG. 4B). These studies show that Robo1−/− alveolar progenitor cells (AVPs) contain high levels of the NOTCH4 intracellular domain in the nucleus and do not generate milk-producing organoids like their WT counterparts. This finding is consistent with the impaired alveologenesis observed in the Robo1−/− mammary glands (FIG. 2).

In further work, Notch signaling was inhibited to attempt to reverse the Robo1−/− phenotype. A γ-inhibitor that has been previously employed successfully in vivo to inhibit Notch in several different organs[26-28], including the mammary gland[29], was selected. Mature virgin animals were treated for seven days with 10 mg/kg of the GSI or vehicle control[29] (FIG. 4C). After the treatment, mammary glands were harvested and analyzed by FACS and qPCR. It was observed that Robo1−/− mammary glands contain a higher number of alveolar progenitor cells relative to WT controls (FIG. 4D). Treatment of the Robo1−/− animals with the gamma secretase inhibitor resulted in these animals having the same number of alveolar progenitor cells as WT animals (FIG. 4D). GSI treatment had no effect on the number of alveolar progenitor cells in WT animals (FIG. 4D).

Examination of the expression of Notch effector genes (Hey1 and Hes1) revealed less expression of Notch effectors in GSI-treated, compared to vehicle-treated, animals (FIG. 4E). Although GSI inhibitors do not specifically target Notch receptors, this result indicates the drug works in the mammary gland to reduce Notch signaling. Robo1−/− alveolar progenitor cells (AVPs) expressed higher levels of Hey1 and Hes1 with vehicle treatment compared to AVPs from vehicle-treated WT animals (FIG. 4E). This result is similar to those seen with primary alveolar progenitor cells and HC11 cells (FIG. 3B, C). Vehicle-treated Robo1−/− alveolar progenitor cells (AVPs) expressed lower levels of Elf5 than AVPs from vehicle-treated WT animals (FIG. 4E). This is consistent with the observation of lower levels of ELF5 expression in Robo1−/− compared to Robo1+/+ mammary glands (FIG. 2H), and lower Elf5 in Robo1 knockdown compared to control (Scr) HC11 cells (FIG. 3C). Further observations showed that treating Robo1−/− animals with GSI reversed the altered AVP gene expression relative to vehicle-treated Robo1−/− animals—Hey1 and Hes1 expression was lower in AVPs from GSI-treated Robo1−/− animals relative to vehicle-treated Robo1−/− animals, while Elf5 expression was higher in AVPs from GSI-treated Robo1−/− animals relative to vehicle-treated Robo1−/− animals (FIG. 4E). Taken together this work indicates that ROBO1 restricts NOTCH4 signaling. In the absence of Robo1, NOTCH4 is activated—an effect that is reversed by either pharmacological inhibition of Notch signaling (FIGS. 4E, 3E, 3F, 3I-K) or knockdown of Notch4 gene expression (FIGS. 3F,G).

Figure 5:
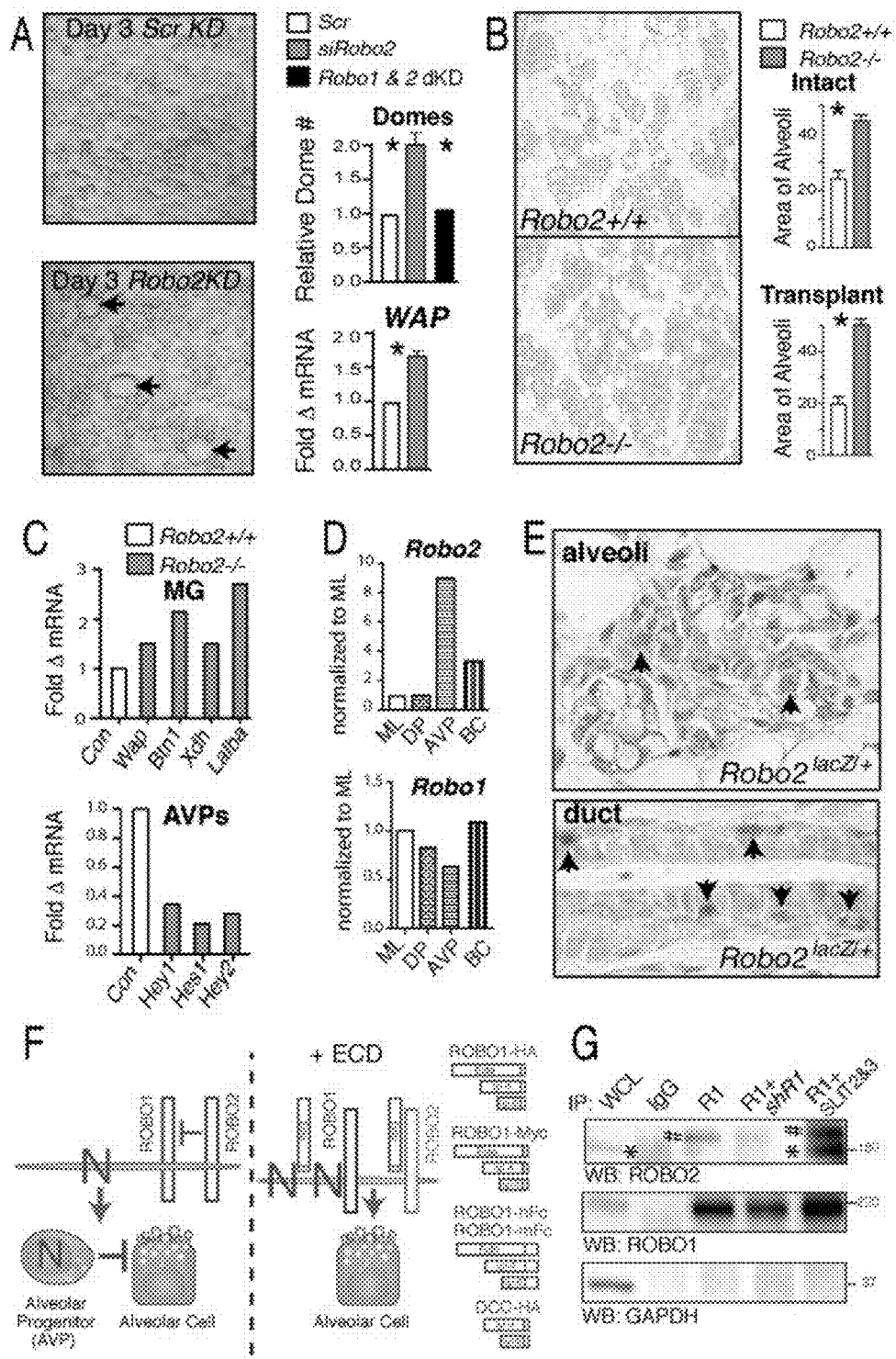
FIG. 5: Robo2 inhibits alveologenesis. (A) Increased dome formation and WAP expression with Robo2 knockdown after three days differentiation (arrows), a phenotype rescued by Robo1 & 2 double knockdown (dKD) (B) Representative H&E-stained sections of DP16 Robo2 WT and KO mammary glands. Quantitation of alveoli in intact Robo2−/− mammary glands and transplanted Robo2−/− outgrowths show increased alveolar area in Robo2−/−, compared to Robo2+/+, tissue (n=10 images, n=1). (C) RT-qPCR of milk (top) and Notch effector (bottom) genes in Robo2−/− mammary glands (MG), normalized to Robo2+/+ control. (D) β-galactosidase (LacZ) staining shows Robo2 in a subset of luminal cells in DP16 alveoli (top) and in a subset of basally located cells in ducts from a retired breeder (bottom). (E) RT-qPCR for Robo2 and Robo1 in FACS purified subpopulations of mammary epithelial cells. Robo1 expression is in all populations, whereas Robo2 expression is restricted to alveolar progenitor cells (AVPs) and basal (BC) cells (F) Cartoon model showing ROBO2 inhibiting ROBO1, allowing NOTCH4 (N) activation that reduces alveolar differentiation (left). ROBO1 extracellular domains (ECDs) bind ROBO2, releasing ROBO1, which then inhibits NOTCH4, and/or ECDs bind and directly inhibit NOTCH4; both scenarios promote differentiation. Panels of ECDs representing the different constructs generated for the project (right). (G) Endogenous levels of ROBO2 co-immunoprecipitate with ROBO1 in HEK293 lysates and co-immunoprecipitation is potentiated by SLIT2/SLIT3 treatment, * is ROBO2, # is glycosylated ROBO2 (n=1). (SEM, n=3, *$p<0.05$).

ROBO2 Inhibits Alveologenesis:

Inhibition of Robo2 in animals and cells resulted in the opposite phenotype as that resulting from the inhibition of Robo1 expression. In HC11 cells, the inhibition of Robo2 expression (Robo2 KD) led to faster differentiation, higher WAP expression and greater milk dome number as compared to a control cells (Scr). Inhibition of Robo1 and Robo2 in the same cells resulted in a milk dome number indistinguishable from the negative control (FIG. 5A).

Alveologenesis was evaluated in both intact Robo2−/− mammary glands and contralaterally transplanted Robo2−/− outgrowths. Significantly faster alveologenesis was observed in both intact Robo2−/− mammary glands and in Robo2−/− transplants relative to Robo2+/+ control mammary glands as measured by alveolar area (FIG. 5B). The expression of milk genes in intact, virgin Robo2−/− mammary glands (MG) was higher than Robo2+/+ controls, whereas the expression of Notch effector genes (Hey1, Hes1 and Hey2) in FACS-purified alveolar progenitor cells (AVPs) from Robo2−/− intact mammary glands was lower than Robo2+/+ controls (FIG. 5C).

Robo2 expression was assessed by RT-qPCR in FACS-purified subpopulations from virgin mammary epithelial cells. Unlike Robo1, which is expressed in all subpopulations, Robo2 expression is more restricted—it is expressed at a high level in alveolar progenitor cells (AVPs) and at a lower level in basal cells (BCs) (FIG. 5D). Expression in ductal progenitor cells (DPs) could not be differentiated from expression in mature luminal cells (MLs); expression in MLs was used for normalization. Robo2 expression in tissue was examined by β-galactosidase (lacZ) staining on mammary gland sections from Robo2$^{lacZ/+}$ glands. Robo2 expression was observed in a subpopulation of luminal cells in alveoli at pregnant day 18 (FIG. 5E, top), and in a subpopulation of basally located cells along ducts of a retired breeder animal (FIG. 5E, bottom).

One interpretation of these phenotypic and expression data is that ROBO2 inhibits ROBO1 in alveolar progenitor cells. During differentiation, ROBO2 is downregulated, releasing ROBO1, which then inhibits NOTCH4, creating a disinhibitory circuit (ROBO2-|ROBO1-|NOTCH4) (FIG. 5F left). In other words, inhibition of Robo2 expression allows ROBO1 to enhance alveolar differentiation. Inhibition of Robo1 expression allows NOTCH4 to inhibit alveolar differentiation.

The Interaction Between ROBO1 and ROBO2 is Potentiated by SLIT:

The interactions between SLIT and ROBO proteins are evolutionarily conserved, as evidenced by studies showing that human SLIT2 binds *Drosophila* Robo1 with similar affinity as its mammalian receptor, and, vice versa, that *Drosophila* Slit binds rat ROBO1 and ROBO2[30]. Biochemical studies show the interaction between this receptor/ligand pair involves the highly conserved second LRR domain of Slit and the conserved Ig1 domain of Robo, while the Ig2-Ig5 domains and all FN3 domains of ROBO1 appear dispensable for binding[31-34]. In addition, studies have shown that ROBO1 and ROBO2 can bind to each other, both in cis[32,35,36] and in trans[37]. This interaction also depends on the Ig domains. Recent crystallography experiments show that unliganded ROBOs form a compact homotypic dimer that opens in response to SLITs, allowing the formation of a dimer-of-dimers between ROBOs[38].

The disclosed model indicates that ROBO2 inhibits ROBO1. To investigate whether this inhibition is due to a direct interaction, a co-immunoprecipitation experiment was performed on endogenous proteins in HEK cells using a ROBO1 antibody. A band that is bound by a ROBO2 antibody, which appears to be a glycosylated form, co-immunoprecipitated, with ROBO1. This band is lower in intensity when the immunoprecipitation is performed using cells in which Robo1 expression is inhibited (FIG. 5G). When the cells are treated with SLIT2 and SLIT3 (1 μg, each) for four hours prior to lysate preparation and co-immunoprecipitation using an anti-ROBO1 antibody, two intensely staining bands are observed for ROBO2. This suggests that SLIT2 and SLIT3 facilitate more efficient interaction between ROBO1 and ROBO2 (FIG. 5G).

ROBO1 Receptor Extracellular Domain Fragments Bind ROBO2:

The experiments disclosed herein suggest that ROBO1 and NOTCH4 form a complex that inhibits NOTCH4 activation, suggesting a direct interaction between the two proteins. Previous studies have shown that soluble extracellular domain fragments of many transmembrane receptors act to block both homophilic and heterophilic interactions between transmembrane receptors as well as interactions between transmembrane receptors and their ligands[39]. It can be hypothesized that soluble ROBO1 extracellular domains (ECDs) can similarly interfere with the interaction between ROBO1 and ROBO2. Constructs comprising ROBO1 ECDs can compete for ROBO2 binding with endogenous ROBO1, thereby allowing the endogenous ROBO1 to bind NOTCH4 and inhibit NOTCH4 activation, thereby enhancing alveolar differentiation and promoting milk production (FIG. 5F right). Soluble ROBO1 ECDs may also directly bind and inhibit NOTCH4 activation in a non-mutually exclusive manner, which would also have the result of enhancing differentiation of alveoli (FIG. 5F right). Thus, ROBO1 ECDs may both directly and indirectly inhibit NOTCH4 activation.

Figure 6:
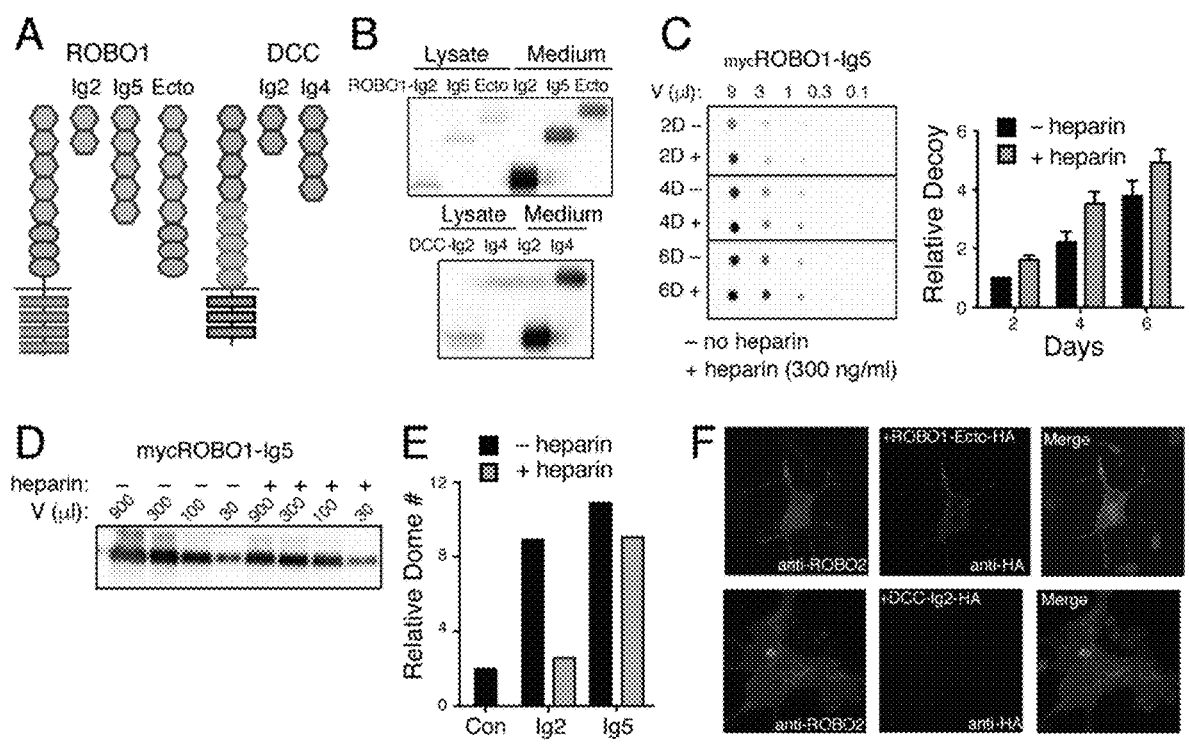
FIG. 6: ROBO1 extracellular domains. (A) Cartoon showing domain structure of the ROBO1 extracellular domain (ECD) panel (B) Western blot of ROBO1 ECDs and control DCC ECDs in lysates and conditioned media of HEK cells overexpressing plasmid constructs. (C) Dot blot assay of media (left) and quantification (right) of ROBO1-Ig5 secretion from HEK cells overexpressing Robo-Ig5 in the absence and presence of heparin (300 ng/ml). Heparin modestly increases secretion (n=1). (D) Western blot of lysate titration in the absence and presence of heparin (300 ng/ml) shows no protein degradation. (E) HC11 dome formation assay shows that the function of ECDs ROBO1-Ig2 and ROBO1-Ig5 is diminished in the presence of heparin (n=1). (F) ECD binding assay using ROBO1-Ecto and cells overexpressing ROBO2 (top, green) and cells overexpressing DCC (bottom, green). ROBO1-Ecto-HA (red) binds to ROBO2, but not to DCC.

Three recombinant ROBO1 ECD constructs were constructed: one comprising two immunoglobulin (Ig) domains (ROBO1-Ig2), another comprising all five Ig domains (ROBO1-Ig5), and another comprising the entire extracellular domain (ROBO1-Ecto) (FIG. 6A). In other constructs, HA (hemagglutinin), Myc, and human and mouse immunoglobulin Fc were fused to the Robo1 ECDs (FIG. 6A, 5F right). Extracellular domains of Deleted in Colorectal Cancer (DCC), a structurally similar Ig superfamily member to ROBO1, comprising either two Ig (DCC-Ig2) or four Ig (DCC-Ig4) domains and tagged with HA were constructed for use as negative controls (FIG. 6A, 5F right). Expression secretion of the constructs was confirmed by overexpressing the constructs in HEK293 cells and performing Western blots on cell lysates and media (FIG. 6B). Previous studies showed that incubating cells with the highly sulfated variant of heparan sulfate, heparin, enhances secretion of some extracellular proteins[40]. Robo1-Ig5 as used herein was expressed in HEK-293 cells in the absence and presence of heparin (300 ng/ml). Media were collected from these ROBO1-Ig5 overexpressing cells on days two, four and six following plasmid transfection. Dot blot dilution assays of the collected media were performed to evaluate the relative secretion of this soluble ROBO1 ECD (FIG. 6C). Soluble ROBO1-Ig5 secretion increased over this time course, with heparin treatment resulting in a trend of greater secretion (FIG. 6C). Media samples from these ROBO1-Ig5 transfected cells were also TCA-precipitated and analyzed by Western blot that showed intact ROBO1-Ig5 protein after 6 days in media both in the absence and presence of heparin (FIG. 6D).

Soluble ROBO1 ECD fragments ROBO1-Ig2 and ROBO1-Ig5 generated in the presence of heparin were used in a dome assay. The results indicated that soluble ROBO1 ECD fragments generated in the presence of heparin formed fewer domes than the same fragments generated in the absence of heparin (FIG. 6E). Because treatment with heparin had only a modest positive effect on ROBO1 ECD production and a deleterious effect on their function (FIG. 6C, E), the use of heparin to generate soluble ROBO1 ECD fragments was not pursued. The ability of a ROBO1 ECD fragment to bind ROBO2 receptors was tested by overexpressing Robo2 in Cos7 cells, treating cells with sodium azide to prevent protein internalization and then incubating cells with ROBO1-Ecto-HA 1H prior to fixation and immunostaining. Results showed that the ROBO1-Ecto-HA binds to ROBO2, but DCC-Ig2-HA does not bind to ROBO2 (FIG. 6G).

Figure 7:
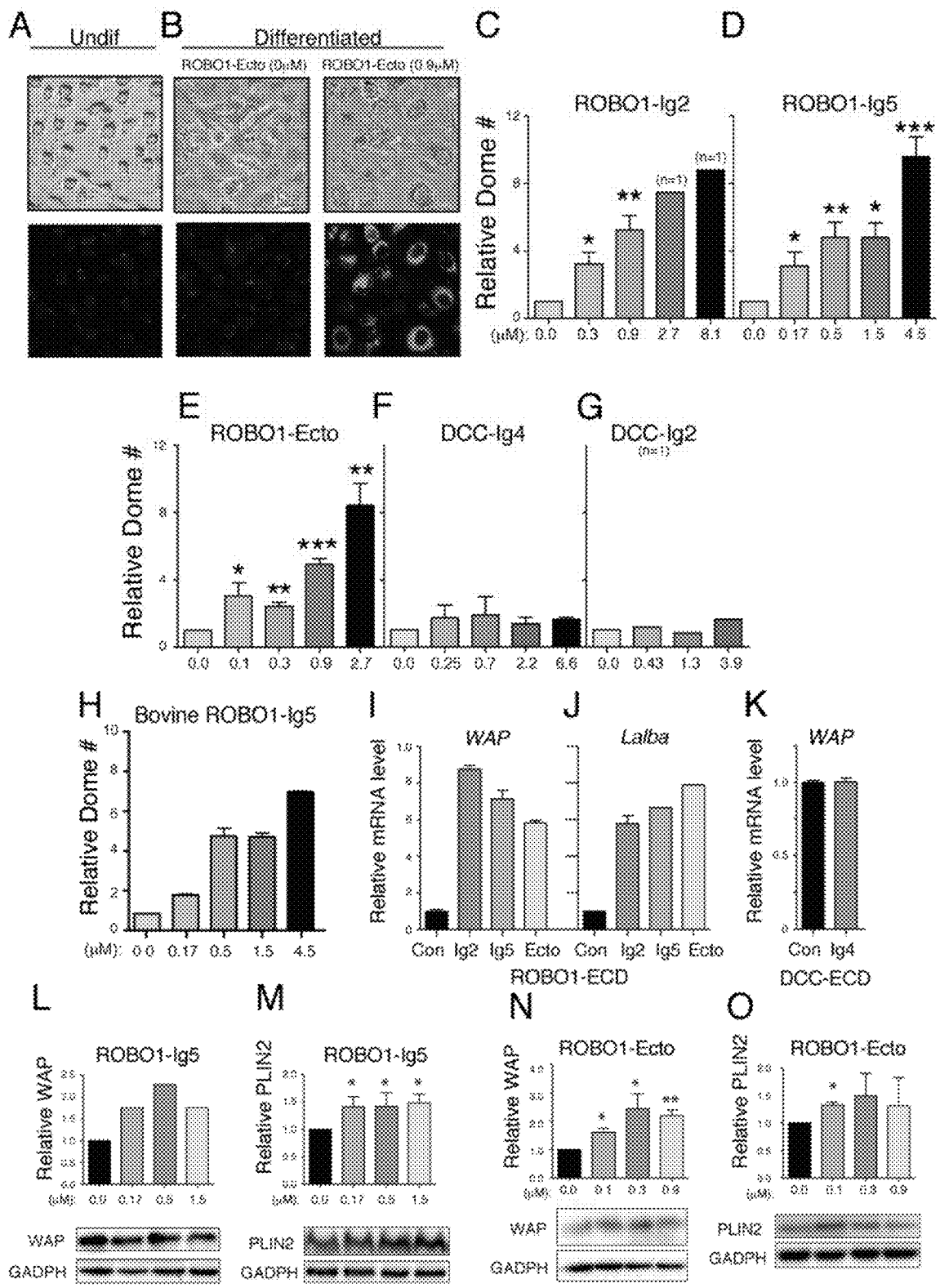
FIG. 7: ROBO1 extracellular domains enhance differentiation. (A) Representative phase contrast (top) and Bodipy 493/503 staining (bottom) of HC11 cells in the absence and presence of ROBO1-Ecto treatment. (C-G) Titration assay measuring the effect of ROBO1 ECDs on HC11 differentiation show that ROBO1-ECDs, but not DCC-ECDs, increase HC11 dome formation with increasing ECD concentration (n=3 except where indicated). (H) Titration assay measuring the effect of bovine ROBO1-Ig5 on HC11 differentiation shows increasing dome formation with increasing concentration (n=2). (I-K) RT-qPCR shows increased WAP (n=1) and Lalba (n=2) gene expression after ROBO1-ECD treatment, relative to control treatment. There is no change in WAP (n=1) expression after DCC-Ig4 (0.7 μM) treatment. (L-O) ROBO1 ECD titration shows increased WAP (n=1) and PLIN2 (n=4) expression with ROBO1-Ig5 (L, M) and increased WAP (n=3) and PLIN2 (n=2) with ROBO1-Ecto (N,O) treatment. (SEM, *p<0.05, p<0.01, *p<0.001)

ROBO1 Extracellular Domain Fragments Enhance HC11 Cell Differentiation:

To determine whether the ROBO1 ECD fragments influence NOTCH4 signaling, HC11 assays were performed to monitor dome formation using both phase contrast microscopy (FIG. 7A, B, top), and fluorescent microscopy using hydrophobic Bodipy493/503 that binds neutral lipids (FIG. 7A, B, bottom). Undifferentiated (Undif) cells are distinct with interconnecting processes visible in phase contrast and little/no Bodipy staining (FIG. 7A). Upon differentiation and prolactin treatment, small lipid droplets accumulate that appear as dark-rimmed circles in phase contrast (FIG. 7B, top) and as punctate green circles by Bodipy staining (FIG. 7B, bottom). Bodipy493/503 staining revealed that treatment with ROBO1-Ecto resulted in a higher number of cells completely surrounded by lipid droplets (FIG. 7B).

Dome number formation in response to a titration of ROBO1 ECD fragments was quantified. Higher concentrations of ROBO1-Ig2, ROBO1-Ig5, and ROBO-1-Ecto significantly correlated with higher rates of dome formation. This result was not observed in response to treatment with either DCC-Ig2 or DCC-Ig4 control ECD fragments (FIG. 7C-G). A bovine ROBO1-Ig5 construct was also tested in this assay and, as with the rat constructs, more domes were formed in response to treatment with higher concentrations of ROBO1-Ecto ECD (FIG. 7H). Together these studies show that ROBO1-ECDs promote dome formation in HC11 cells.

To determine whether the promotion of dome formation also results in higher milk production, HC11 cells were differentiated in the presence or absence of ROBO1-ECD fragments that were added to cells simultaneously with DIP media. Cells were harvested and the expression of WAP and Lalba assessed by RT-qPCR. Treatment with different ROBO1-ECDs resulted in 6-9 fold greater expression relative to no treatment controls (FIG. 7I, J). WAP expression levels were not increased in cells treated with DCC-Ig4 (FIG. 7K). Next, Western blot analysis of WAP and PLIN2 was performed on cells treated with ROBO1-Ig5 and ROBO1-Ecto. An approximately two-fold increase in WAP and PLIN2 protein expression was observed in cells treated with ROBO-1 ECDs (FIG. 7L-O).

Figure 8:
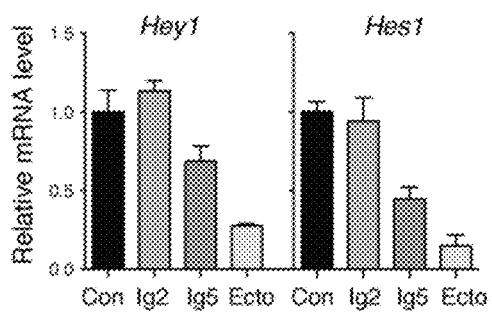
FIG. 8: ROBO1 extracellular domains inhibit Notch activation. (A) RT-qPCR shows decreased Hey1 and Hes1 expression in HC11 cells treated with ROBO1-Ig5 and ROBO1-Ecto, but not ROBO1-Ig2 (n=1). (B) Fractionated (cytoplasmic/nuclear) primed HC11 cells analyzed by Western blot show decreased HES1 and NOTCH4-ICD (N4-ICD) with ROBO1-Ig5 treatment in nuclear fractions, with NOTCH4-ICD (N4-ICD) also reduced in the cytoplasmic fraction. (C) HC11 differentiation assay shows increased dome formation with ROBO1-Ig5 treatment under Scramble KD (Scr) conditions. Knockdown of Robo1 (shROBO1) decreases dome formation in untreated cells (Control), an effect that is rescued by ROBO1-Ig5 treatment. Knockdown of Notch4 (shNotch4) increases dome formation in the untreated cells (Control), an increase that is unaffected by ROBO1-Ig5 treatment (n=2).
Figure 8:
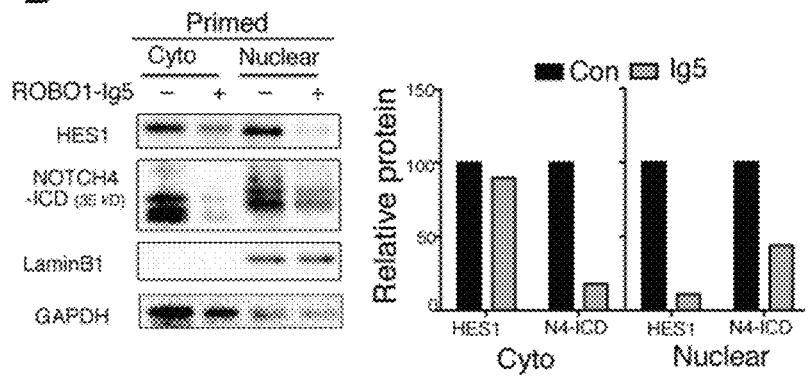
Figure 8:
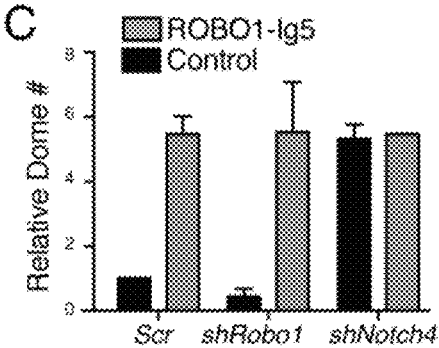

ROBO1 Extracellular Domain Fragments Inhibit Notch Signaling:

To examine the effects of ROBO1-ECD fragments on Notch signaling, HC11 cells were treated with ROBO1-ECD fragments and Notch effector expression assessed. ROBO1-Ig5 and ROBO1-Ecto treatment resulted in lower expression of Hey1 and Hes1 (FIG. 8A), although this effect was not observed in cells treated with ROBO1-Ig2 (FIG. 8A). In addition, HC11 cells were treated with ROBO-Ig5 during differentiation. These cells were then fractionated and a Western blot performed to detect HES1 and NOTCH4-ICD (FIG. 8B). Treatment with ROBO1-Ig5 resulted in lower levels of both HES1 and NOTCH4-ICD (N4-ICD) protein in the nuclear fraction relative to control treatment; NOTCH4-ICD was also lower in the cytoplasmic fraction with ROBO1-Ig5 treatment. Taken together, these results suggest that ROBO1-ECDs inhibit Notch signaling.

Disclosed herein is a model whereby soluble ROBO1 ECD fragments bind ROBO2, preventing it from binding endogenous transmembrane ROBO1 and thereby promoting formation of ROBO1/NOTCH complexes that interfere with Notch signaling (FIG. 5F right). However, it is possible that ROBO1-ECD fragments also directly bind and inhibit NOTCH4. Therefore, to test if ROBO1-ECD fragments inhibit Notch in the absence of ROBO1, Robo1 expression was inhibited in HC11 cells. The cells that lacked Robo1 expression were then treated with ROBO1-ECD fragments and their ability to form domes assessed. As previously observed (FIGS. 7C-E, H), treatment with ROBO1-ECD fragments increased dome formation in control cells (Scr) (FIG. 8C). Inhibition of Robo1 expression (shRobo1) also inhibited dome formation in control cells (FIG. 8C), as previously observed (FIGS. 1B, 3E). However, treatment of cells, in which Robo1 expression was inhibited (shRobo1), with ROBO1-Ig5 resulted in dome formation at the same level as that of control cells (Scr) treated with ROBO1-ECD fragments (FIG. 8C). Inhibiting expression of Notch4 (shNotch4) in the absence of ROBO1-Ig5 fragment resulted in greater dome formation compared to control cells (Scr) (FIG. 8C), as previously observed (FIG. 3G). Treating these cells (shNotch4) with ROBO1-Ig5 led to the same level of dome formation as untreated Notch4 knockdown cells (shNotch4) (FIG. 8C). This suggests that ROBO1-Ig5 treatment does not further increase HC11 dome formation in the absence of NOTCH4. Taken together, the results suggest that NOTCH4 is a direct target of ROBO1-Ig5.

Figure 9:
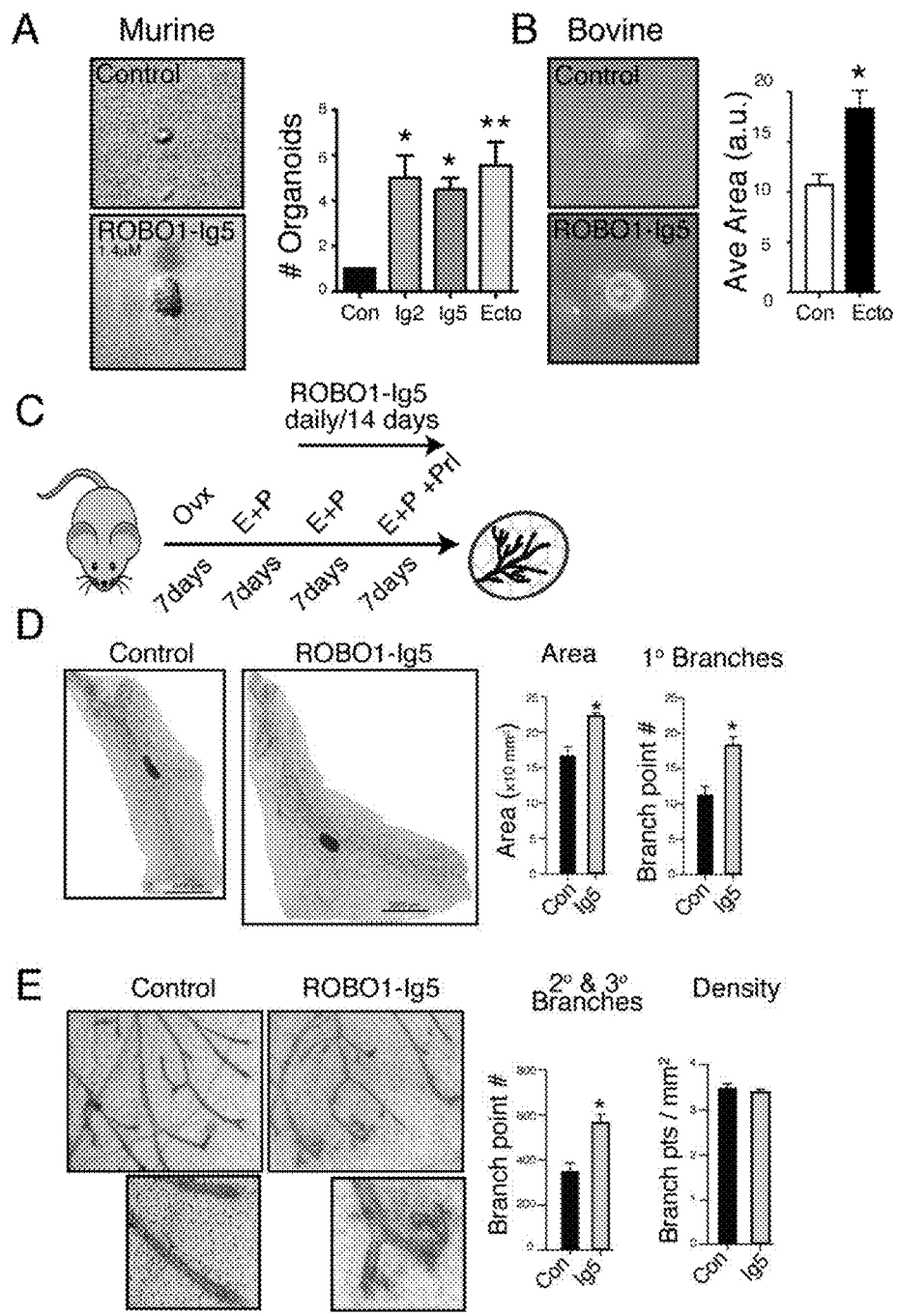
FIG. 9: Subcutaneous injection of a ROBO1 extracellular domain fragment increases branching: (A) WT primary murine alveolar progenitor cells (AVPs) are FACS-purified and grown in Matrigel in the absence (Control) and presence of ROBO1 ECDs. All ROBO1 ECD fragments increased the number of organoids, with representative picture showing AVPs grown in the presence of ROBO1-Ig5 (n=3). (B) WT primary bovine alveolar progenitor cells (AVPs) are FACS-purified and grown in Matrigel in the absence (Control) and presence of ROBO1-Ig5, which increased the size of the organoids (n=2). (C) Cartoon representation of ROBO1-Ig5 injection protocol. Animals are ovariectomized (Ovx), then treated with hormones and injected with either PBS or ROBO1-Ig5 fragment. (D) Increased mammary gland size and number of primary (1°) branches in animals injected with ROBO1-Ig-5 (n=3). (E) Increased number of secondary/tertiary (2°, 3°) branches in mammary glands injected with ROBO1-Ig5, but no increase in branching density (n=3). (SEM, *p<0.05).

ROBO1 Extracellular Domain Fragments Enhance Organoid Formation and Mammary Gland Branching:

The influence of ROBO1 ECD fragments in vitro on primary alveolar progenitor cell growth and in vivo on branching morphogenesis was tested. FACS-purified murine and bovine alveolar progenitor cells (AVPs) were plated as single cells in Matrigel and grown for 10 days in the absence and presence of ROBO1-ECDs fragments (FIGS. 9A, B). Treatment with ROBO1-ECDs resulted in more murine organoids compared to untreated controls (FIG. 9A). Treatment with ROBO1-Ig5 resulted in larger bovine organoids compared to untreated controls (FIG. 9B). ROBO1-Ig5 fragments were also tested in vivo by subcutaneously injecting them (7.5 mammary gland/kg/day) into ovariectomized animals that were orally administered hormones in Nutella: estrogen (E, 1 µg/day), progesterone (P, 1 mg/day mammary gland/day) and prolactin (Prl, 0.2 mg/day mammary gland/day) (FIG. 9C). The mammary glands were harvested after 14 days of ROBO1-Ig5 fragment treatment, carmine stained and evaluated. ROBO1-Ig5 treatment resulted in a significantly greater area and a higher number of primary (1°) branches relative to untreated controls (FIG. 1D). More secondary (2°) and tertiary (3°) branching of the glands was also observed; however, because the size of the gland area was greater in glands greater branching, the overall branching density of the treated glands was not different from that of controls (FIG. 1E). Taken together, this study shows that in vivo ROBO1-Ig5 treatment resulted in mammary glands with significantly more branches. Other aspects can involve ROBO1-ECD constructs that are tagged with the murine-Fc sequence. This tag is recognized by an endogenous receptor that facilitates transport into tissues 4.

Figure 10:
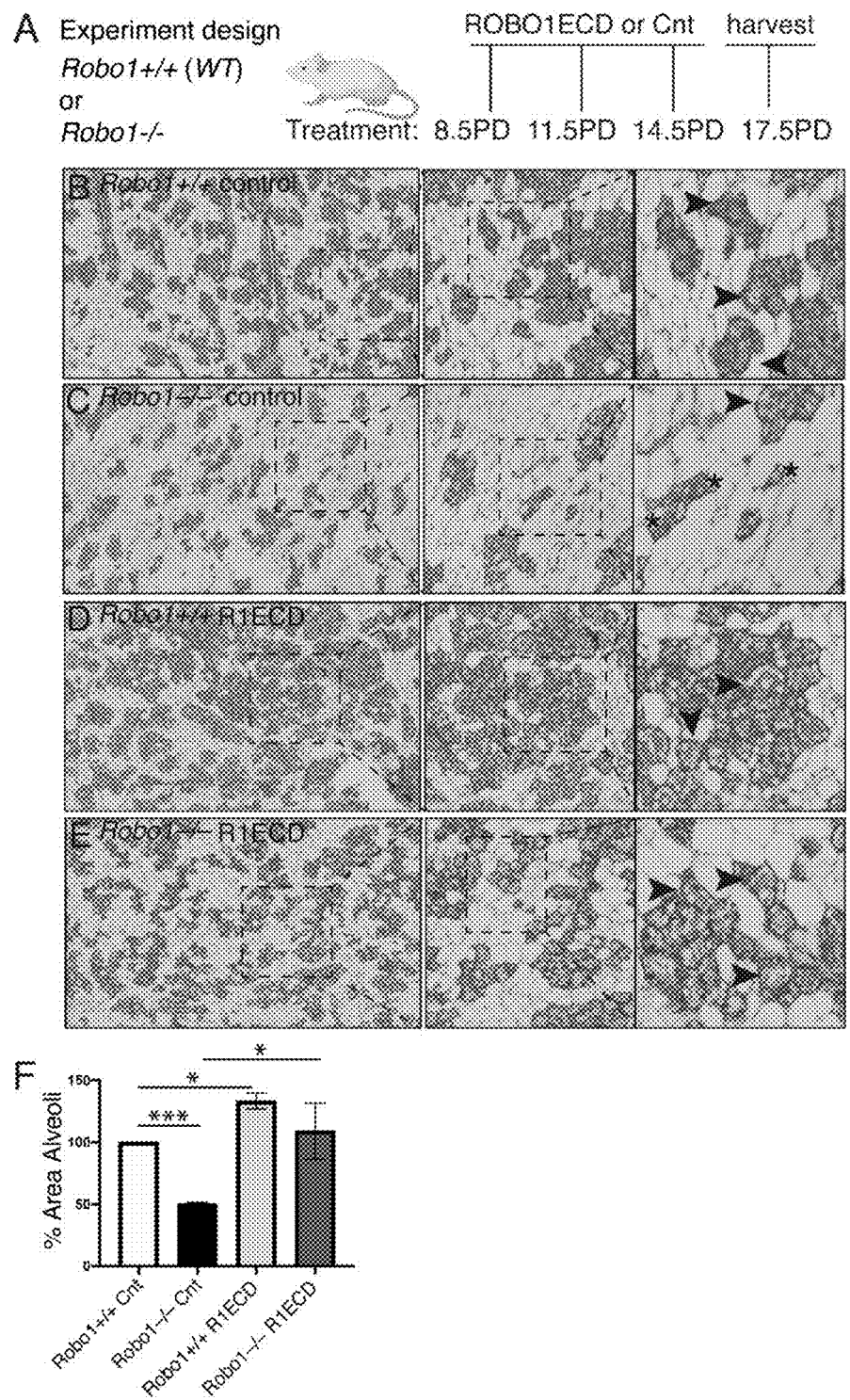
FIG. 10: ROBO1 Extracellular Domain Fragments Increase Lobulo-alveolar Mammary Development. (A) Cartoon representation of ROBO1 ECD-Fc fragment subcutaneous injection protocol. Robo1+/+(WT) or Robo1−/− animals are subcutaneously injected at pregnant day (PD) 8.5, 11.5 and 14.5 with either PBS or ROBO1 ECD-Fc. Mammary gland are harvested on PD 17.5. (B, C) Representative H&E staining of mock-injected, WT and Robo1−/− glands (controls) display the previously observed Robo1−/− phenotype of reduced lobulo-alveolar development (arrows) and smaller, dense alveoli (asterisks). (D, E) Increased lobulo-alveolar development and milk droplet production in WT (D) and Robo1−/− (E) glands subcutaneously injected with ROBO1 ECD-Fc fragment. (F) Quantification of the percentage (%) of alveoli shows a significant decrease in alveolar area in the mock injected Robo1−/− mammary gland tissue compared to control Robo1+/+ tissue, and significant increases in alveolar area with the injection of ROBO1 ECD-Fc (R1ECD) fragment into either Robo1+/+ or Robo1−/− animals. (SEM, *p<0.05, ***p<0.001).

ROBO1 Extracellular Domain Fragments Increase Lobulo-Alveolar Mammary Development and Milk Production:

The influence of ROBO1 ECD-Fc fragments in vivo on lobulo-alveolar development during pregnancy was investigated. ROBO1 ECD fragments (7.5 mg/kg) and mock-injected control were subcutaneously injected three times (pregnant day (PD) 8.5, PD 11.5 and PD 14.5) during pregnancy (FIG. 10A). The mammary glands were harvested at PD 17.5 and alveologenesis analyzed by serially sectioning, hematoxylin and eosin (H&E) staining and then quantifying the area occupied by alveoli in sections located at top, middle and bottom portions of the tissue. As previously observed, there was a significantly reduced alveolar area in the Robo1−/−, compared to WT, mock injected mammary glands, and a reduction in Robo1−/− alveolar size (FIGS. 10B, C, F arrows, asterisks). Injection of ROBO1 ECD-Fc fragments into both the WT and Robo1−/− animals resulted in a significant increase, compared to mock-injected control, in alveolar area and alveoli filled with milk droplets.

Figure 11:
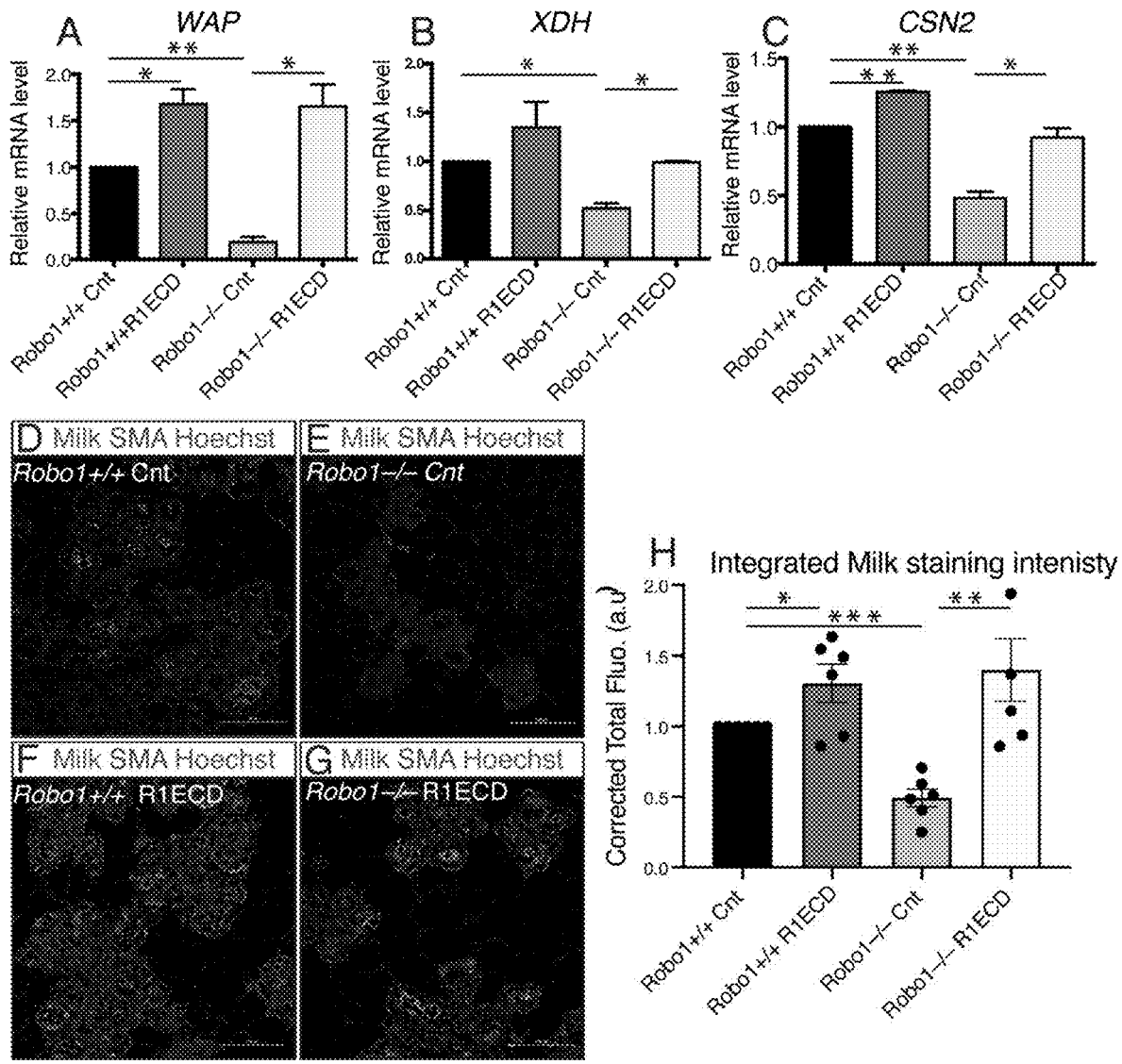
FIG. 11: ROBO1 Extracellular Domain Fragments Increase Milk Production. (A-C) RT-qPCR shows significantly reduced expression of WAP (A), XDH (B) and CSN2 (C) in mock-injected Robo1−/− compared to Robo1+/+ animals. There is significantly increased expression of WAP, CSN2 and a trending increase in XDH in Robo1+/+ animals injected with ROBO1 ECD-Fc (R1ECD). There is significantly increased expression of WAP, XDH and CSN2 in Robo1−/− animals injected with ROBO1 ECD-Fc (R1ECD). (D-H) Immunohistochemistry (D-G) and quantification (H) demonstrates a significant decrease in milk protein expression in the mock-injected Robo1−/− mammary gland tissue compared to control Robo1+/+ tissue and significant increases in milk protein expression with the injection of ROBO1 ECD-Fc (R1ECD) fragment into either Robo1+/+ or Robo1−/− animals. (SEM, *p<0.05, p<0.01, *p<0.001).

To further evaluate milk production, RT-qPCR on milk protein genes whey acidic protein (WAP), Xanthine Dehydrogenase (XDH) and beta-casein (CSN2) was performed. Compared to control treatment, there are significant increases in milk protein gene expression with ROBO1 ECD-Fc treatment (FIG. 11A-C). Milk expression was also evaluated at the protein level by immunohistochemistry on sectioned tissue using an antibody directed against milk (# YNRMTM, Accurate Chemical and Scientific Corp). Again, significant increases in milk were observed with the injection of ROBO1 ECD into either WT or Robo1−/− animals (FIG. 11D-H). Together these data show that subcutaneous injection of ROBO1 ECD fragment into pregnant animals increases lobulo-alveolar development, milk protein gene and milk production.

Figure 12:
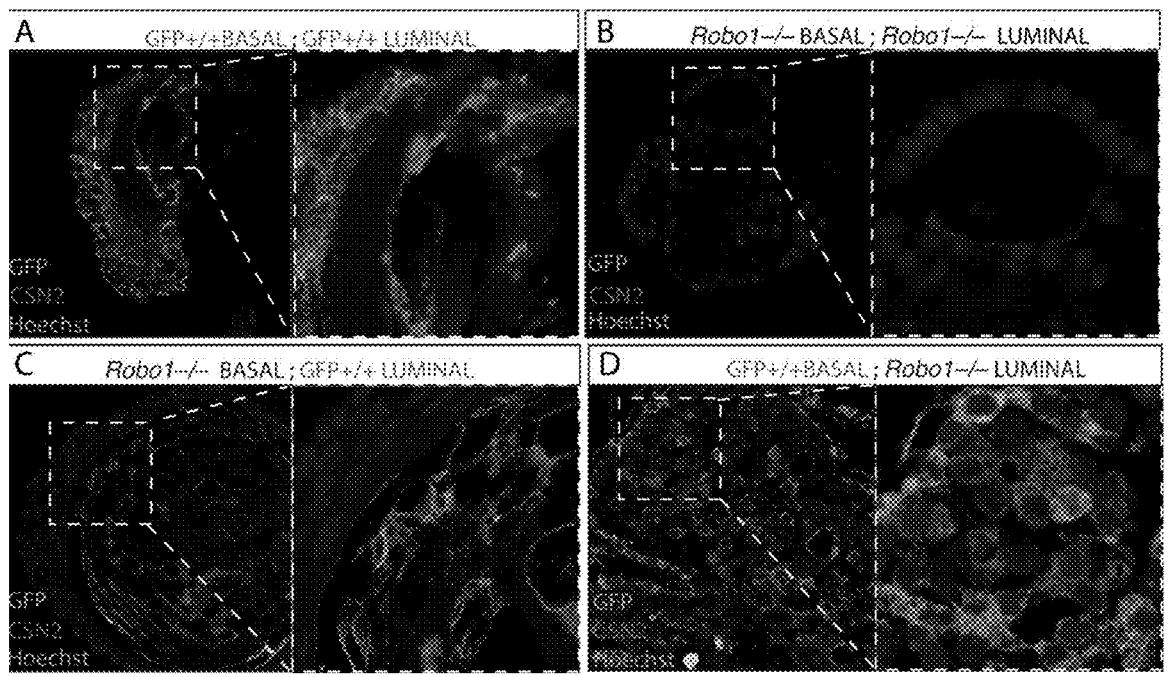
FIG. 12: ROBO1 is Required in Basal Cells of the Mammary Gland for Alveolar Differentiation and Milk Production. (A-D) Mosaic organoids were generated by reconstituting purified populations of luminal and basal cells. ACTb-EGFP mice were used for WT tissue (GFP+/+). (A) GFP+/+ basal and GFP+/+ luminal cells, reconstituted into a mammary organoid, generate CSN2 (β-casein) upon differentiation. (B) Robo1−/− basal and Robo1−/− luminal cells, reconstituted into a mammary organoid, generate little/no CSN2 upon differentiation. (C) Robo1−/− basal and GFP+/+ luminal cells, reconstituted into a mammary organoid, generate little/no CSN2 upon differentiation. (D) GFP+/+ basal and Robo1−/− luminal cells, reconstituted into a mammary organoid, generate CSN2 upon differentiation.

ROBO1 is Required in Basal Cells of the Mammary Gland for Alveolar Differentiation and Milk Production:

The mammary gland is a bi-layered tissue composed of outer basal cells (basal compartment) and inner luminal cells (luminal compartment) (FIG. 1A). ROBO1 expression was detected in both luminal and basal cells of the mammary gland (FIG. 1D-G). To determine in which cell type ROBO1 functions to enable the differentiation of alveolar progenitor cells into milk producing alveolar cells, organoids were generated that were mosaic in the expression of ROBO1 such that either cells comprising the basal or luminal compartment were composed of Robo1−/− cells (FIG. 12C, D). As a control, WT and Robo1−/− organoids were generated with WT and KO cells comprising both the basal and luminal compartments (WT/WT and KO/KO) (FIG. 12A, B). ACTb-EGFP mice were used for WT tissue (GFP+/+) to distinguish between WT and KO cells. Organoids were generated by differential trypsinization to separate the two populations followed by mixing of the separated basal and luminal subpopulations to generate organoids (WT/WT, KO/KO, WT/KO, KO/WT) that were then cultured in Matrigel followed by differentiation for 5 days. WT/WT organoids, comprising both GFP+/+ basal and GFP+/+ luminal cells, formed large, bilayered organoids that upon differentiation produced milk that filled the lumen (FIG. 12A). In contrast, KO/KO organoids, comprising both Robo1−/− basal and Robo1−/− luminal cells, generated smaller bilayered structures that upon differentiation produced little or no milk (FIG. 12B). When Robo1−/− basal cells were mixed with WT luminal cells (KO/WT), the resulting mosaic organoids produced little/no milk upon differentiation (FIG. 12C). However, when WT basal cells were mixed with Robo1−/− luminal cells (WT/KO), the resulting organoids generated milk (FIG. 12D), similar to the milk production in WT/WT organoids (FIG. 12A). These data show that ROBO1 expression is required in the basal, and not the luminal, compartment of the mammary gland in order for luminal cells to produce milk upon hormonal stimulation.

Figure 13:
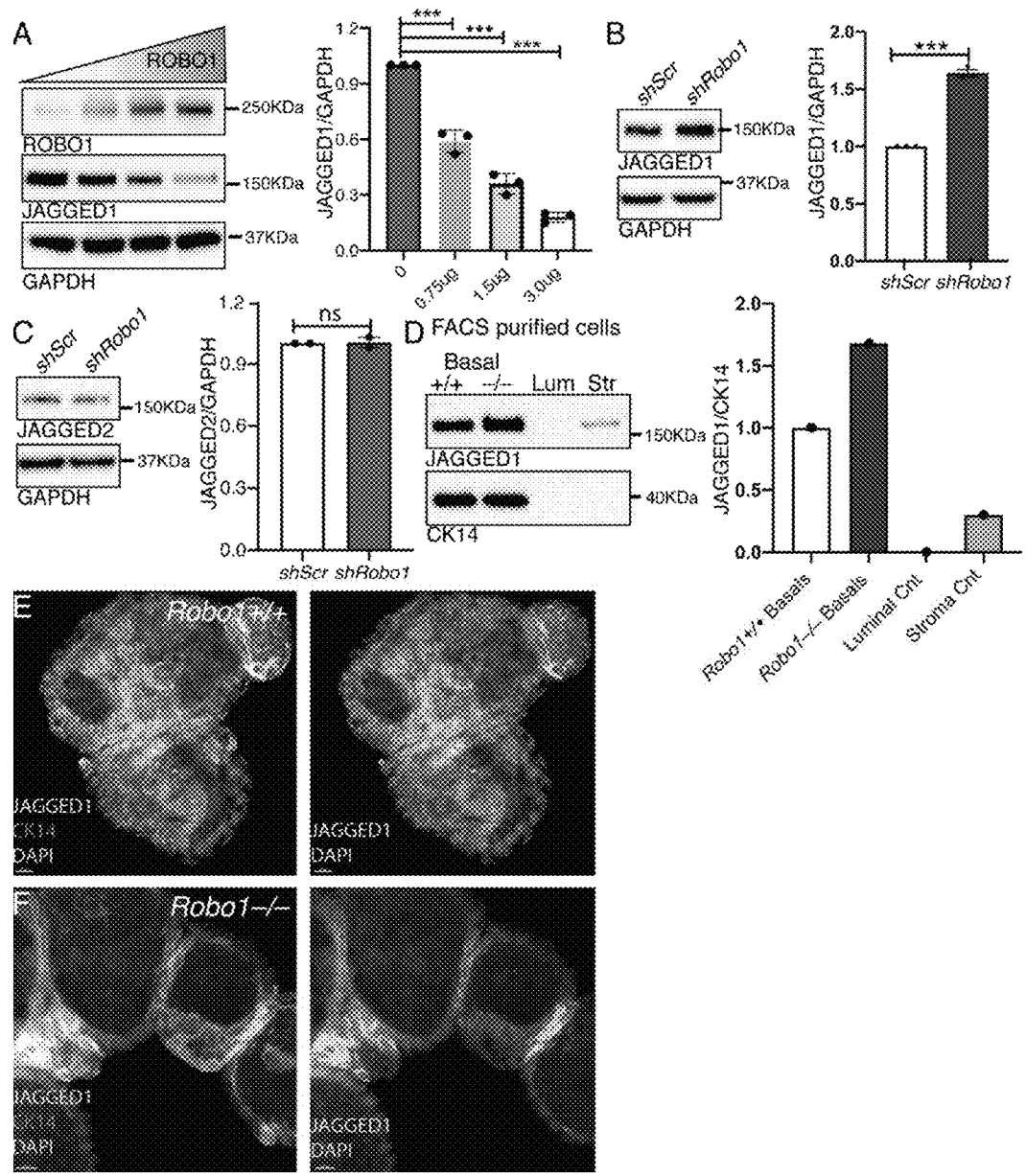
FIG. 13: ROBO1 Inhibits Jagged1 Expression in Basal Cells. (A) Immunoblots and quantification of HEK293 lysates from cells expressing increasing amounts of Robo1 plasmid (ROBO1) show decreasing levels of JAGGED1 expression. GAPDH is the loading control. (B) Immunoblots and quantification of HEK293 lysates from Robo1 knockdown (shRobo1) cells show increased JAGGED1 expression and no change in JAGGED2 expression. (C) Primary mammary epithelial cells were FACS-purified from Robo1+/+ and Robo1−/− animals. JAGGED1 expression is increased in Robo1−/− basal cells compared to WT. (D) Immunohistochemistry for JAGGED1 and basal marker cytokeratin15 (CK14) shows increased JAGGED1 expression in the basal cells of a Robo1−/−, compared to Robo1+/+, mammary organoid. (***p<0.001).

ROBO1 Inhibits Jagged1 Expression in Basal Cells:

One way to regulate Notch expression is to control the expression levels of Notch ligands Jagged1, Jagged2 or Delta. To investigate if ROBO2 regulated Notch ligand expression, cells were transfected with increasing amount of a plasmid expressing Robo1. After 48H, the cells were harvested and immunoblotting performed with antibodies directed against ROBO1, JAGGED1 (JAG1) and GAPDH (loading control) (FIG. 13A). The data show that increasing ROBO1 expression resulted in decreasing JAGGED 1 expression. Next Robo1 expression was knocked down using siRNA. After 48H cells, JAGGED1 and JAGGED expression were evaluated by immunoblot. Increased expression of JAGGED1 and no change in the expression JAGGED2 was observed (FIG. 13B, C). To examine if this regulation of JAGGED1 occurs in vivo, subpopulations of primary WT and Robo1−/− mammary epithelial cells were purified using fluorescent activated cell sorting (FACS) into basal, luminal and stromal subpopulations and then analyzed by immunoblot for JAGGED1 and Cytokeratin14 (CK14) (loading control) (FIG. 13D). More JAGGED1 was observed in Robo1−/−, compared to Robo1+/+, basal cells. There was no detectable expression in luminal cells and only modest expression in stromal cells; these data are similar to the results obtained by knocking down Robo1 expression in a cell line (FIG. 13B). We also evaluated JAGGED1 expression by immunostaining Robo1+/+ and Robo1−/− organoids (FIG. 13E, F). More JAGGED1 expression was observed in the basal cells of Robo1−/−, compared to Robo1+/+, organoids. Taken together, these data show that ROBO1 inhibits JAGGED1 expression in mammary basal cells, and loss of Robo1 results in increased JAGGED1. Increased JAGGED1 expression will enhance NOTCH signaling in the adjacent alveolar progenitor cells, inhibiting their differentiation into milk-producing alveolar cells. Thus, one mechanism by which ROBO1 regulates milk production is by governing the levels of Notch ligand JAGGED1 in the basal compartment of the mammary gland.

Materials and Methods

Animals:

All animal procedures were performed in accordance with the University of California, Santa Cruz (UCSC) Institutional Animal Care and Use Committee (IACUC). All Robo1 mice were generated and genotyped as previously described[11].

Mammary Fat Pad Clearing, and Transplantation:

A small mammary gland tissue fragment from an 8-week-old WT and Robo1 KO mouse was contralaterally transplanted into pre-cleared fat pads of Foxn1$^{nu}$. Contralateral outgrowths were harvested at pregnant day 18.5 and subjected to carmine staining.

Mammary Gland Whole-Mount Carmine-Alum Assays:

Mouse mammary glands were surgically dissected, spread onto a glass slide, and fixed in Carnoy's solution (25% glacial acetic acid and 75% ethanol). Following a briefly dehydration, glands were stained overnight in 0.2% carmine and 0.5% aluminum potassium sulphate, dehydrated in graded solutions of ethanol (70%, 95% and 100%), cleared in toluene; and mounted with permount.

Fat Pad Filling Analysis:

Paraffin embedded Robo1 KO or WT littermate tissue or contralateral outgrowths were sectioned and subjected to hematoxylin and eosin (H&E) staining. Images were analyzed using ImageJ, and percentage fat pad filling was calculated by measuring the area occupied by the alveoli.

Immunohistochemistry and Beta-Galactosidase Staining:

Tissue was fixed in 4% paraformaldehyde. Paraffin embedded tissue was sectioned at 6 μm and mounted serially. Standard protocols were followed for immunohistochemistry. For beta-galactosidase staining, 40 mg/ml 5-bromo-4-chloro-3-indolyl-β-D-galactopyranoside was prepared in a 1M phosphate buffer containing 1M MgCl2 and 10 mM potassium ferrous cyanide. Cryosections of tissue is treated with attain solution at 37° C. for 1.5-24H, washed with PBS, dehydrated through ethanol, fixed with xylene and coverslipped 4

Microscopy:

Brightfield imaging was performed on a Biorevo BZ-9000 Digital Microscope (Keyence) and confocal microscopy performed on a Nikon C2 Confocal, Leica SP5 confocal. Collected data were analyzed using ImageJ.

Co-Immunoprecipitation:

Adherent cells were lysed in 1 mL of 1× lysis buffer (137 nM NaCl, 10 mM Tris-HCl pH8, 2 nM EDTA, 1 mM sodium orthovanadate) supplemented with 1 percent Igepal NP40 (Sigma), 1 mM phenylmethanesulfonylfluoride (PMSF), 1 mM leupeptin, 1 mM aprotinin, and phosphatase inhibitors (Roche Complete). Cell lysate was incubated for 15 minutes at 4° C. with gentle rocking followed by centrifugation at 12,000 rpms for 10 minutes. Soluble phase was incubated with Dynabeads protein A (Thermo-fisher) conjugated with 1 μg of antibody as per company protocol for 1 hr at room temp or 4 hr at 4° C. Samples were washed and eluted as per protocol. Eluted protein complex was mixed with 2× Lysis buffer and incubated at 70° C. for 10 minutes and 100° C. for 5 minutes.

Western Blotting:

Protein lysates were prepared by directly lysing adherent cells in 1× sample buffer supplemented with 5% beta-mercaptoethanol and boiled for 5 minutes. Protein lysate was resolved by SDS-PAGE and transferred to a PVDF for 90 minutes at 400 mA or overnight at 30 mA. Primary antibodies were used at the concentration indicated in Table 1 and incubated overnight at 4° C. HRP conjugated secondary antibodies (Jackson Labs) were used at 1:3000 and incubated for 45 minutes at room temp. All proteins were detected using Clarity ECL (BioRad) using a BioRad Chemi-Doc MP Imager and quantified using ImageLab software as previously described a.

2D Cell Cultures:

All cell lines were obtained American Type Culture Collection. MDA-MB-231 cells were cultured in DMEM growth medium (Gibco) supplemented with 10% heat-inactivated FBS (Seradigm) and 1× antibiotic-antimycotic (Gibco). Undifferentiated HC11 cells were cultured in RPMI-1640 growth medium (Gibco) and supplemented with 10 μg/mL bovine insulin (Sigma-Aldrich) and 10 ng/mL human EGF (Peprotech). Primary LECs were harvested from 8-week-old Robo1 KO or WT littermate as previously described 15.

3D Cell Cultures:

FACS purified AVPs were cultured in Matrigel (BD Bioscience) at a density of 5000 cell/100 uL and cultured in basal medium; DMEM: F12 phenol-free, 10 mM HEPES, N2 (Gibco), B27 (Gibco) supplemented with 100 ng/mL Neuregulin (R&D), 42.5 ng/mL R-Spondin1 (Peprotech) for 5 days. To differentiate cultured AVPs were grown in basal medium supplemented with $10^{-6}$ M dexamethasone (Sigma), 10 μg/mL bovine insulin (Sigma) and 5 μg/mL prolactin (National Hormone and Peptide program) for an additional 5 days. Acini were fixed and processed as previously described 44.

HC11 Dome Assay:

HC11 cells were grown in RPMI 1640 media (Gibco) supplemented with 10% fetal bovine serum (BioFluid Technologies), 5 μg/mL insulin (Sigma), and 10 ng/ml epidermal growth factor (EGF; Sigma). To induce differentiation in HC11 cells, confluent plates were given fresh media (RPMI 1640 media supplemented with 5% charcoal-stripped fetal bovine serum (BioFluid Technologies), 5 µg/mL insulin, and 10 ng/ml epidermal growth factor (EGF; Sigma) for 3 days followed by 24 hours of priming in priming medium (RPMI 1640 media supplemented with 5% charcoal-stripped fetal bovine serum (BioFluid Technologies), and 5 µg/mL insulin. After priming, DIP medium (RPMI 1640 media supplemented with 5% charcoal-stripped fetal bovine serum (BioFluid Technologies), $10^{-6}$ M dexamethasone (Sigma), 5 µg/mL insulin, and 5 µg/mL prolactin (National Hormone and Peptide program) was added with fresh media every 24 hours.

Lentiviral Production:

Production of lentiviral particles for scrambled, Robo1, Robo2 and Notch4, knockdown experiments involved combination transfection of psPAX2, pMD2.G, and pLVTHM-scrambled-GFP (SCR) or pLVTHM-sh-target GFP into HEK293T cells. Filtered (0.45 um) viral particles were then diluted in media to infect target mammary lines (MDA-MB-231 and HC11 cells).

Isolation of Mammary Epithelial Cells and Flow Cytometry:

Mechanically dissociated inguinal and thoracic mammary fat pads were prepared into cell suspension for FACS as described[17]. AVPs were isolated using FITC-CD14 (clone Sa14-2; BioLegend) and ACP-Cy7-CD117 (clone 2B8; BioLegend) as described[14].

In-Vivo Gamma Secretase Inhibitor (GSI):

GSI inhibitor (R04929097; MedchemExpress) was orally administer at 10 mg/kg for 5 days as described[29]. Mammary glands were harvest after 5 days of GSI or vehicle treatment and prepared for single cell analysis. Purified populations were collected and processed for RNA. Purified population numbers were analyzed using FlowJo.

RNA Extraction and RT-qPCR:

Total RNA was harvested from cells lysed in TRIzol reagent (Invitrogen) and phase separated according to manufacturer's protocol with an additional overnight RNA precipitation stem in ethanol (Macias et al., 2011). The RNA was further purified with TURBO DNase (Ambion) treatment. Total RNA quality was analyzed by agarose gel electrophoresis and quantified with an ND-1000 spectrophotometer (NanoDrop). cDNA libraries were prepared from 1 µg of total RNA using iScript cDNA synthesis kit (BioRad). Quantitative RT-PCR was performed in triplicates using light Cycler 480 SYBR Green I Master (Roche) and quantified using BioRad CFX'Connect Real-Time System and CFX Manager software (BioRad). Results were normalized to GAPDH.

ROBO1 Extracellular Domain Generation:

To generate protein fragments, HEK cells were transfected with plasmids corresponding to the fragment of interest. PEI transfection was performed according to the Cytographica protocol. 24 hours after transfection, the media was changed to OptiMEM. 8 days after transfection, the media was collected and centrifuged at 3000×g for 10 minutes. The supernatant was then filtered through a 0.45 µm PVDF filter.

TCA Precipitation:

Add 1 volume of TCA stock to 4 volumes of protein sample. Incubate 10 min at 4° C. Spin tube in microcentrifuge at 14K rpm, 5 min. Remove supernatant, leaving protein pellet intact Wash pellet with 200 µl cold acetone. Spin in microfuge at 14K rpm, 5 min. Repeat steps 4-6 for a total of 2 acetone washes. Dry pellet prior to suspending in sample buffer.

Bodipy 493/503 Staining:

Place cells in a half-volume of buffer or media. Make a 2× solution (2 µg/ml=7.6 µM) of Invitrogen™ BODIPY™ 493/503 dye in 0.5 mL volume of the same pre-warmed buffer or media (no cells, no BSA or serum) and mix vigorously to mechanically emulsify this solution. Immediately add to the solution of cells, mix and incubate up to 30 min.

Cubic Immunofluorescence:

Glands were harvested and fixed with 10% neutral buffer formalin (Sigma) overnight at 4° C. Fixation was quenched with PBST (0.1% Triton X-100; Sigma) containing 0.2% Glycine (Fisher Scientific) for 2×10 minutes. The glands were then incubated in CUBIC reagent 1A at 37° C. for 48 hours, followed by 3×10 minute washes with PBST as described 45. Glands were blocked with PBST/10% donkey serum (Sigma) overnight at 4° C. and then, incubated with primary antibodies in PBST/5% donkey serum for 48 hours at 4° C. Glands were then washed with PBST for 3×1 hour and incubated with secondary antibodies diluted in PBST/5% donkey serum for 24 hours at 4° C. To counterstain for DNA, glands were incubated with Hoechst diluted in PBST for 1 hour, then washed with PBST for 2×1 hour. Finally, glands were incubated with CUBIC reagent 2 at 4° C. until they were cleared, typically 24 hours.

Intraductal Injection:

Preparation for the injection: Mice were anesthetized using an isoflurane chamber and eye lubricant applied. Mice were continuously anesthetized with 2-4% isoflurane in oxygen via a nose cone. Hair is removed from the nipple areas with Nair chemical hair remover. Injection: At pregnant day 7, PBS or ROBO2 mAb is bilaterally injected into the nipples of glands #3, #4, #5 with 33-gauge beveled-ended needles (Hamilton) attached to a 50 µl syringe. Injection was performed very slowly (approximately 40 µl/min) to minimize potential damage caused by rapidly moving fluid within the ductal lumens. After injection: The animal is removed from the nose cone and moved to a separate cage for recovery 46

Ovariectomy, Hormone Treatments and Subcutaneous Injection:

C57BL mice (8-10 weeks old) were bilaterally ovariectomized and allowed to recover for 1 week[47]. During the recovery, mice were trained with oral administration Nutella. Mice were fed Nutella mixed with 17beta-estradiol (E, 1 µg, Sigma)+progesterone (P, 1 mg, Sigma) for three weeks (daily). For ROBO1-Ig5 ECD, prolactin (Prl, 200 µg, NHPP) was given by Nutella oral administration over one week (daily), starting after 1 week E+P. For ROBO2 mAb, prolactin (Prl, 50 µg) was injected by intraperitoneal injection over 2.5 weeks (daily), starting after 1 week E+P. ROBO1-Ig5 ECD was injected subcutaneously (7.5 mg/kg ROBO1-Ig5 ECD or PBS; daily) over the 2 weeks period, starting after 1 week of E+P. ROBO2 mAbs or IgG isotype control mAbs (2501 µg/mouse) were injected subcutaneously twice/week over 17 days, starting after 1 week of E+P[48].

Primers:

| Gene | Forward sequence | Reverse sequence |
|---|---|---|
| mHes1 | GTGGGTCCTAACGCAGTGTC (SEQ ID NO: 36) | ACAAAGGCGCAATCCAATATG (SEQ ID NO: 37) |
| mHey1 | TGAGCTGAGAAGGCTGGTAC (SEQ ID NO: 38) | ACCCCAAACTCCGATAGTCC (SEQ ID NO: 39) |
| mHey1 | CCG CAT CAA CAG TAG CCT TT (SEQ ID NO: 40) | TGC AAG ACC TCA GCT TTC TC (SEQ ID NO: 41) |
| mWap | TCTGCCAAACCAACGAGGAGTG (SEQ ID NO: 42) | AGAAGCCAGCTTTCGGAACACC (SEQ ID NO: 43) |
| mLalba | GAGTCGGAGAACATCTGTGGCA (SEQ ID NO: 44) | CTTCTCAGAGCACATGGGCTTG (SEQ ID NO: 45) |
| mXdh | GCTCTTCGTGAGCACCAGAAC (SEQ ID NO: 46) | CCACCCATTCTTTTCACTCGGAC (SEQ ID NO: 47) |
| mBtn1 | AGACAACGACGACTTCGAGGAG (SEQ ID NO: 48) | GTACCATCCAGAGGAGGTGCAAC (SEQ ID NO: 49) |
| mRobo1 | TTATGGTGATGTGGACCTTAGTA (SEQ ID NO: 50) | GGTTGTATGGGATGGTTGGAG (SEQ ID NO: 51) |
| mElf5 | ACCCTGCCTTTGAGCATCAGAC (SEQ ID NO: 52) | GCTTGTACTGGTCGCAGCAGAA (SEQ ID NO: 53) |
| mGapdh | CATGGCCTTCCGTGTTCCTA (SEQ ID NO: 54) | CCTGCTTCACCACCTTCTTGAT (SEQ ID NO: 55) |

Antibodies:

| Antibody | Clone | Catalog Number | Company | Species | Dilution |
|---|---|---|---|---|---|
| α-ER | HC-20 | sc-543 | Santa Cruz | Rabbit | 1:1000 |
| α-WAP | M-16 | sc-14832 | Santa Cruz | Goat | 1:250 |
| α-ELF5 | N-20 | sc-9645 | Santa Cruz | Goat | 1:250 |
| α-PLIN2 | 5205 | | Gift: McManaman lab | Rabbit | 1:100 |
| α-SMA | 1A4 | A2547 | Sigma | Mouse | 1:500 |
| α-CK8 | — | TROMA-1 | DSHB | Rat | 1:500 |
| α-CK5 | — | ab53121 | Abcam | Rabbit | 1:1000 |
| α-ROBO1 | — | ab7279 | Abcam | Rabbit | 1:500 |
| α-ROBO2 | — | ab75014 | Abcam | Rabbit | 1:500 |
| α-NOTCH4 ICD | H-225 | sc-5594 | Santa Cruz | Rabbit | 1:250 |
| α-NOTCH4 ECD | EPR18049 | ab184742 | Abcam | Rabbit | 1:1000 |
| α-NOTCH4 | EPNCIR101 | ab166605 | Abcam | Rabbit | 1:250 |
| α-NOTCH1 | C-20-R | sc-6014-R | Santa Cruz | Rabbit | 1:250 |
| α-NOTCH2 | M-20 | sc-7423 | Santa Cruz | Goat | 1:250 |
| α-NOTCH3 | D11B8 | mAb#5276 | Cell Signaling | Rabbit | 1:200 |
| α-STAT5a | C-6 | sc-271542 | Santa Cruz | Mouse | 1:250 |
| α-pSTAT5a/b | 5G4 | sc-81524 | Santa Cruz | Mouse | 1:250 |
| α-HES1 | E-5 | sc-166410 | Santa Cruz | Mouse | 1:250 |
| α-Histone H1 | FL-219 | sc-10806 | Santa Cruz | Rabbit | 1:1000 |
| α-GAPDH-HRP | FL-335 HRP | sc-25778 HRP | Santa Cruz | Rabbit | 1:1000 |
| α-EGFP | — | GFP-1020 | Aves lab Inc | Chicken | 1:500 |
| α-Myc | 9E10 | Sc-40 | Santa Cruz | mouse | 1:1000 |

REFERENCES

1 Macias, H. & Hinck, L. Mammary gland development. *Wiley interdisciplinary reviews. Developmental biology* 1, 533-557, doi:10.1002/wdev.35 (2012).

2 Raafat, A. et al. Expression of Notch receptors, ligands, and target genes during development of the mouse mammary gland. *J Cell Physiol* 226, 1940-1952, doi:10.1002/jcp.22526 (2011).

3 Dontu, G. et al. Role of Notch signaling in cell-fate determination of human mammary stem/progenitor cells. *Breast Cancer Res* 6, R605-615, doi:10.1186/bcr920 (2004).

4 Bouras, T. et al. Notch signaling regulates mammary stem cell function and luminal cell-fate commitment. *Cell stem cell* 3, 429-441, doi:10.1016/j.stem.2008.08.001 (2008).

5 Raouf, A. et al. Transcriptome analysis of the normal human mammary cell commitment and differentiation process. *Cell stem cell* 3, 109-118, doi:10.1016/j.stem.2008.05.018 (2008).

6 Chakrabarti, R. et al. Elf5 regulates mammary gland stem/progenitor cell fate by influencing notch signaling. *Stem Cells* 30, 1496-1508, doi:10.1002/stem.1112 (2012).

7 Jhappan, C. et al. Expression of an activated Notch-related int-3 transgene interferes with cell differentiation and induces neoplastic transformation in mammary and salivary glands. *Genes Dev* 6, 345-355 (1992).

8 Gallahan, D. et al. Expression of a truncated Int3 gene in developing secretory mammary epithelium specifically retards lobular differentiation resulting in tumorigenesis. *Cancer Res* 56, 1775-1785 (1996).

9 Smith, G. H. et al. Constitutive expression of a truncated INT3 gene in mouse mammary epithelium impairs differentiation and functional development. *Cell Growth Differ* 6, 563-577 (1995).

10 Marlow, R. et al. SLITs suppress tumor growth in vivo by silencing Sdf1/Cxcr4 within breast epithelium. *Cancer Res* 68, 7819-7827, doi:10.1158/0008-5472.CAN-08-1357 (2008).

11 Strickland, P., Shin, G. C., Plump, A., Tessier-Lavigne, M. & Hinck, L. Slit2 and netrin 1 act synergistically as adhesive cues to generate tubular bi-layers during ductal morphogenesis. *Development* 133, 823-832 (2006).

12 Borrell, V. et al. Slit/Robo signaling modulates the proliferation of central nervous system progenitors. *Neuron* 76, 338-352, doi:10.1016/j.neuron.2012.08.003 (2012).

13 Biteau, B. & Jasper, H. Slit/Robo signaling regulates cell fate decisions in the intestinal stem cell lineage of *Drosophila*. *Cell reports* 7, 1867-1875, doi:10.1016/j.celrep.2014.05.024 (2014).

14 Shore, A. N. et al. Pregnancy-induced noncoding RNA (PINC) associates with polycomb repressive complex 2 and regulates mammary epithelial differentiation. *PLoS Genet* 8, e1002840, doi:10.1371/journal.pgen.1002840 (2012).

15 Macias, H. et al. SLIT/ROBO1 signaling suppresses mammary branching morphogenesis by limiting basal cell number. *Dev Cell* 20, 827-840, doi:10.1016/j.devcel.2011.05.012 (2011).

16 Ballard, M. S. et al. Mammary Stem Cell Self-Renewal Is Regulated by Slit2/Robo1 Signaling through SNA1 and mINSC. *Cell reports* 13, 290-301, doi:10.1016/j.cerep.2015.09.006 (2015).

17 Shackleton, M. et al. Generation of a functional mammary gland from a single stem cell. *Nature* 439, 84-88, doi:10.1038/nature04372 (2006).

18 Stingl, J. et al. Purification and unique properties of mammary epithelial stem cells. *Nature* 439, 993-997, doi:10.1038/nature04496 (2006).

19 Ball, R. K., Friis, R. R., Schoenenberger, C. A., Doppler, W. & Groner, B. Prolactin regulation of beta-casein gene expression and of a cytosolic 120-kd protein in a cloned mouse mammary epithelial cell line. *EMBO J* 7, 2089-2095 (1988).

20 Desrivieres, S. et al. Comparative proteomic analysis of proliferating and functionally differentiated mammary epithelial cells. *Mol Cell Proteomics* 2, 1039-1054, doi:10.1074/mcp.M300032-MCP200 (2003).

21 Dickinson, R. E. & Duncan, W. C. The SLIT-ROBO pathway: a regulator of cell function with implications for the reproductive system. *Reproduction* 139, 697-704, doi:10.1530/REP-10-0017 (2010).

22 Deome, K. B., Faulkin, L. J., Jr., Bern, H. A. & Blair, P. B. Development of mammary tumors from hyperplastic alveolar nodules transplanted into gland-free mammary fat pads of female C3H mice. *Cancer Res* 19, 515-520 (1959).

23 Andersson, E. R., Sandberg, R. & Lendahl, U. Notch signaling: simplicity in design, versatility in function. *Development* 138, 3593-3612, doi:10.1242/dev.063610 (2011).

24 Chillakuri, C. R., Sheppard, D., Lea, S. M. & Handford, P. A. Notch receptor-ligand binding and activation: insights from molecular studies. *Semin Cell Dev Biol* 23, 421-428, doi:10.1016/j.semcdb.2012.01.009 (2012).

25 Jarde, T. et al. Wnt and Neuregulin1/ErbB signalling extends 3D culture of hormone responsive mammary organoids. *Nat Commun* 7, 13207, doi:10.1038/ncomms13207 (2016).

26 Bi, P. et al. Inhibition of Notch signaling promotes browning of white adipose tissue and ameliorates obesity. *Nat Med* 20, 911-918, doi:10.1038/nm.3615 (2014).

27 Huang, R., Zhou, Q., Veeraragoo, P., Yu, H. & Xiao, Z. Notch2/Hes-1 pathway plays an important role in renal ischemia and reperfusion injury-associated inflammation and apoptosis and the gamma-secretase inhibitor DAPT has a nephroprotective effect. *Ren. Fail.* 33, 207-216, doi:10.3109/0886022X.2011.553979 (2011).

28 Chen, Y. et al. Inhibition of Notch signaling by a gamma-secretase inhibitor attenuates hepatic fibrosis in rats. *PloS one* 7, e46512, doi:10.1371/journal.pone.0046512 (2012).

29 Regan, J. L. et al. Aurora A kinase regulates mammary epithelial cell fate by determining mitotic spindle orientation in a Notch-dependent manner. *Cell reports* 4, 110-123, doi:10.1016/j.celrep.2013.05.044 (2013).

30 Brose, K. et al. Slit proteins bind Robo receptors and have an evolutionarily conserved role in repulsive axon guidance. *Cell* 96, 795-806 (1999).

31 Howitt, J. A., Clout, N. J. & Hohenester, E. Binding site for Robo receptors revealed by dissection of the leucine-rich repeat region of Slit. *EMBO J* 23, 4406-4412, doi:10.1038/sj.emboj.7600446 (2004).

32 Liu, Z. et al. Extracellular Ig domains 1 and 2 of Robo are important for ligand (Slit) binding. *Mol Cell Neurosci* 26, 232-240, doi:10.1016/j.mcn.2004.01.002 (2004).

33 Morlot, C. et al. Structural insights into the Slit-Robo complex. *Proc Natl Acad Sci USA* 104, 14923-14928, doi:10.1073/pnas.0705310104 (2007).

34 Fukuhara, N., Howitt, J. A., Hussain, S. A. & Hohenester, E. Structural and functional analysis of slit and heparin binding to immunoglobulin-like domains 1 and 2 of *Drosophila* Robo. *J Biol Chem* 283, 16226-16234, doi:10.1074/jbc.M800688200 (2008).

35 Hivert, B., Liu, Z., Chuang, C. Y., Doherty, P. & Sundaresan, V. Robo1 and Robo2 are homophilic binding molecules that promote axonal growth. *Mol Cell Neurosci* 21, 534-545 (2002).

36 Evans, T. A. & Bashaw, G. J. Functional diversity of Robo receptor immunoglobulin domains promotes distinct axon guidance decisions. *Curr Bio* 20, 567-572, doi:10.1016/j.cub.2010.02.021 (2010).

37 Evans, T. A., Santiago, C., Arbeille, E. & Bashaw, G. J. Robo2 acts in trans to inhibit Slit-Robo1 repulsion in pre-crossing commissural axons. *Elife* 4, e08407, doi:10.7554/eLife.08407 (2015).

38 Aleksandrova, N. et al. Robo1 Forms a Compact Dimer-of-Dimers Assembly. *Structure* 26, 320-328 e324, doi:10.1016/j.str.2017.12.003 (2018).

39 Peschon, J. J. et al. An essential role for ectodomain shedding in mammalian development. *Science* 282, 1281-1284 (1998).

40 Lupu, C. et al. Cellular effects of heparin on the production and release of tissue factor pathway inhibitor in human endothelial cells in culture. *Arterioscler Thromb Vasc Biol* 19, 2251-2262 (1999).

41 Richter, W. F. & Jacobsen, B. Subcutaneous absorption of biotherapeutics: knowns and unknowns. *Drug Metab. Dispos.* 42, 1881-1889, doi:10.1124/dmd.114.059238 (2014).

42 Brisken, C. et al. Prolactin controls mammary gland development via direct and indirect mechanisms. *Dev Biol* 210, 96-106. (1999).

43 Le, L. T. et al. Loss of miR-203 regulates cell shape and matrix adhesion through ROBO1/Rac/FAK in response to stiffness. *J Cell Bio* 212, 707-719, doi:10.1083/jcb.201507054 (2016).

44 Harburg, G. et al. SLIT/ROBO2 signaling promotes mammary stem cell senescence by inhibiting Wnt signaling. *Stem cell reports* 3, 385-393, doi:10.1016/j.stemcr.2014.07.007 (2014).

45 Lloyd-Lewis, B. et al. Imaging the mammary gland and mammary tumours in 3D: optical tissue clearing and immunofluorescence methods. *Breast Cancer Res* 18, 127, doi:10.1186/s13058-016-0754-9 (2016).

46 Krause, S., Brock, A. & Ingber, D. E. Intraductal injection for localized drug delivery to the mouse mammary gland. *J Vis Exp*, doi:10.3791/50692 (2013).

47 Strom, J. O., Theodorsson, A., Ingberg, E., Isaksson, I. M. & Theodorsson, E. Ovariectomy and 17beta-estradiol replacement in rats and mice: a visual demonstration. *J Vis Exp*, e4013, doi:10.3791/4013 (2012).

48 Machholz, E., Mulder, G., Ruiz, C., Corning, B. F. & Pritchett-Corning, K. R. Manual restraint and common compound administration routes in mice and rats. *J Vis Exp*, doi:10.3791/2771 (2012).

While preferred aspects of the present invention have been shown and described herein, it will be apparent to those skilled in the art that such aspects are provided by way of example only. Numerous variations, changes, and substitutions will now occur to those skilled in the art without departing from the invention. It should be understood that various alternatives to the aspects of the invention described herein may be employed in practicing the invention. It is intended that the following claims define the scope of the invention and that methods and structures within the scope of these claims and their equivalents be covered thereby.

For reasons of completeness, certain aspects of the polypeptides, composition, and methods of the present disclosure are set out in the following numbered clauses:

1. A method of promoting milk production in a mammal, the method comprising:
   administering to the mammal a first agent that inhibits NOTCH4 activity in an amount sufficient to inhibit NOTCH4 activity, thereby promoting milk production.
2. The method of clause 1, wherein the first agent inhibits NOTCH4 activity by directly binding to NOTCH4 protein, by inhibiting the binding of ROBO2 to ROBO1, by promoting the binding of ROBO1 to NOTCH4, by inhibiting the expression of NOTCH4, or by inhibiting the expression of ROBO2.
3. The method of clause 1, wherein the first agent comprises a soluble ROBO1 extracellular domain (ECD).
4. The method of clause 3, wherein the soluble ROBO1 ECD is a murine, bovine, ovine, caprine, camelid, or human ROBO1 ECD.
5. The method of clause 3 or 4, wherein the ROBO1 ECD comprises a heterologous polypeptide.
6. The method of clause 5, where the heterologous polypeptide comprises a His tag, a hemagglutinin tag, an immunoglobulin (Ig) Fc region, or a Myc tag.
7. The method of clause 1, wherein the first agent comprises an RNAi construct that inhibits the expression of NOTCH4 or ROBO2.
8. The method of clause 7, wherein the RNAi construct is a short interfering RNA.
9. The method of clause 1, wherein the first agent comprises an anti-NOTCH4 antibody or a NOTCH4 binding fragment thereof.
10. The method of clause 9, wherein the first agent comprises a plurality of polyclonal anti-NOTCH4 antibodies.
11. The method of clause 9, wherein the anti-NOTCH4 antibody or a NOTCH4 binding fragment thereof is a monoclonal antibody or a NOTCH4 binding fragment thereof.
12. The method of clause 10, wherein the polyclonal anti-NOTCH4 antibodies are murine, bovine, ovine, caprine, camelid, or human polyclonal antibodies and wherein the species in which the polyclonal antibodies are generated matches the species of the mammal administered the first agent.
13. The method of clause 11, wherein the monoclonal antibody or a NOTCH4 binding fragment thereof is a bovine, ovine, caprine, or human monoclonal antibody or a NOTCH4 binding fragment thereof, and wherein the species from which the monoclonal antibody is derived matches the species of the mammal administered the first agent.
14. The method of clause 13, wherein the anti-NOTCH4 monoclonal antibody or a NOTCH4 binding fragment thereof is a bovinized, ovinized, caprinized, camelized, or humanized.
15. The method of clause 1, wherein the first agent comprises a soluble ROBO1 extracellular domain, the method further comprising administering a second agent that inhibits NOTCH4 activity to the mammal in an amount sufficient to inhibit NOTCH4 activity.
16. The method of clause 15, wherein the second agent comprises an RNAi construct that inhibits the expression of NOTCH4 or ROBO2.
17. The method of clause 16, further comprising a third agent comprises an RNAi construct that inhibits the expression of NOTCH4 or ROBO2.
18. The method of clause 1, wherein the method comprises administering at least one of a first agent, a second agent, a third agent, and a fourth agent that inhibits NOTCH4 activity, wherein each of the first agent, the second agent, the third agent, and the fourth agent is independently selected from a soluble ROBO1 ECD, an anti-NOTCH4 antibody, RNAi construct that inhibits the expression of NOTCH4, and RNAi construct that inhibits the expression of ROBO2.
19. A polypeptide comprising:
   a soluble ROBO1 extracellular domain fused to a heterologous polypeptide.
20. The polypeptide of clause 19, wherein the soluble ROBO1 ECD is a murine, bovine, ovine, caprine, or human ROBO1 ECD.
21. The polypeptide of clause 20, wherein the heterologous polypeptide comprises a His tag, a hemagglutinin tag, a human or murine Fc region, a Myc tag, or a fluorescent protein.
22. A pharmaceutical composition comprising:
   the polypeptide of any one of clauses 19-21 and a pharmaceutically acceptable carrier.
23. The pharmaceutical composition of clause 22 for use in promoting milk production in a mammal.
24. An anti-NOTCH4 antibody or a NOTCH4 binding fragment thereof that inhibits NOTCH4 activity.
25. The antibody of clause 24, wherein the antibody comprises a plurality of polyclonal antibodies.
26. The antibody of clause 24, wherein the antibody is a monoclonal antibody or a NOTCH4 binding fragment thereof.
27. The antibody of any one of clauses 24-26, wherein the antibody comprises a bovine, ovine, caprine, camelid, or human polyclonal antibodies or a monoclonal antibody where at least part of the monoclonal antibody comprises an antibody sequence from a bovine, ovine, caprine, or human antibody.
28. The antibody of clause 26, comprising a bovinized, ovinized, caprinized, camelized, or humanized antibody or any antigen binding fragment thereof.
29. A pharmaceutical composition comprising the antibody of any one of clauses 24-28 and a pharmaceutically acceptable carrier.

30. The pharmaceutical composition of clause 29 for use in promoting milk production in a mammal.
31. A polynucleotide comprising an RNAi construct that inhibits the expression of ROBO2 or NOTCH4.
32. The polynucleotide of clause 31 comprising at least one non-naturally occurring nucleotide.
33. The polynucleotide of clause 31 or 32, comprising one or more of SEQ ID NO: 32-SEQ ID NO: 35.
34. A pharmaceutical composition comprising the polynucleotide of any one of clauses 31-33.
35. The pharmaceutical composition of clause 34 for use in promoting milk production in a mammal.
36. A transgenic mammal comprising a genetic modification that results in one or more of the following phenotypes: expression of a soluble ROBO1 extracellular domain; inhibition of expression of ROBO2; and inhibition of expression of NOTCH4.
37. The transgenic animal of clause 36, wherein the phenotype is limited to mammary tissue.
38. The transgenic mammal of clause 36 or 37, wherein the transgenic animal is a bovine, ovine, caprine, or camelid.
39. The transgenic mammal of any one of clauses 36-38 comprising two genetic modifications that result in two of the listed phenotypes.
40. The transgenic mammal of any one of clauses 36-38 comprising three genetic modifications that result in all three of the listed phenotypes.
41. A method of promoting milk production, the method comprising:
   administering to the transgenic mammal of any one of claims 36-40 a pharmaceutical composition that inhibits NOTCH4 activity.
42. The method of clause 41, wherein the pharmaceutical composition is the composition of any one of clauses 22-23, 29-30, and 34-35.
43. The method of claim 41, wherein the transgenic animal comprises a genetic modification that results in expression of a soluble ROBO1 extracellular domain, the method further comprising administering the pharmaceutical composition of any one of clauses 22-23, 29-30 and 34-35 to the transgenic animal.
44. The method of claim 41, wherein the transgenic mammal comprises a genetic modification that results in inhibition of expression of ROBO2 and/or NOTCH4, the method further comprising administering to the transgenic animal the pharmaceutical composition of clause 34 or 35.

What is claimed is:

1. A method of promoting milk production in a mammal, the method comprising:
   administering to the mammal a first agent that inhibits Notch Receptor 4 (NOTCH4) activity by directly binding to NOTCH4 protein, by inhibiting the binding of Roundabout Guidance Receptor 2 (ROBO2) to Roundabout Guidance Receptor 1 (ROBO1), by promoting the binding of ROBO1 to NOTCH4, by inhibiting the expression of NOTCH4, or by inhibiting the expression of ROBO2 in an amount sufficient to inhibit NOTCH4 activity,
   wherein the first agent is selected from the group consisting of:
   (i) a soluble ROBO1 extracellular domain (ECD);
   (ii) an RNAi construct that inhibits the expression of NOTCH4 or ROBO2; and
   (iii) an anti-NOTCH4 antibody or a NOTCH4 binding fragment thereof,
   thereby promoting milk production.

2. The method of claim 1, wherein the first agent comprises a soluble ROBO1 extracellular domain (ECD).

3. The method of claim 2, wherein the soluble ROBO1 ECD is a murine, bovine, ovine, caprine, camelid, or human ROBO1 ECD.

4. The method of claim 2, wherein the ROBO1 ECD comprises a heterologous polypeptide.

5. The method of claim 4, where the heterologous polypeptide comprises a His tag, a hemagglutinin tag, an immunoglobulin (Ig) Fc region, or a Myc tag.

6. The method of claim 1, wherein the first agent comprises an RNAi construct that inhibits the expression of NOTCH4 or ROBO2.

7. The method of claim 6, wherein the RNAi construct is a short interfering RNA.

8. The method of claim 1, wherein the first agent comprises an anti-NOTCH4 antibody or a NOTCH4 binding fragment thereof.

9. The method of claim 8, wherein the first agent comprises a plurality of polyclonal anti-NOTCH4 antibodies.

10. The method of claim 8, wherein the anti-NOTCH4 antibody or a NOTCH4 binding fragment thereof is a monoclonal antibody or a NOTCH4 binding fragment thereof.

11. The method of claim 9, wherein the polyclonal anti-NOTCH4 antibodies are murine, bovine, ovine, caprine, camelid, or human polyclonal antibodies and wherein the species in which the polyclonal antibodies are generated matches the species of the mammal administered the first agent.

12. The method of claim 10, wherein the monoclonal antibody or a NOTCH4 binding fragment thereof is a bovine, ovine, caprine, or human monoclonal antibody or a NOTCH4 binding fragment thereof, and wherein the species from which the monoclonal antibody is derived matches the species of the mammal administered the first agent.

13. The method of claim 12, wherein the anti-NOTCH4 monoclonal antibody or a NOTCH4 binding fragment thereof is a bovinized, ovinized, caprinized, camelized, or humanized.

14. The method of claim 1, wherein the first agent comprises a soluble ROBO1 extracellular domain, the method further comprising administering a second agent, that inhibits NOTCH4 activity to the mammal, in an amount sufficient to inhibit NOTCH4 activity, wherein the second agent comprises an RNAi construct that inhibits the expression of NOTCH4 or ROBO2.

15. The method of claim 14, wherein the second agent comprises an RNAi construct that inhibits the expression of NOTCH4 and the method further comprising administering a third agent, that inhibits NOTCH4 activity to the mammal, in an amount sufficient to inhibit NOTCH4 activity, wherein the third agent comprises an RNAi construct that inhibits the expression of ROBO2.

16. The method of claim 1, wherein the method comprises administering at least one of a first agent, a second agent, a third agent, and a fourth agent that inhibits NOTCH4 activity, wherein each of the first agent, the second agent, the third agent, and the fourth agent is independently selected from a soluble ROBO1 ECD, an anti-NOTCH4 antibody, RNAi construct that inhibits the expression of NOTCH4, and RNAi construct that inhibits the expression of ROBO2.

\* \* \* \* \*